(12) United States Patent
Chen

(10) Patent No.: US 11,464,840 B2
(45) Date of Patent: Oct. 11, 2022

(54) UNIVERSAL NON-CLASSICAL MHC I VACCINES: HLA-E-RESTRICTED ANTIGENIC PEPTIDES AS UNIVERSAL VACCINES TO TREAT ALLERGY, INFLAMMATION, AUTOIMMUNE AND INFECTIOUS DISEASES, AND CANCERS

(71) Applicant: Swey-Shen Chen, San Diego, CA (US)

(72) Inventor: Swey-Shen Chen, San Diego, CA (US)

(73) Assignee: Swey-Shen Chen, San Diego, CA (US)

( * ) Notice: Subject to any disclaimer, the term of this patent is extended or adjusted under 35 U.S.C. 154(b) by 542 days.

(21) Appl. No.: 16/443,710

(22) Filed: Jun. 17, 2019

(65) Prior Publication Data
US 2020/0138928 A1    May 7, 2020

(51) Int. Cl.
*A61K 39/00* (2006.01)
*C07K 14/74* (2006.01)
*C07K 14/525* (2006.01)

(52) U.S. Cl.
CPC .... *A61K 39/001114* (2018.08); *C07K 14/525* (2013.01); *C07K 14/70539* (2013.01); *C07K 2319/02* (2013.01); *C07K 2319/03* (2013.01); *C07K 2319/035* (2013.01); *C07K 2319/40* (2013.01)

(58) Field of Classification Search
CPC combination set(s) only.
See application file for complete search history.

(56) References Cited

U.S. PATENT DOCUMENTS

| | | |
|---|---|---|
| 10,548,957 B2 | 2/2020 | Cantor et al. |
| 2003/0171280 A1* | 9/2003 | Soderstrom ............ C07K 14/47 424/184.1 |
| 2005/0196404 A1 | 9/2005 | Crew |
| 2007/0259403 A1 | 11/2007 | Miyagawa et al. |
| 2009/0081226 A1 | 3/2009 | Charreau et al. |
| 2012/0171195 A1 | 7/2012 | Ravindranath et al. |
| 2015/0361180 A1 | 12/2015 | Braud et al. |
| 2016/0152953 A1 | 6/2016 | Hantash |

(Continued)

OTHER PUBLICATIONS

Sequence alignment of SEQ ID 40 with Geneseq db access No. ARL79674 by Gross et al. 2008.*

(Continued)

*Primary Examiner* — Shanon A. Foley
(74) *Attorney, Agent, or Firm* — Swey-Shen Chen

(57) ABSTRACT

The embodiment of the invention is to enable universal non-classical MHC I peptide vaccines restricted to HLA-E, HLA-F and HLA-G. An algorithm was develop to predict HLA-E binding immunogenic or suppressorgenic peptides of the autologous origins, e.g., autoantigens, inflammatory antigens, IgE and cancer antigens, and of the microbial origins. Thus, the embodiment of the invention is to load the antigenic peptides of medical and therapeutic importance onto the non-polymorphic HLA-E, HLA-F, and HLA-G culminating in universal vaccines, bypassing highly polymorphic classical MHC I, e.g., HLA-A, HLA-B and HLA-C pathways, in order to treat autoimmune diseases, allergy, inflammatory diseases, cancers, and infectious diseases for all human population. Derlin-1 and UL40 pathways are utilized to enable antigen presentation and vaccine efficacies in the non-classical MHC I pathways.

7 Claims, 12 Drawing Sheets

Figure 1:
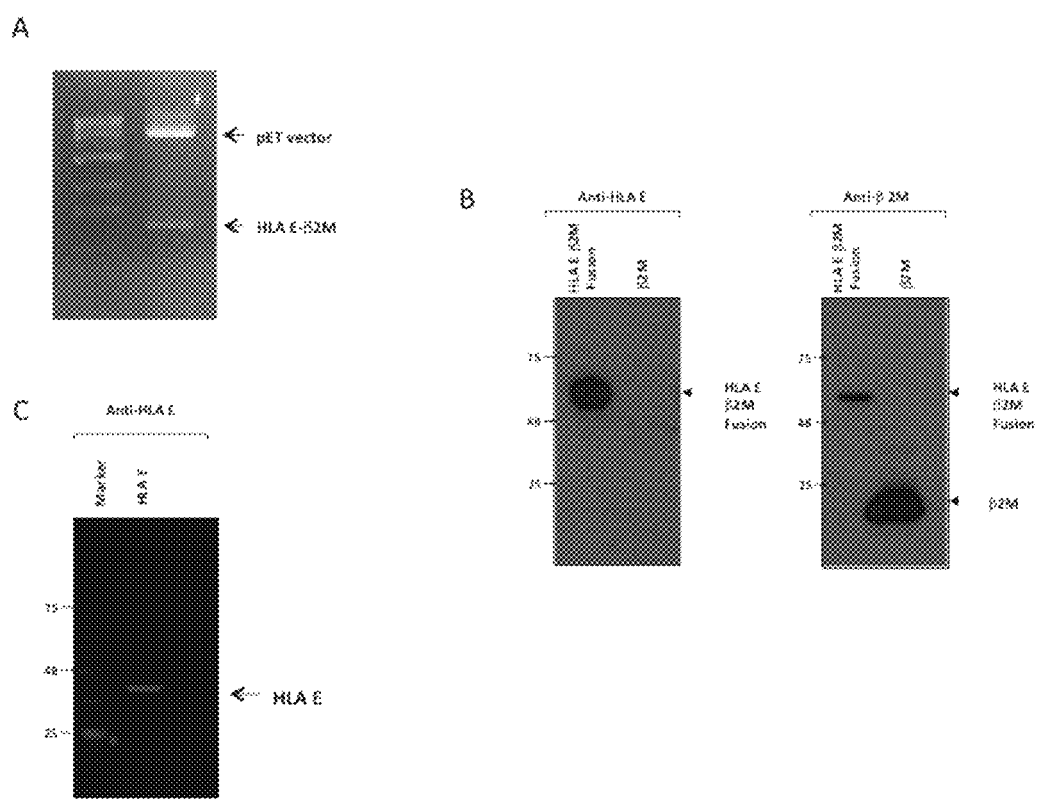

Specification includes a Sequence Listing.

(56) References Cited

U.S. PATENT DOCUMENTS

2017/0313773 A1 11/2017 Andre et al.
2019/0389953 A1 12/2019 Jiang et al.

OTHER PUBLICATIONS

Sequence alignment of SEQ ID 41 with Geneseq db access No. BCD82018 by Koomen 2015.*
Sequence alignment of SEQ ID 42 with Geneseq db access No. BCD82022 by Koomen 2015.*
Barry et al. (Nature Reviews Immunology. Feb. 2020; 113-127).*
Walters et al. (European Journal of Immunology. Dec. 2020; 50: 2075-2091).*
Mocarski et al. (Cellular Microbiology. 2004; 6(8): 707-717).*
Celik et al. The diversity of the HLA-E-restricted peptide repertoire explains the immunological impact of the Arg107Gly mismatch. Immunogenetics. 2016. . 68: 29-41.
Hansen et al. Broadly targeted CD8+ T cell responses restricted by major histocompatibility complex E. Science. 2016. 351: 714-720.
Lemberg et al. Intramembrane proteolysis of signal peptides: An essential step in the generation of HLA-E epitopes. J.I. 2001. 167: 6441-6446.
Lilley et al. A membrane protein required for dislocation of misfolded proteins from the ER. Nature. 2004. 429: 834-840.
Miller et al. Analysis of HLA-E Peptide-Binding Specificity and Contact Residues in Bound Peptide Required for Recognition by CD94/NKG2. J. I 2003. 171: 1389-1375.
Tomasec et al. Surface expression of HLA-E, an inhibitor of natural killer cells, enhanced by human cytomegalovirus gpUL40. Science. 2000. 287:1031-1033.

* cited by examiner

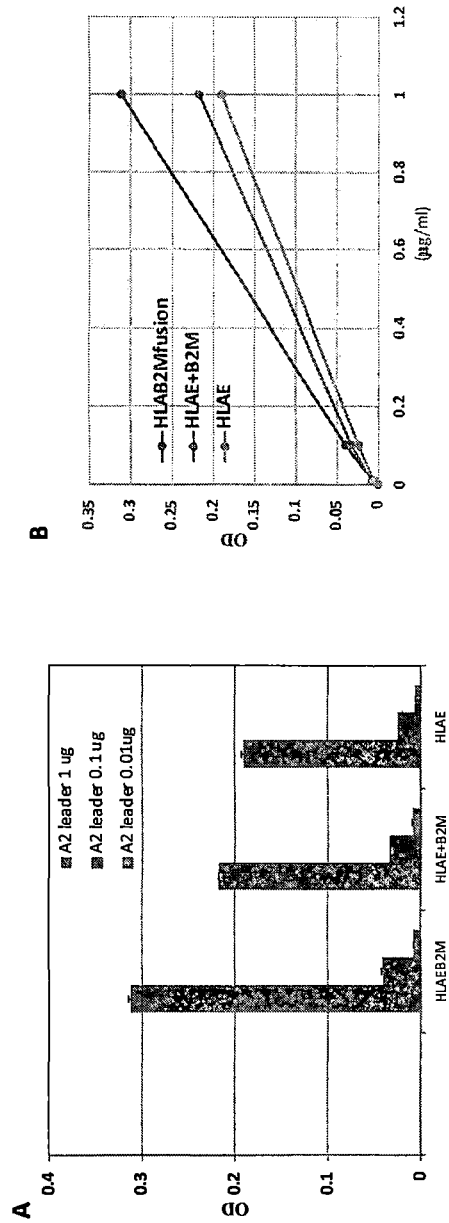

Fig 2. ELISA for the interaction of HLAE or HLA-E-β2 microglobulin fusion protein with biotinylated A2 leader peptide. 10 µg/ml of recombinant HLAE-β2 microgloblin protein or HLA E were incubated with biotinylated A2 leader peptide (NPRKVTAYL) with or without 10 µg/ml β2 macroglobulin in 50 µl buffer A (0.5 mM Tris Ph 6.6) at 18°C for two days. The complexes were added into anti-HLA-E antibody coated plate (2 µg/ml) and incubated for 1 hour. After washing three times with 1% BSA PBS, HRP-Avidin (Biolegend,# 405103,1:1000) was used to detect biotinylated peptide.

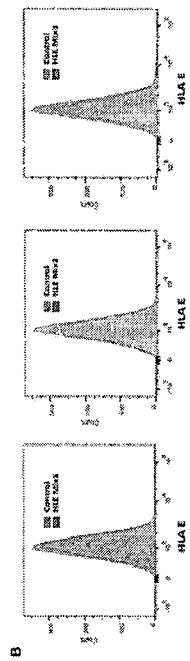
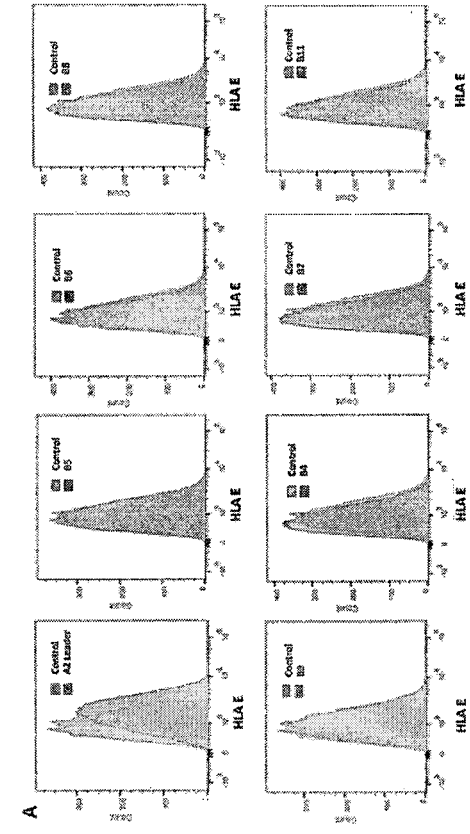
Fig 3. Effect of leader peptides to elevate HLA-E expression on TAP deficient T2 cells

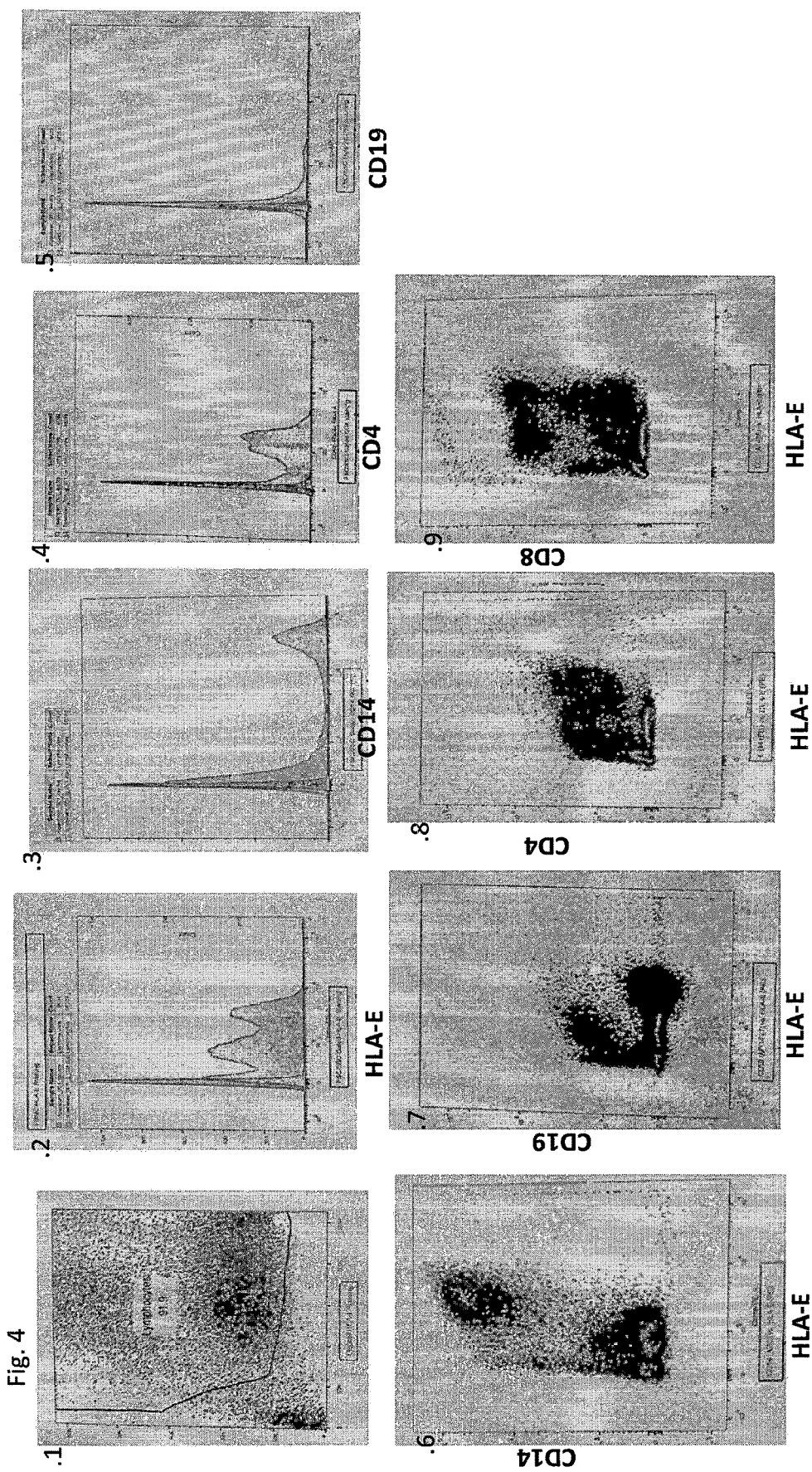

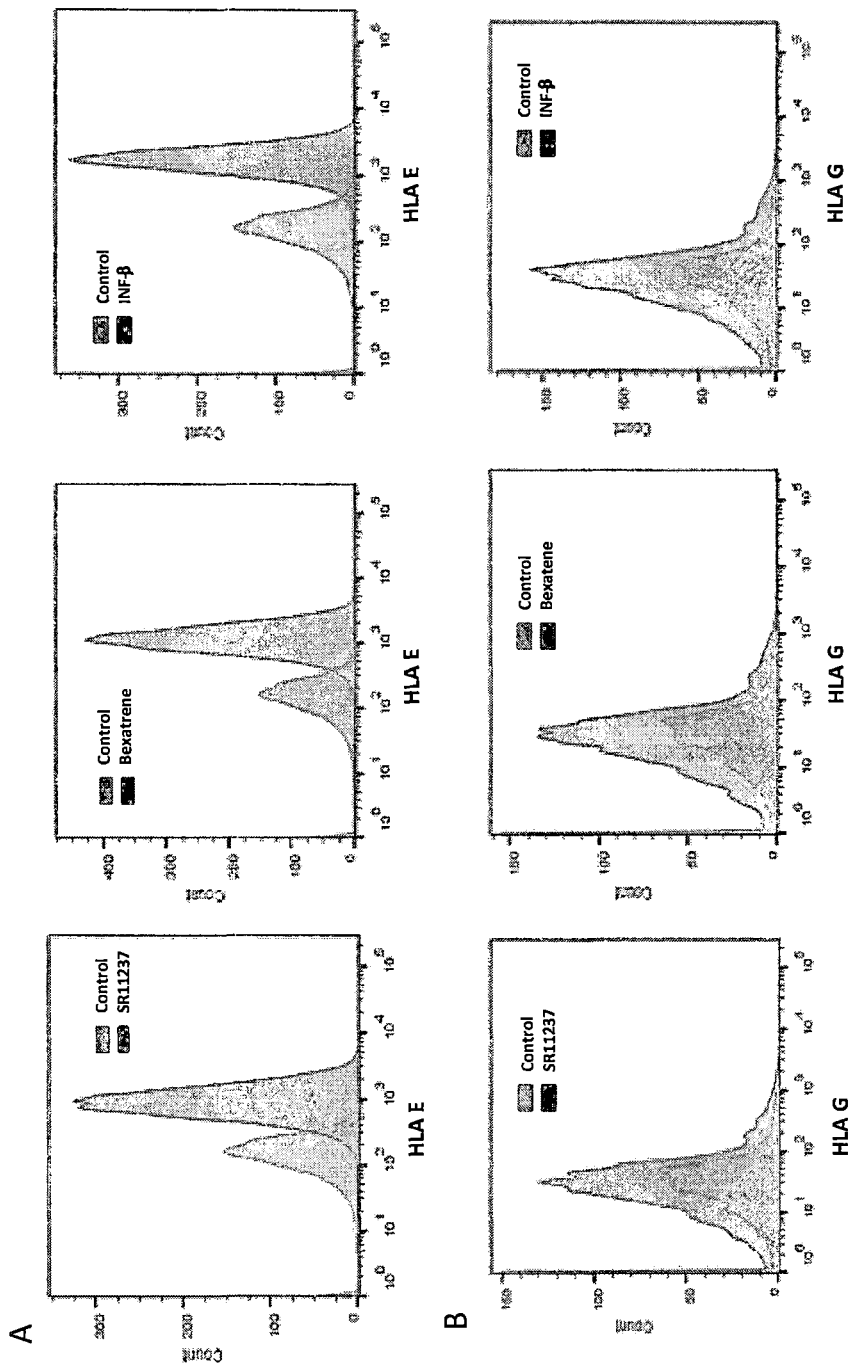

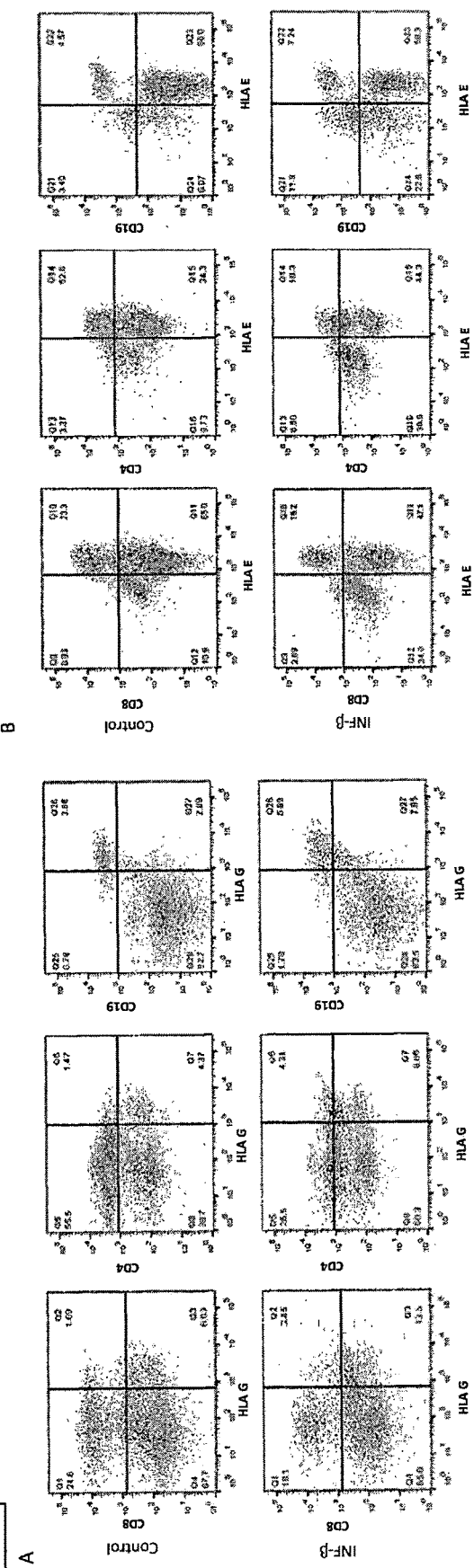

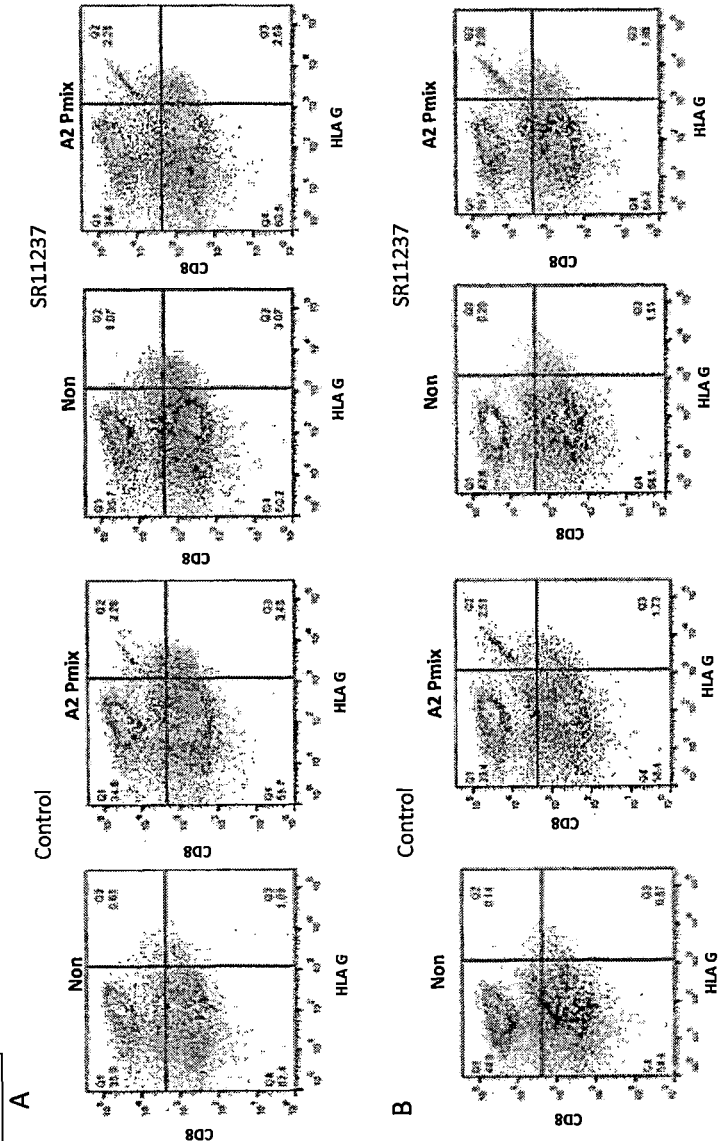

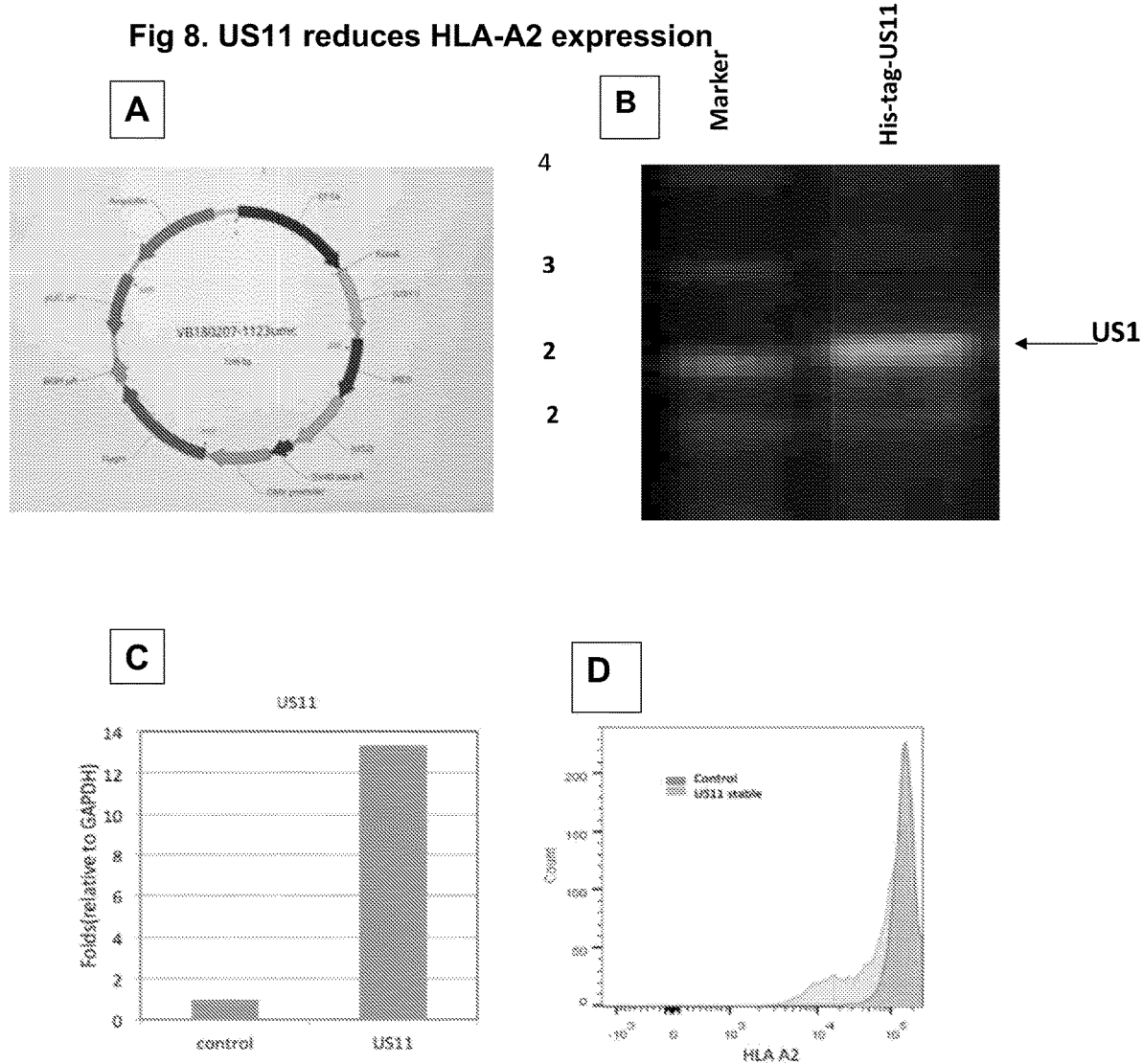

Fig 9. Derlin-1 siRNA knocked down Derlin-1 translation in dendritic cells and B and T cell tumors (A); Comparison of two different PEI reagent, Viromer blue vs Viromer red with respect to Cy3-lableled siRNA (B) and toxicity (C)
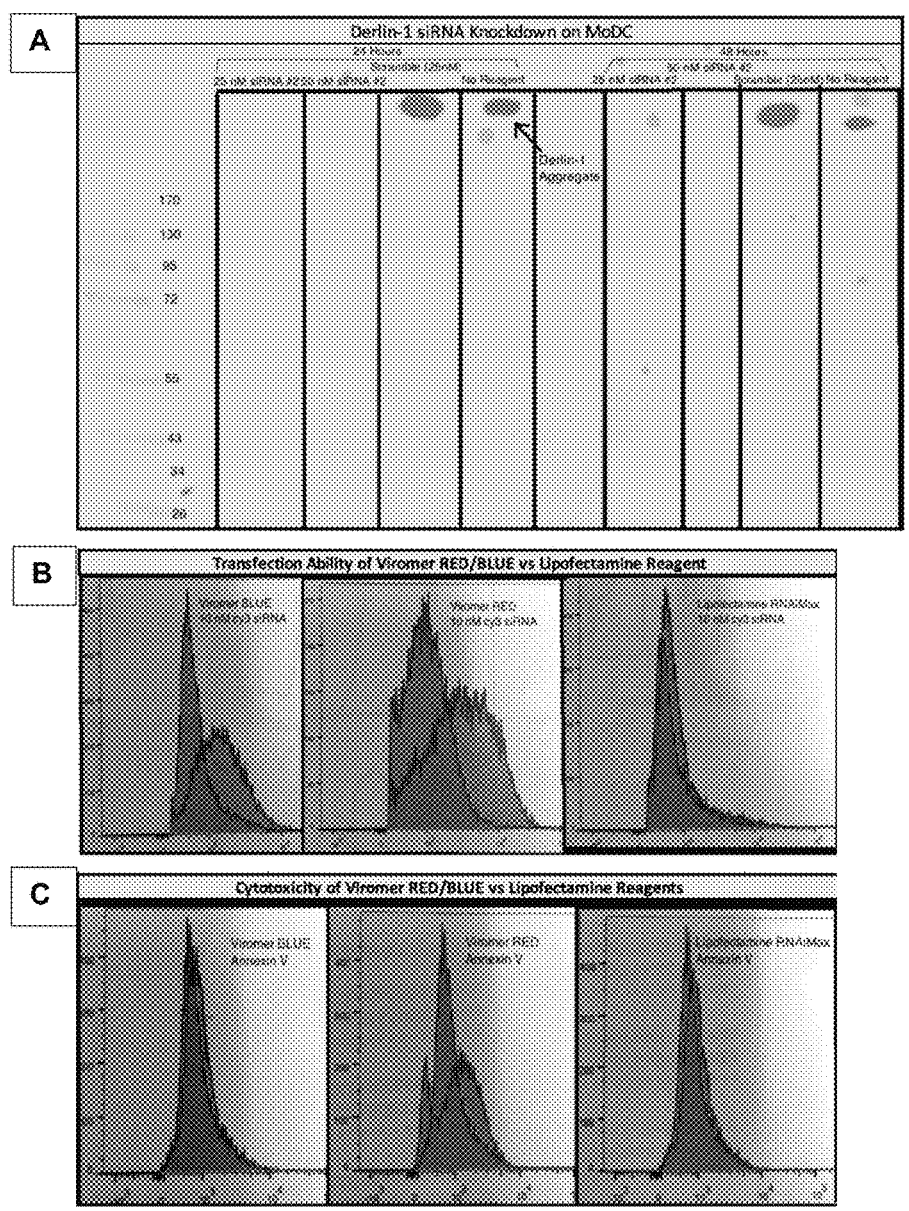

Fig 10. Product Concept Enabling Vaccine Model for a Nonclassical HLA-E based Universal Vaccine Targeting Infectious, Inflammatory, Autoimmune, Neurodegenerative Diseases, and Cancers
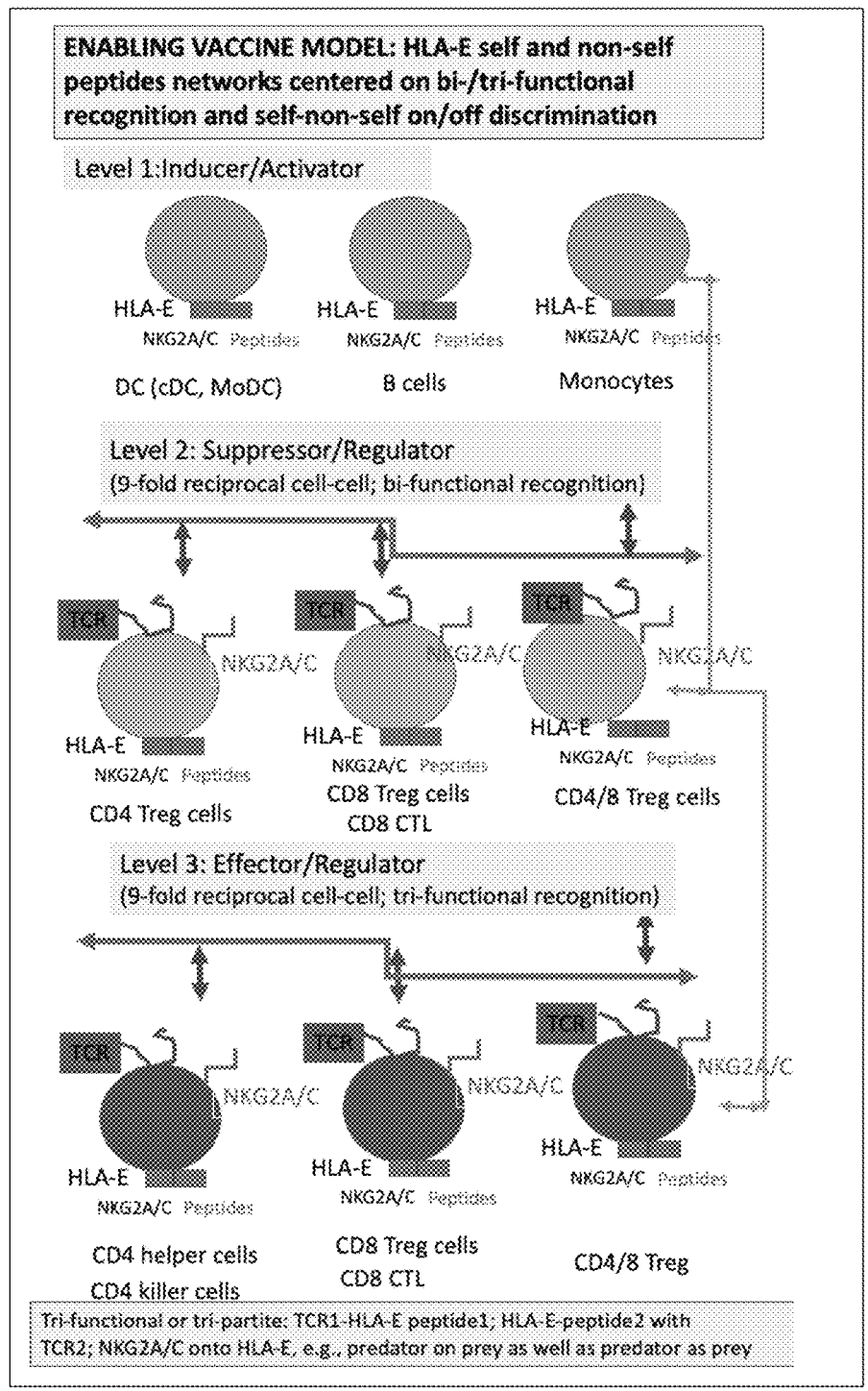

Fig 11. UL-40 as delivery for HLA-E based universal vaccines
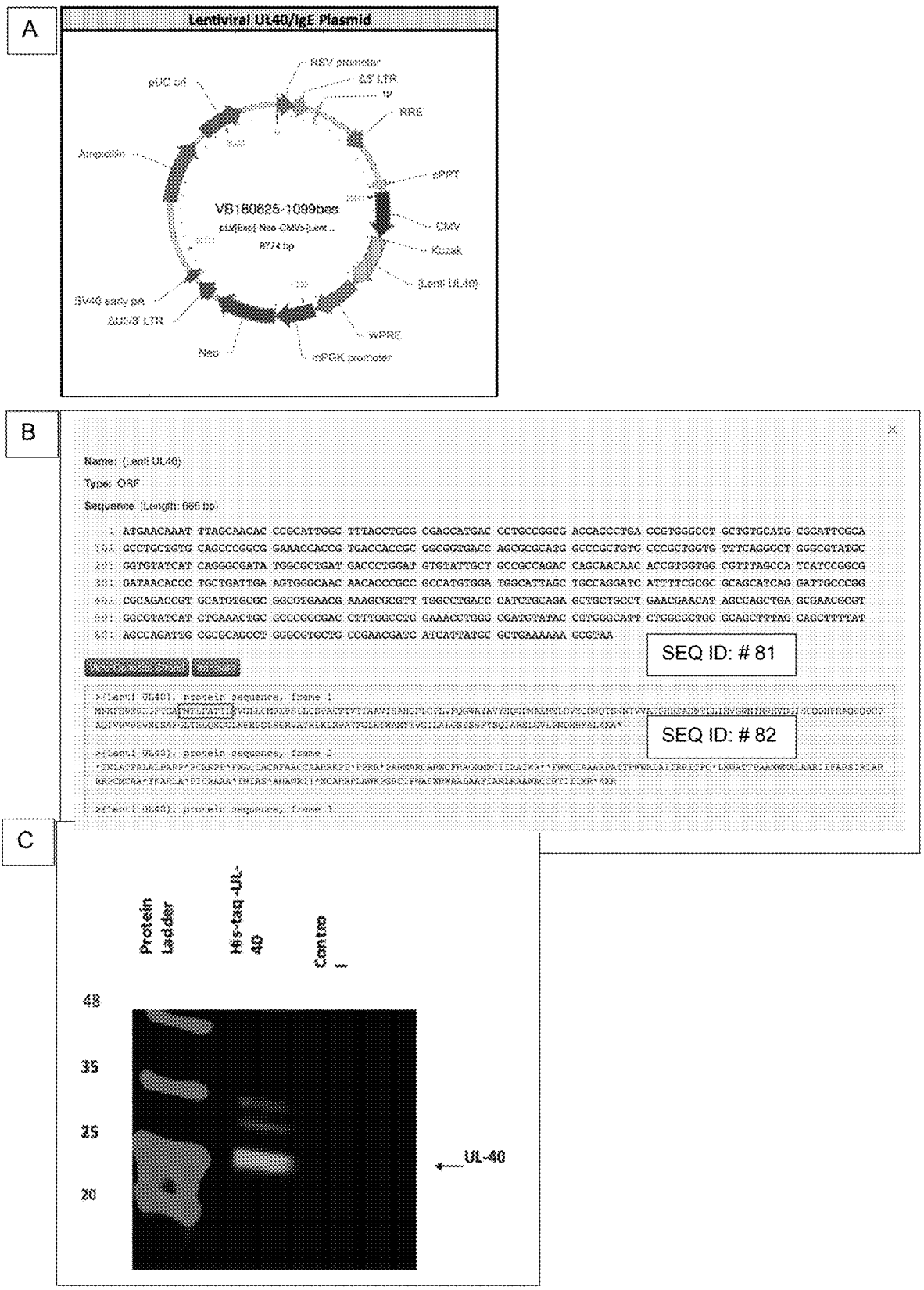

FIG 12. IGE HLA-E VACCINE CANDIDATES.
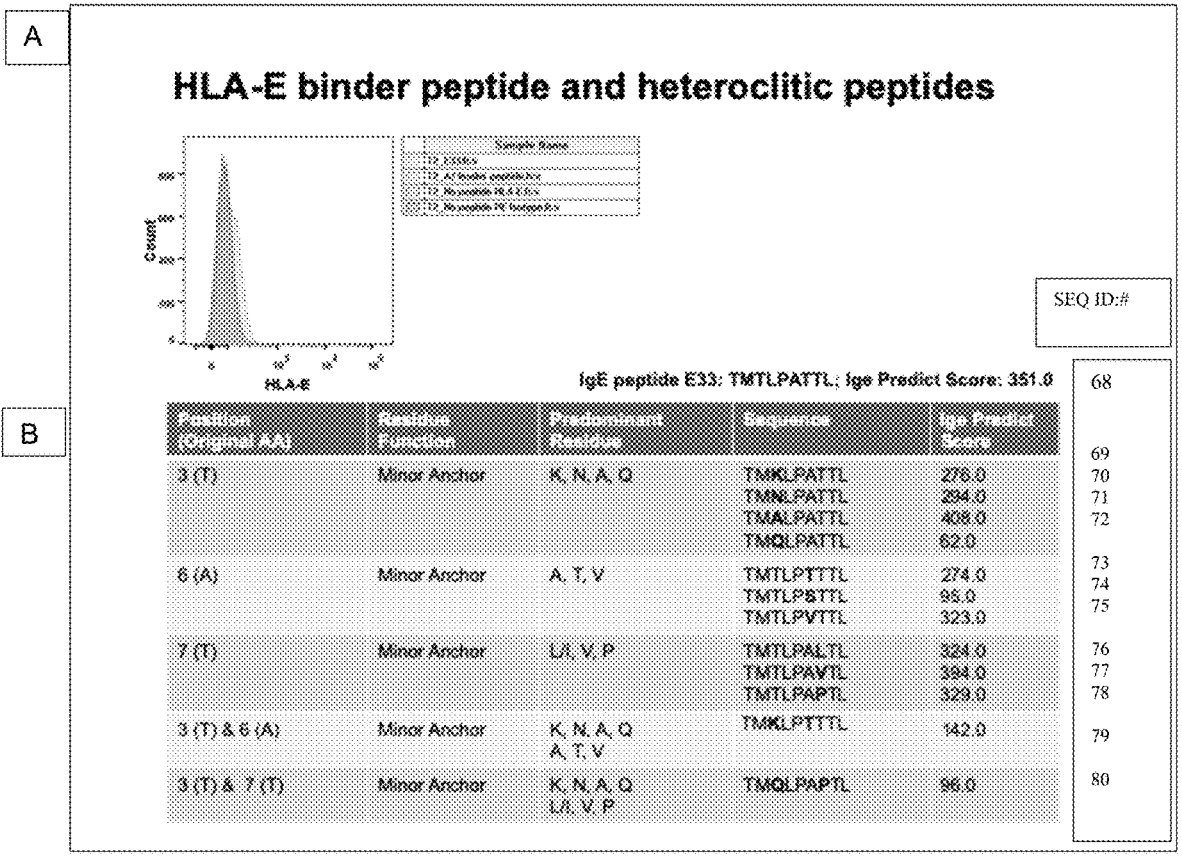

A

HLA-E binder peptide and heteroclitic peptides

B

SEQ ID:#

IgE peptide E33: TMTLPATTL; Ige Predict Score: 351.0 68

| Position (Original AA) | Residue Function | Predominant Residue | Sequence | Ige Predict Score | SEQ ID:# |
|---|---|---|---|---|---|
| 3 (T) | Minor Anchor | K, N, A, Q | TMKLPATTL<br>TMNLPATTL<br>TMALPATTL<br>TMQLPATTL | 278.0<br>294.0<br>408.0<br>62.0 | 69<br>70<br>71<br>72 |
| 6 (A) | Minor Anchor | A, T, V | TMTLPTTTL<br>TMTLPSTTL<br>TMTLPVTTL | 274.0<br>95.0<br>323.0 | 73<br>74<br>75 |
| 7 (T) | Minor Anchor | L/I, V, P | TMTLPALTL<br>TMTLPAVTL<br>TMTLPAPTL | 324.0<br>394.0<br>329.0 | 76<br>77<br>78 |
| 3 (T) & 6 (A) | Minor Anchor | K, N, A, Q<br>A, T, V | TMKLPTTTL | 142.0 | 79 |
| 3 (T) & 7 (T) | Minor Anchor | K, N, A, Q<br>L/I, V, P | TMQLPAPTL | 96.0 | 80 |

C

HLA-E IGE BINDER PEPTIDES (CONTINUED)
| SEQ ID: | Position | Sequences | SEQ ID: | Position | Sequences |
|---|---|---|---|---|---|
| SEQ ID: #18 | 174~182 | TLTVTSTLP | SEQ ID: #37 | 308~316 | AASPSQTVQ |
| SEQ ID: #19 | 176~184 | TVTSTLPVG | SEQ ID: #38 | 134~142 | ITCLVVDLA |
| SEQ ID: #20 | 198~206 | VTHPHLPRA | SEQ ID: #39 | 314~322 | TVQRAVSVN |
| SEQ ID: #21 | 177~185 | VTSTLPVGT | SEQ ID: #40 | 6~14 | FTPPTVKIL |
| SEQ ID: #22 | 219~227 | AAPEVYAFA | SEQ ID: #41 | 91~99 | QVTYQGHTF |
| SEQ ID: #23 | 133~141 | TITCLVVDL | SEQ ID: #42 | 8-16 | PPTVKILQS |
| SEQ ID: #24 | 218~226 | RAAPEVYAF | | | |
| SEQ ID: #25 | 223~231 | VYAFATPEW | | | |
| SEQ ID: #26 | 220~228 | APEVYAFAT | | | |
| SEQ ID: #27 | 175~183 | LTVTSTLPV | | | |
| SEQ ID: #28 | 315~323 | VQRAVSVNP | | | |
| SEQ ID: #29 | 135~143 | TCLVVDLAP | | | |
| SEQ ID: #30 | 221~229 | PEVYAFATP | | | |
| SEQ ID: #31 | 196~204 | CRVTHPHLP | | | |
| SEQ ID: #32 | 87~95 | TYTCQVTYQ | | | |
| SEQ ID: #33 | 92~100 | VTYQGHTFE | | | |
| SEQ ID: #34 | 7~15 | TPPTVKILQ | | | |
| SEQ ID: #35 | 224~232 | YAFATPEWP | | | |
| SEQ ID: #36 | 313~321 | QTVQRAVSV | | | |

UNIVERSAL NON-CLASSICAL MHC I VACCINES: HLA-E-RESTRICTED ANTIGENIC PEPTIDES AS UNIVERSAL VACCINES TO TREAT ALLERGY, INFLAMMATION, AUTOIMMUNE AND INFECTIOUS DISEASES, AND CANCERS

CROSS REFERENCES TO RELATED APPLICATION

The application does not claim benefit of earlier filing date.

STATEMENT REGARDING FEDERALLY SPONSORED RESEARCH OR DEVELOPMENT

None

THE NAME OF THE PARTY TO JOINT RESEARCH AGREEMENT

None

INCORPORATION-BY-REFERENCE OF MATERIAL SUBMITTED ON A READ-ONLY OPTICAL DISC OR AS A TEXT FILE VIA THE OFFICE OF ELECTRONIC FILING SYSTEM (EFS-WEB)

This Sequence.txt and IDS are submitted to EFS-WEB

STATEMENT REGARDING PRIOR DISCLOSURES BY THE INVENTOR OR A JOINT INVENTOR

None

BACKGROUND OF INVENTION

Technical field. To enable composition of non-classical MHC Ib binding peptide as universal vaccines for alleviating allergy and autoimmune diseases. Solution: Human non-classical MHC Ib exhibits no polymorphism underlying commonality of peptide binding, hence a singular MHC Ib-based universal vaccines in human population. A CMV viral constituent protein UL40 encodes human leader peptide mimicry to evade immune surveillance, which was replaced with recombinant peptide vaccine with an immunogenic or a tolerogenic carrier. Related arts for constituents of non-polymorphic MHC Ib are cited in references of USPTO documents, WIPO documents and other Publications.

BRIEF SUMMARY OF THE INVENTION

The embodiment of the invention is to enable universal non-classical MHC Ib peptide vaccines restricted to HLA-E, HLA-F and HLA-G. An algorithm was developed to predict HLA-E binding immunogenic or suppressorgenic peptides of the autologous origins, e.g., autoantigens, inflammatory antigens, IgE and cancer antigens, and of the microbial origins. Thus, the embodiment of the invention is to load the antigenic peptides of medical and therapeutic importance onto the non-polymorphic HLA-E, HLA-F, and HLA-G culminating in universal vaccines, bypassing highly polymorphic classical MHC Ia, e.g., HLA-A, HLA-B and HLA-C pathways, in order to treat autoimmune diseases, allergy, inflammatory diseases, cancers, and infectious diseases for all human population. Derlin-1 and UL40 pathways are utilized to enable antigen presentation and vaccine efficacies in the non-classical MHC Ib pathways.

BRIEF DESCRIPTION OF THE SEVERAL VIEWS OF THE DRAWING(S)

Figures and Legends

Table 1 and Legend to Table 1

TABLE 1

Derlin-1 siRNA knocked down Derlin-1 mRNA expression in dendritic cells and B and T cell tumors

| | | Derlin siRNA #1 | | Derlin siRNA #2 | | Derlin siRNA #3 | |
|---|---|---|---|---|---|---|---|
| | | Day 1 | Day 2 | Day 1 | Day 2 | Day 1 | Day 2 |
| MODC | 25 nM | 36% KD | — | 25 nM | 49% KD | 67% KD | 5 nM | 62% KD | 37% KD |
| | 50 nM | 30% KD | — | 50 nM | 57% KD | 72% KD | 10 nM | 41% KD | 33% KD |
| | | Day 1 | Day 2 | 6 Hours | | 6 Hours | |
| T2 | 5 nM | 32% KD | 19% KD | 2.5 nM | 62% KD | | 1 nM | 59% KD |
| | 10 nM | 50% KD | 10% KD | 5 nM | 43% KD | | 2 nM | 33% KD |
| | 20 nM | 25% KD | 29% KD | 10 nM | 34% KD | | 4 nM | 28% KD |
| | | | | | | | 8 nM | 17% KD |
| | | | | 6 hours | | | |
| B721.221 | | | | 5 nM | 52% KD | | | |
| | | | | 10 nM | 50% KD | | | |

Legends to Figures and Table

FIG. 1. Construction of HLA E and β2 microglobulin fusion protein vectors. HLA-E was synthesized by PCR with Primers (SEQ ID NO:46, CGG GAT CCC GGC TCC CAC TCC TTG AAG and SEQ ID NO: 47, CCC AAG CTT GGG TTA CAA GCTGCTGTGAGA CTC AG). β2 microglobulin was synthesized by PCR with Primers (SEQ ID NO: 48, CGG GAT CCC GTG TCT CGC TCC GTG GCC and SEQ ID NO: 49, CCC AAG CTT GGG CAT GTC TCG ATC CCA CT AAC TAT CTT GGG). HLA-E and β₂ microglobulin were assembled together with linker, GGGSGG-GSGGGS by two primers (SEQ ID NO: 83, GGC GGC TCC GGA GGT GGT GGC TCT GGT GGA GGT GGA TCG TCT CGC TCC GTG GCC TTA, and SEQ ID NO: 84, GCC ACC ACC TCC GGA GCC GCC ACC TCC GAT GGT GGG CTG GGA AGC) and then was inserted into restriction side, BamHI and HindIII of pET45b+. (A) pET-HLA E β₂-microglobin fusion DNA vector from the aforementioned primers and linker strategy was digested by restricted enzymes, BamHI and HindIII, and β2 microglobulin DNA released shown by agarose gel. (B) Western blotting for fusion protein expressed in BL21 E. coli by anti-human HLA-E or anti-human β 2 microglobulin antibody (Biolegend) (C) Western blotting for HLA-E single protein expressed in BL21 *E. coli* by anti-human HLA-E. *E. coli* containing HLA-E β2 microglobulin fusion or β 2 microglobulin were growing overnight with IPTG (Sigma, 1 mM) at 20° C. Cells were collected and resuspended in PBS with PMSF (1 mM), lysozyme (Affymetrix) (1 mg/ml) and sonicated. The pellets were obtained by centrifugation at 10,000 g for 15 minutes and resuspended in guanidine hydrochloride (8M, Sigma). After centrifugation, supernatants were collected for Western blotting with anti-HLA-E (Biolegend, #342602) followed by HRP-conjugated anti-mouse antibody or HRP-conjugated anti-β2 microglobulin (Biolegend, #280303).

FIG. 2. Renaturation and restoration of conformation of HLA-E by leader peptides and β2m. ELISA for the interaction of denatured HLA-E or covalent HLA-E-β2 microglobulin fusion protein with biotinylated HLA-A2 leader peptide. 10 μg of denatured recombinant HLAE-β2 microglobulin fusion protein, or denatured HLA-E incubated with biotinylated A2 leader peptide (SEQ ID NO: 50, NPRKVTAYL) with or without 10 μg β2 microglobulin in 50 μl buffer A (0.5 mM-Tris pH at 6.6) at 18° C. for two days. The complexes were then added into anti-HLA E antibody coated plate (2 μg/ml) and incubated for 1 hour. After washing three times with 1% BSA PBS, HRP-Avidin (Biolegend #405103, 1:1000) was used to detect bound biotinylated leader peptide.

FIG. 3. Upregulation of surface HLA-E by peptide nonamers. Screening 9-mers of IgE epitope that were able to induce surface HLA-E expression in tap deficient T2 cells. T2 cells were cultured overnight in present of Panel A: A2 leader peptide-SEQ ID NO: 51, VMAPRTLLL) or IgE epitope, B5 (SEQ ID NO: 52, IPSNATSVT), B6 (SEQ ID NO: 53, LPRALMRST), B8 (SEQ ID NO: 54, QPRKTKGSG) and B9 (SEQ ID NO: 55, LPDARHSTT), SP4 (SEQ ID NO: 56, APSKGTVNL), SP7 (SEQ ID NO: 57, LPVGTRDWL) and SP11 (SEQ ID NO: 58, SPSQTVQRA), and Panel B: IgE epitope of Mixture1 (SEQ ID NO: 59, ILQSSCDGG, QSSCDGGH, SCDGGGHFP, DGGGHFPPT and GGHFPPTIQ), Mixture2 (SEQ ID NO: 60: HFPPTIQLL, PPTIQLLCL, TIQLLCLVS, QLLCLVSGY and LCLVSGYTP), and Mixture 3 (SEQ ID NO: 61, LVSGYTPGT, SGYTPGTIN, YTPGTINIT, PGTINITWL and TINITWLED) at the concentration of 100 μg/ml. Cells were then collected and stained with PE conjugated HLA E followed by FACS flow cytometry analysis.

FIG. 4. HLA-E on PBMC cell types. PBMC were isolated from the buffy coat of a human donor, and stained with fluorochrome-conjugated anti-CD14, anti-CD19, CD4, CD8, and HLA-E. The gated population (92%, shown on FIG. 4 panel 1) was subjected to single color histogram display against isotype control. Panel 2 for HLA-E on all cells (panel 2), compositions of CD14+ monocytes (panel 3), CD4+ T cells (panel 4), and CD19+B cells (panel 5). Two color analysis was conducted for HLA-E expression on monocytes (CD14, panel 6), B cells (CD19, panel 7) and CD4 T cell (panel 8), s or CD8 T cells (panel 9).

FIG. 5. Interferon-β and RXR agonists induce Surface HLA-E expression in immature MoDC cells. $1 \times 10^5$ of MoDCs isolated from PBMCs were cultured in RPMI with FBS 10%, 200 U/ml, IL-4 and 100 U/ml GM-CSF for 4 days and then treated with 100 nM SR11237 and 100 nM Bexarotene (Tocris), or Interferon-β (1,000 U) for 4 days. MoDCs were then collected and stained with fluorescence-conjugated antibody; APC-conjugated anti-CD83 (Biolegend) and PE-conjugated HLA-E (Biolegend) followed by fixation with 2% paraformaldehyde. Phenotype and HLA-E expression of MoDCs were performed by using a FACS, LRSII flow cytometry and the data were processed by using the Flowjo software.

FIG. 6. Modulation of surface HLA-G and HLA-E expression in PBMCs in present of interferon-β. Fresh buffy coat was obtained from San Diego blood blank. PBMCs (peripheral blood mononuclear cells) were isolated by density gradient centrifugation with Histopague-1077 (Sigma). $5 \times 10^5$ of PBMCs were seeded in anti-CD3 (10 μg/ml) coated 96 wells-plate and treated with interferon-I3 for 4 days. Cells were collected and stained with fluorescence-conjugated antibody; Alexa Fluor 488-conjugated anti-human CD8a (Biolegend), Pacific Blue-conjugated human CD4, APC-Cy7-conjugated human CD19 and PE conjugated-HLA-E or PE-Cy 7 conjugated HLA-G (Panel A) or HLA-E (Panel B), followed by fixation with 2% paraformaldehyde. Phenotype and HLA-E or HLA-G (Biolegend) expression were performed by using a FACS, LRSII flow cytometry and the data were processed as describe above.

FIG. 7. Modulation of HLA-G by RXR agonist. Surface HLA-G expression of CD8 T cells was observed induced by RXRα agonist, SR11237 (100 nmol/L)-treated immature (A) and mature (B) MoDCs in presence of A2 mix peptides (Biomatik). MoDCs isolated from A2 type of PBMCs, were cultured in 10% FBS RPMI with 200 U/ml IL-4 and 100 U/ml GM-CSF for 5 days as immature MoDCs and then proceeded for maturation with addition of cytokines cocktail containing TNFα (10 ng/ml), PGE2 (1 μg/ml), IL-6 (150 ng/ml) and IL-1β (5 ng/ml) (Biolegend) for another two days. Both mature and immature MoDC were incubated with SR11237 for 2 days and pulsed with A2 peptides of IgE epitope for 4 hr. Then MoDCs were co-cultured in anti-CD3 (10 μg/ml) coated plate for 5 days with T cells isolated from PBMCs by adhering PBMC to 100×20 mm plate and collecting suspended cells. Cells were then collected and stained with Alex Fluor 488-conjugated human CD8 and PE-Cy 7-conjugated human HLA G followed by fixation with 2% paraformaldehyde. Phenotype and HLA G expression of T cells were performed by using a FACS, LRSII flow cytometry, data were processed as describe above.

FIG. 8. US11 gene knockdowns HLA-A2 expression in T2 cells. (A) US11 and US2 was constructed in the pRB vector under the EF1A transcription factor spaced by IRES with stronger expression of the upstream US11 gene under promoter control. (B) Western blotting for recombinant protein, His-tag-US11 expressed in BL21 *E coli* by anti-His tag antibody. *E coli* containing pET45b-His-tag US11 were growing overnight with IPTG (Sigma, 1 mM) at 20° C. Cells were collected and resuspended in PBS with PMSF (1 mM), lysozyme (Affymetrix) (1 mg/ml) and sonicated. The pellets were obtained by centrifugation at 10,000 g for 15 minutes and resuspended in Urea (6M, Sigma). After centrifugation, supernatants were collected for Western blotting with HRP conjugated anti-his (Biolegend #652504) antibody. Effect of US11 expression on surface HLA-A2 expression. (C) Expression of US11 in US11 stable T 2 cells comparing to the control T2 cells. RNA of both US11 stable cells and T2 cells were purified by RNA extract Kit (Zymo Research, #11-328), First cDNA was prepared by RNA iScript cDNA Synthesis kit (Bio-Rad, #170-8891) followed by iTaq Universal SYBR Green Supermix Kit (BIO-RAD, #172-5121) with US11 primers (SEQ ID NO: 62, TGCCT GAATTATCCTT GACTCTT, SEQ ID: NO: 63, CTCG-GAATACTCTACTCTACTCGGTACT) and GAPDH primers (SEQ ID NO: 64, GAPDH, CCCTTCAT TGACCTCAACTA). (D) Both US11 T2 cells and control T2 cells were stained with APC-conjugated anti-Human HLA-E antibody (Biolegend, #343307) followed by FACS flow cytometry analysis with apparent diminution of HLA-A2 surface expression.

FIG. 9. Derlin-1 siRNA knocked down Derlin-1 translation in dendritic cells and B and T cell tumors by western blots. (A) Comparison of two different PEI reagent. Viromer blue vs Viromer red with respect to Cy3-labeled siRNA (B) and toxicity (C). Derlin-1 Knockdown Protein Verification by Western Blot (A). Confirms the knockdown of protein levels in MoDCs by Derlin-1 siRNA #2. For Lanes 1, 2, 5, and 6, the respective knockdowns were 49%, 57%, 67%, and 72%. Scramble included at concentration of 25 nM in wells (3) and (7). Wells (4) and (8) contain RPMI medium only. Mouse Anti-Derlin-1 mAb added at concentration of 1:1000 and Goat Anti-mouse IgG1 added at 1:10,000. (B) Transfection Ability of Viromer red/blue vs Lipofectamine RNAiMax. TAP-deficient T2-cells transfected with cy3-conjugated siRNA at 10 nM using manufacturer's recommended protocol for each reagent. Cells were stained, fixed, and detected 24 hours after transfection. PE laser was used to detect cells on BD LSR II. A shift to the right indicates a more efficient transfection reagent. (C) Cytotoxicity of Viromer RED/BLUE vs Lipofectamine RNAiMax. Extracellular staining of T2 cells with Annexin V was used to determine the number of cells undergoing active apoptosis after transfection with each reagent. BV421 laser was used to detect cells on BD LSR II. Cells were stained, fixed, and detected 24 hours after transfection. A shift to the right indicates that the transfection complexes were cytotoxic in a large number of cells.

FIG. 10. Product Concept of Enabling Vaccine Model for a Nonclassical HLA-E based Universal Vaccine Targeting Infectious, Inflammatory, Autoimmune, Neurodegenerative Diseases, and Cancers. At level I, HLA-E expressing APCs: DCs (cDCs, MoDCs), B cells, monocytes are capable of inducing CD8+ suppressor/Treg or CD8+ CTL (level 2) as well as level 3 CD4+ T cells according to the state of these APCs, e.g., extent of co-stimulation or co-suppression signals within the APC, modulated by the biochemical, proteomic and genomic landscapes of APCs. The state of engagement of level two cells also dictates and reciprocally the HLA-E/peptide cellular networks. Level 1 versus level 2 or 3 cells are bifunctional recognition via TCR (on T cells) and HLA-E/peptides (Complexed With peptides) on APC; and NKG2AC on T cells and HLA-E (Conformed By peptides). On the other hand, tri-functional recognition occurs amongst level 2 and level 3 cellular interaction, the first two interactions are similar to level I versus level 2 or 3, and the additional interaction is due to the presence of HLA-E with a self or foreign peptide, which thus serves as a prey being recognized by another level 2 or level 3 cell which serves as a predator, bearing the TCR. The enabling model herein also permits an indirect interaction of level 2 and level 3 cells via level one APC in a physical tripartite assembly or constellation (see orange connecting thread and arrows).

FIG. 11. UL-40 as delivery for HLA-E based universal vaccines. Plasmid designed and purchased using VectorBuilder.com. UL40 ORF uses CMV promotor. UL40 protein sequence (NCBI: P16780.1: SEQ ID NO: 81, SEQ ID NO: 82) was chosen from AD169 strain of human cytomegalovirus. The amino acids 15-23 on UL40 were replaced with a 9-mer from the IgHε (heavy constant epsilon region, SEQ ID NO: 43). This novel protein sequence was then placed into a lentiviral expressing plasmid. This plasmid was also designed and purchased using the VectorBuilder.com website. Plasmid is designed to be packaged within Lentivirus using external plasmids for virus proliferation and packaging.

FIG. 12. Screening of IgE epitope 9-mer which can induce surface HLA-E expression in TAP-deficient T2 cells. Peptide E33 (TMTLPATTL, SEQ ID NO: 68) was predicted by Ige Predict program. T2 cells ($2.5 \times 10^5$ cells/well) were cultured in the presence of E33 peptide or HLA-A2 leader peptide (10 μg/mL) in 96-well cell culture plate for overnight. Cell were collected and stained with PE anti-human HLA-E antibody followed by flow cytometric analysis (Panel A). Heteroclitic peptides (Panel B) were designed based on E33 peptide sequence according to predominant residue in the anchor residues (position 3, 6 and 7), and more HLA-E restricted IgE peptides were listed (Panel C Table)

Table 1: Summary of Derlin-1 Knockdowns with Various siRNAs. Cells transfected in 12 well plate at 60%-80% confluency. one ul Viromer blue was used per 1 ml final volume. Cells were lysed via centrifugation and resuspended in TRI reagent at time points of either 6 h, 24 h, and 48 h. Lysates were split for both protein verification and qPCR. Knockdowns are estimated using the ΔΔCt method. SiRNA #2 appeared most effective in reducing Derlin-1 mRNA levels in both monocyte-derived dendritic cells and T2 cells. Anti-Derlin-1 siRNA was designed using MITs website (sirna.wi.mit.edu) and siRNA design software (dharmacon-.horizondiscovery.com/rnai/sirna). SiRNA were chosen based on the criteria that they would bind no more than 15 nucleotides on off-target mRNA and that they would be capable of knockdown for all four of the Derlin-1 mRNA isoforms. Additionally, siRNAs with 40-60% GC content, no more than 3 identical nucleotides in a row, and 3' UU overhangs were used. The first siRNA (SEQ ID NO: 65, 5'-GAGGCCAGCAGACUAUUUAUU-3') was purchased from TriLink Biotechnologies and the second (SEQ ID NO: 66, 5'-GGACUUGGGAGGAAGAAAUUU-3') was purchased from Horizon Discovery. A third, modified siRNA with sequence 5'-SEQ ID NO: 67, O'me/G/O'me/ACUUGG-GAGGAAGAAAUUU-3' and DNA bases on the 1st and 8th nucleotide of the antisense strand was also designed and purchased from Horizontal Discovery. Scramble siRNAs were purchased from Horizontal Discovery (D-001810-10-05, ON-TARGET plus Non-targeting Pool).

DETAILED DESCRIPTION OF THE INVENTION

Human leukocyte antigen-E (HLA-E, SEQ ID NO: 1, SEQ ID NO: 2, SEQ ID NO: 3, SEQ ID NO: 4, SEQ ID NO: 5, SEQ ID NO: 6, SEQ ID NO: 7) a non-classical major histocompatibility complex I (MHC I), homologous to H-2 Qa-1 in mice and Mamu-E in rhesus macaques, exists as a single polypeptide in association with 82-microglobulin. The polypeptide consists of three domains: the α1 and α2 domains can bind a diverse repertoire of antigenic peptides from nonamers up to 40 amino acid peptides in length. HLA-E exhibits only 2 allelic forms with a single amino acid difference (Arg 107 Gly), not affecting its peptide binding, and no polymorphism is noted in the human species (Joosten et al. 2016. J Immunol. Res. Article ID 2695396; Rodgers and Cook, 2005. Nat. Rev. Immunol. 5:459). As an MHC I somatic antigen, HLA-E is abundantly expressed on nearly all somatic cells and in all the lymphocytes, B-cells, CD4 and CD8 T cells, monocytes, and dendric cells (DC) (FIG. 4, this Invention).

Therefore, similar to the classical MHC I, HLA-E serves as a biomarker for degraded self peptides from all endogenous somatic self-proteins as well as decorated with non-self peptides, derived from foreign proteins from the infectious organisms. Peptide-bearing HLA-E on APC can induce HLA-E peptide-specific T cells for immunosurveillance of all somatic cells bearing HLA-E and peptides, including APCs and immunosurveilling T cells themselves. In addition to this traditional T cell receptors (TCR) and HLA-E-peptide interactions, HLA-E conformed by the peptides on all somatic cells also interact or communicate with CD94/NKG2 receptors on NK cells and T cells (Joosten et al. 2016. J Immunol. Res. Article ID 2695396).

Adaptive immunity antigenic peptide processing: Endogenous peptides of the autologous origins (autoantigens, inflammation-related antigens, cancer antigens), and the endogenously produced bacterial or viral proteins of the infectious origins, are processed and generated by the proteasomes, transported by transport-associated protein (TAP) TAP-1/TAP-2, and are loaded differentially onto the classical MHC I, HLA-A and HLA-B as well as the nonclassical HLA-E via a derlin-1-dependent ER translocator compartment (Bravo et al. 2013. Int. Rev. Cell Mol. Biol. 301:215). Signal peptides generated by the signal peptidase compartment, including HLA-A, -B, -C can also load onto HLA-E in a signal peptidase compartment. These two compartments can compete in loading antigenic peptides to HLA-E (Blum et al. 2013. Annu. Rev. Immunol. 31: 443). HLA-E like classical MHC I participate in self and non-self discrimination. There are estimated about 19,000-20,000 human endogenous self-proteins, each is synthesized in the ER and degraded via quality control mechanism to recycle/refold an aberrantly folded protein or making decision to rid of the aberrantly folded protein via an unfold protein response (UPR) accompanied by ER stress and degraded peptides.

Through this process, henceforth each somatic cell is self-marked by binding endogenously processed immunogenic or tolerogenic peptides onto the classical MHC I as well as non-classical MHC I such as Qa-1, Qa-2 in the rodents and HLA-E in the humans and can be extended to HLA-G and HLA-F (Rodgers et al. 2005. Nat. Rev. Immunol., 5: 459). Depending on the context of costimulation, it is envisioned that cytotoxic T lymphocytes (CTL) or effector T cells (Teff) to endogenous peptides bound to HLA-E are normally tolerized, and an immunoregulatory T cell (Treg) is favored, under a lower threshold of costimulation, while functional activated immunity is elicited and CTL and Teff are therefore induced via breaking tolerance to self and foreign antigenic peptides presented by HLA-E or other non-classical MHC I on inflammatory cells, tumor cells, and bacterial and viral infected cells, which are destined and targeted for destruction.

The two common human allelic phenotypes, HLA-E*01:01 (SEQ ID NO: 4, SEQ ID NO: 5) and HLA-E*01:03 (SEQ ID NO: 1, SEQ ID NO: 6) are functionally monomorphic, differing only by a single amino acid substitution (Arg or Gly) at position 107, situated on a loop outside the main peptide binding sites (Celik et al. 2016. 68:29). There are two major types of binding motifs between HLA-E and antigenic peptides. The canonical binding motif most studied by the investigators resides in its union with the evolutionarily conserved leader peptides of those processed from the HLA-E peptide binding pocket will fit the leader peptide sequences derived from HLA-A, -B, -C or -G molecules, at position 2 and 9 with position 3, 6 and 7 playing a lesser weight, while position 5 and 8 play an important role in interacting with CD94/NKG2A/C (Miller et al. 2003. J. Immunol. 171: 1369). The noncanonical binding motif permits the union of HLA-E binding pocket with conventional nominal antigenic peptides other than the leader peptides, e.g., HLA_A02.01 (Lampen et al., 2013, Mol. Immunol. 53:126-31). Peptides isolated from the HLA-E by affinity chromatography and sequences of peptides determined by MS/MS, reveal the key anchored residues similar to those of the classical HLA-A.02.01 haplotype. This constitutes a fair representation of the HLA-E binding motif, e.g., a weight of the VMAPRTLL (I/V/L)L motif for leader peptides vs that of a multiple of nominal peptide motifs.

We envision that following accommodating primary anchor residues, HLA-E-bound leader peptides from different MHC I as well as nominal antigenic peptides from all somatic and germ line antigens can adopt flexible conformations within the peptide binding sites, or the primary B and F pockets as well as other secondary pockets. This second type of binding motif to nominal antigenic peptides is important for self/nonself discrimination, e.g., self-peptide regulation as well as particularly important for making a universal peptide vaccine for an infectious disease microorganism. Hence, we propose that adaptive protective immunity against intracellular pathogens such as intracellular bacteria, intracellular protozoans, and intracellular viral infections can lead to peptides/HLA-E mediated sterile microbial immunity. We envision that because there exists no polymorphism of HLA-E, any bacterial or viral peptides presented by HLA-E can be universally applied to all human individuals for inducing CD8$^+$ T cells, cytotoxic or immunoregulatory, as well as CD4+ T cells with a higher affinity for peptide/HLA-E, compensating for the accessory interaction of CD8/α3 canonical interaction that recognize short pathogen-derived peptide epitopes or self-peptides as universal peptide vaccines. It is possible that protective immunity may exist in rhesus macaques, which exhibited HLA-E restricted CTL against peptides derived from simian immunodeficiency virus (HIV), decorated on HLA-E of viral infected cells (Hansen et al., 2016. Science, 351: 714).

As long as 15-meric synthetic peptides were employed to stimulate a recall viral peptide/HLA-E mediated CTL response. The length and feasibility of processing a 15-meric synthetic peptide is predicted by ER associated degradation (ERAD). According to MS/MS sequencing analyses, such HLA-E binding nominal peptides can be quite flexible up to a length of 25 to 40-mer from a diverse sequence repertoire of somatic antigens (Celik et al., 2016, Immunogenetics, 68: 29). Moreover, HLA-E can maintain a relatively stable conformation with/without β2 microglobulin and even in the absence of added peptides. We therefore propose that this state of structural conformability can support low-affinity peptide binding and peptide exchange, increasing versatility and diversity of peptide binding resulting in even to homologous or analogous peptide promiscuously, or deviant from the original binding sequences with some variation on top of its universal peptide binding status.

Thus, an embodiment of this invention is to identify such promiscuously, homologous across the species, e.g., rodents and rhesus macaques to translational clinical human trials, or analogous peptides based on the initial binding sequences for more potent HLA-E-restricted peptides. The embodiment will permit feasibility of animal model testing on a potentially druggable homologous peptide sequence, first tested in rodents, followed by rhesus macaques prior to translation in humans; and by a further genetic and protein engineering, HLA-E analogous therapeutic peptides can be rendered more potent by peptide scanning. In another type of immune recognition, the leader or nominal peptides-bound HLA-E on targets can guide CD94/NKG2A/C-mediated immune surveillance by NK or by bifunctional CTL expressing TCR as well as CD94/NKG2A/C.

Henceforth, the main embodiment of this invention is to vaccinate and to induce CD8+ CTL, CD8+ Treg, CD4+ Teff, and CD4 Treg by therapeutic HLA-E peptides presented by APC to effect on the primary targets: auto-reactive/-immune cells, inflammation-causing cells (e.g., IgE-producing B cells, TNF-α-producing synovial cells), and HLA/tumor peptides bearing cancers. Noteworthily, the above vaccinated and induced cells bear not only amplified HLA-A/peptide reactive TCR for recognition therapeutic purpose but also themselves can bear HLA-E/self or foreign peptides thus as a secondary target for being recognized. Thus, the HLA-E/therapeutic peptides-specific TCR system is coupled or integrated with an autochthonous HLA-E/peptides in a Predator/being Prey model of immune homeostasis. These envisioned HLA-E/peptide vaccines encompass a complete repertoire of nominal peptides and leader peptides, synthetically or recombinantly prepared or biologically processed from a complete repertoire of somatic antigenic peptides (of various lengths) via proteases/proteasome-based processing in the ER and the cytosol in both the antegrade and retrograde pathways. The various sources of peptides are finally loaded onto APC for immunity induction, or tolerance induction according to the levels of costimulation or co-tolerization. The embodiment of can be further manipulated or enhanced via interactions amongst NKG2A/C on the above vaccinated and induced immune cells with HLA-E (bound with nominal peptides or endogenous leader peptides, or empty) on and the therapeutic targets.

Regarding the size of the human proteome, approximately 19,000 to 20,000 proteins are encoded in the open reading frame (https://www.proteinatlas.org). In the embodiment of the invention, the degraded peptides of this proteome can be used as endogenously processed antigenic peptides for leader-like peptides or nominal HLA-E peptide binding, or a similar binding motif to that of HLA-A02.01 (Lampen, et al., 2013. Mol. Immunol. 53: 126) as well as other, HLA-A, HLA-B, or HLA-C haplotypes. This diverse repertoire of self-proteins synthesized in the ER. All proteins and polypeptides synthesized in the ER undergo 'conformational or folding editing' or dubbed a 'quality control (QC)'. A significant proportion of these proteins and peptides may not be properly glycosylated, or undergo correct folding and assembly process in the ER. As a result, the proteins and polypeptides are antegrade forward-moving transport out of the ER to the cytosol and undergo degradation by the cytosolic proteasomes. The quality control of a protein or polypeptide is necessary for removing dis-assembled products as toxic wastes. Importantly the degraded peptides then can be transported back and packaged along in a retrograde transport with either classical MHC I (HLA-A, -B, -C) or HLA-E, are necessary for presenting as a self-peptide as a marker or biomarker for aborting or inactivating an anti-self response, or cause suppression of an autoimmune responses to self or self-biomarker.

The processed peptides are candidates decorating HLA-E are candidate drugs for treating autoimmune diseases and used for cancer immunotherapy. Endogenously derived self-peptides from innate proteins are decorated on the cell surface by MHC class I molecules for immune surveillance for defending against bacterial and viral infected cells or transformed tumors or cancers. Immunogenic peptides are in general from 8 to 11-mers or longer peptides for further trimming, processed via the ER stress pathways. Peptides processed by the proteasomes are released into the cytosol, and then picked up the TAP ½ and retro-translocated in the ER, and further trimmed by the ER aminopeptidase (Townsend, et al., 1990. Cell, 62: 685). The resulting peptides with a length of 8-11 and loaded on MHC I in a final relay involve the peptide binding to the MHC I and β2m and transported to cell surface via the trans-Golgi network (TGN) network (Blum et al. 2013. Annu Rev. Immunol. 31:443).

Moreover, in the case of signal peptides, there is a large repertoire of the signal peptide sequences more than 13,000 different signal peptide documented in the signal peptide data base, which are all candidates for HLA-E binding in first type and second types of binding motifs (http://www.signalpeptide.de/). N-terminal signal sequences mediate targeting of nascent secretory and membrane proteins to the endoplasmic reticulum (ER) in a signal recognition particle (SRP)-dependent manner, which can occur in a specific signal peptidase compartment (Lemberg et al. 2001. J.I. 167: 6441). Signal sequences have a tripartite structure, consisting of a hydrophobic core region (h-region) flanked by an N- and C-terminal region. The latter contains the signal peptide peptidase (SPase) consensus cleavage site. For example, classical HLA-A, -B, -C, and -G are expressed with a typical signal sequence for targeting to the membrane expression TGN network pathway, wherein the signal sequences are presented onto membrane surface nonclassical MHC class I molecule, HLA-E for CTL-mediated as well as NK cell-mediated immune surveillance.

Thus, the signal peptide sequences are cut off co-translationally from a repertoire of pre-proteins, or pre-polypeptides by signal peptidase, whereafter cleaved signal peptides from these substrates (including classical MHC I) span the ER membrane at their central hydrophobic region, with the N terminus facing the cytosol. Consequently, the liberated signal peptides in the cytosol are released into by SPase, reloaded back unto HLA-E via TAP transporter for HLA-E cell surface expression. Alternatively, signal peptides remain membrane-inserted and can be part of a protein complex, while other signal peptides are released as such from the ER membrane (Lemberg et al. 2001. J. I. 167: 6441).

Hence, this large peptide space encompassing all the proteins and polypeptides, serves as a potential source of HLA-E based self-peptides for CTL and Treg. Signal sequences of human classical MHC I molecules are a unique source of epitopes for newly synthesized nonclassical HLA-E molecules. Binding of such conserved peptides to HLA-E induces its cell surface expression, which engage CD94/NKG2A on NK cells and suppress NK-mediated target killing (Joosten et al 2016 J. Immunol. Res. Article #2695396). After cleavage from the pre-proteins/polypeptides, the liberated MHC class I signal peptide (s) in particular, is further processed by signal peptide peptidase in the hydrophobic, membrane-spanning region. This editing is essential for the release of the HLA-E epitope-containing fragment from the lipid bilayer and its subsequent transport into the ER lumen via the TAP (Lemberg et al. 2001 J.I. 167: 6441). Thus, in the embodiment of this invention for clinically useful HLA-E binding therapeutic peptides, three types of therapeutic peptides are claimed: the high protease processivity of the signal peptides include the first kind of canonical (VMAPRTIL) binding motif (type A) as well as the second kind of nominal binding motif, which can maintain a certain anchor residue (s) with others being highly flexible among the nonamers (type B) or such nonamer-binding motif in a longer peptide binding to be further edited by ER proteases and proteasomes (type B contained within) (Celik et al., 2016. Immunogenetics, 68: 29).

Thus, in all the type A and type B binding of peptides to HLA-E, whereby a peptide capable of binding to HLA-E can be a candidate as a universal peptide vaccine for the purpose for immune defense and/or desensitizing an autoimmune-mediated inflammation. In distinct contrast to HLA-E binding in our evaluation, a diverse spectrum of microbial antigenic peptides is presented by highly polymorphic major histocompatibility complex class Ia (MHC-Ia) molecules on the surface of infected cells, of which the peptides restricted to a particular haplotype cannot bind a different haplotype. MHC-Ia allomorphs vary considerably in their peptide-binding properties, and therefore the particular pathogen-derived peptides targeted by pathogen-specific CD8+ T cells is potentially useful for serving as a vaccine for only those haplotypes but not others hence the peptides are not universally useful. Consequently, the epitopes recognized by CD8+ T cells responding to the same pathogen are highly diverse across different individuals, resulting in heterogeneity among individuals in their ability to clear or control various microbial infections—in particular, agents such as HIV with a high intrinsic capacity for mutational immune escape. Such variation can be prohibitively costly for making numerous classical MHC I haplotype-specific vaccines. Thus, in contrast, the embodiment of the invention resides in the singular effort to render a universal peptide vaccine based on its binding to a single invariant HLA-E, e.g., HLA-E-mediated CD8+ T cells, permitting universal protective immune responses.

Immune evasion of viral infection frequently involves compromising the classical MHC I mediated CTL pathways by degrading faster classical MHCI via specific viral encoded protein such as US11, and US2 in human cytomegalovirus (HCMV) infection (Lilley and Ploegh, 2004. Nature, 429: 834); or by abrogating the TAP½ dependent retro-transporting back the proteasome-released peptides unto the MHC I for vial peptide marking of the infected cells (Verweij, 2015. PLOS Pathogens |DOI:10.1371/1004743); henceforth removal of infected targets by the CTL. Having compromised the classical MHC I-mediated pathway, by rendering viral infected targets naked for surface classical MHC I due to rapid degradation in the ER, HLA-E antigen presenting pathway can be differentially affected in CMV-infected cells. HLA-E presenting pathway can be different from the classical MHC I (HLA-A, -B, -C) pathways in that (i) degradation of MHC I permits high levels of signal peptides to augment HLA-E expression; (ii) US11/US2 mediated degradation of HLA-A, -B, -C, can facilitate the availability of nominal peptides, (including signal peptides mentioned above) readily available, easing peptide competition, to the alternative HLA-E peptide loading for immune surveillance via HLA-E/CTL pathway; (iii) high levels of HLA-E and peptides can induce CD94/NKG2C-mediated NK-mediated or bifunctional CTL/NK-mediated killing of the infected cells or autoreactive cells, abrogating NK cell tolerance due to low level engagement of HLA-E with self-leader peptides. Thus, the novelty and the embodiment of the invention is to use HLA-E universal vaccines to protect virus-induced diseases particularly in infected individuals wherein viral infections causes immune evasion to sabotage classical MHC I via US11/US2 like molecule to augment Derlin-1 mediated translocation to the proteasomal compartments.

Signal sequences-derived peptides from the endogenous proteins can be directly released into the ER by the signal peptidase (SPase) complex without participation of the proteasomes and TAP½ pathways (Lemberg et al. 2001. J.I. 167: 6441). Viral induced immune evasion by Herpes simplex virus (HSV) and HCMV, consists of means to abrogate TAP function, which compromise processing of cytosolic viral peptides processed via proteasomes and loaded onto classical MHC I (Verweij et al. 2015. PLOS Pathogens DOI:10.1371/journal). This highlights the central role of HLA-E in viral mediated immune surveillance. On the other hand, TAP is deleted in the tumors, which correlated with poor prognosis and health. The embodiment of the invention also includes classical MHC 1 as well as nonclassical MHC 1 dual-binding antigenic peptides.

HLA-E binds majorly to leader peptide sequences of classical MHC I molecules but can exhibit an altered nominal peptide binding similar to classical MHC I, including HLA-A0201. Normally HLA-E utilizing positions 2, and 9 for deeper contact/binding, and the positions 3 and 6 for shallower binding (O' Callaghan et al. 1998. Mol. Cell 1: 531; Miller et al. 2003. J.I. 171: 1369), inferring that the nominal peptide pool and signal peptide pool mutually compete. The rule of multiple position of peptide binding to HLA-E dictates that under the context of diverse endogenous peptide generation and processing in addition to leader peptides, HLA-E can alternatively or nominally interact nominal antigenic peptides at positions 2 and 9 for pockets B and F respectively, and the main anchors are modulated by the position 3 and 6, and position 1, 4, 5, 7, 8 positions for adapting the shallow pockets of HLA-E, yielding high affinity binding to HLA-E to expand the nominal T cell repertoire, whilst disengaging from binding to NKG2A/C, e.g., as conventional CTL, or engaging with NKG2A/C as bifunctional NK/CTL or Treg. This flexibility of the "flip-flop" adaptive binding for a diversity of nominal antigenic peptides accommodated in the HLA-E binding sites is similar to that of classical MHC I peptide binding; and the versatility or availability of antigenic peptides can be due to cellular nutritional status, infections, and cancerous transformations, and other diseased inflammatory conditions, or states of the metabolic syndromes in different organs, including the immune system, liver, pancreas, heart and adipose tissues. Notably, the embodiment of the invention dictates a mono-functional CTL function, while position 1, 4, 5, 7, and 8 engaging the binding interface between TCR and HLA-E, or bifunctional CTL or Treg and NK effector functions, when position 1, 4, 5, 7, 8 engage with CD94/NKG2A/C.

HLA-G (SEQ ID NO:12, SEQ ID NO: 13, SEQ ID: 14, SEQ ID NO: 15, SEQ ID NO: 16, SEQ ID NO: 17):

The HLA-G gene is located on chromosome 6p21.3, comprising eight exons, wherein HLA-G*01:01 is the most common isoform with four membrane-bound (HLA-G1-G4) and three (HLA-G5-G7) soluble isoforms e.g., HLA-G5 to -G7, and one shed HLA-G1, generated by a stop codon after exon 4 (HLA-G5) or by cleaving of HLA-G1 as soluble HLA-G1 by metalloproteinases. HLA-G2 and HLA-G6 bind to ILT4 through their α3 domain, while engaging alternatively ILT2 via β2m. Like HLA-E, HLA-G can also present selected signal sequences of other HLA molecules (Lin and Yan. 2015. Mol. Med. 21:782). HLA-G can also present the nominal peptide presenter like HLA-Ia molecules with a restricted peptide repertoire to the tissue distribution and cell type by mass spectrometric sequencing. Notably, HLA-G*01:04, HLA-G*01:03 and HLA-G*01:01 differ from each other by a single amino acid outside the peptide-binding pocket, the diversity of peptide bound are different (Celik et al. 2018. Immunogenetics. 70: 485). Thus HLA-G as well as HLA-E can serve as non-classical MHC I universal antigenic peptide presenter and vaccine.

As a niche, HLA-G expression is restricted under physiological conditions to immune privileged sites, indicating a suppressive function for maintaining tissue integrity, HLA-G/self-peptide tolerance or signaling exonerates the targets from immune destruction, e.g., that expressed on erythroid precursors, endothelia precursors, cornea, thymic medulla and pancreatic islets on normal circumstances; in particular, in placenta with cytotrophoblasts as the unique cell types expressing surface HLA-G1, while secreting soluble HLA-G5 for maternal-fetal tolerance induction (Lin and Yan. 2015. Mol. Med. 21:782), or conditions of manipulating tissue or organ transplants from autoimmune or transplantation attack; alternatively, on HLA-G in pathological conditions on cancers, and viral infected cells for immune evasion and sustaining the pathological lesion.

Reciprocal interactions amongst HLA-G and the leucocyte immunoglobulin-like receptors subfamily members (LILRs), or immunoglobulin-like T cell (ILT1-4), KIR2DL4 of effector (NK, T, APC) and target cells can send immunoregulatory suppressive signals. Thus, HLA-G5 induces in ILT4+ (LILRB2) dendritic cells (DCs) to induce IL-10 secreting Tr1 and Tregs (CD4+ CD25highFOXP3+) (LeMoualt et al. 2005. FASEB J. 19: 662). HLA-G-restricted CD8 T cells play a role in suppressive immunoregulation. Interaction with HLA-G leads commonly to an inhibition of the interacting immune effector cells. Those interactions are mediated through inhibiting receptors like KIR2DL4 and ILT2 (LILRB1) on NK cells, ILT2 on T cells, ILT4 on macrophages and ILT4 on dendritic cells.

Thus, the embodiment of the invention is to induce HLA-G+ CD8 CTL or Treg with universal endogenous and foreign antigenic peptides, against targets displaying HLA-G restricted peptides; furthermore, the suppressive effector functions of CTL or Treg be doubled up with surface expression of HLA-G by means of modulators, including nuclear receptor agonists and antagonists.

HLA-F (SEQ ID NO: 8, SEQ ID NO: 9, SEQ ID NO: 10, SEQ ID NO: 11):

The embodiment of the invention extends to another nonclassical MHCI: HLA-F regarding universal HLA-F-restricted CTL for microbial infections and autochthonous tumors, and Treg-mediated self or autoantigenic peptides as universal Treg vaccines due to its limited and manageable allelic polymorphism like that of HLA-E and HLA-G for a feasible universal vaccine epitope of wide human population coverage. HLA-F heavy chain with β2m forms a 40-41 kDa protein, dependent on its truncated cytoplasmic tail for export from the ER by a C-terminal valine, governed by the coat complex (COP) II, moreover an RxR motif interact with 14-3-3 proteins for anterograde transport. This freedom of movement plays a modulatory role in antigenic peptide loading via TAP½ (Boyle et al. 2006. J.I. 176: 6474).

HLA-F encodes only five proteins (HLA-F*01:01, F*01:02, F*01:03, F*01:04, F*01:05) differing in only five of the ten variant amino acids located in the α1 peptide binding domains of HLA-E (Robinson et al. 2015. Nuc. Acid. Res. 43 (Database issue) D423-D431). Thus, we propose that a limited binding spectrum, restricted to five or less isoforms for an overlapping shared vaccine epitope, or not more than five vaccine epitope to cover the entire human population. In addition, the variant amino acids close the A binding pocket of peptide-binding site, and such hindrance permits binding of peptides of 7 to large than 30 amino acid peptides in length subject to molecular trimming or editing, presented and operated on this closed HLA-F conformer (Dulberger et al. 2017. Immunity. 46: 1018). HLA-F exhibits intracellular expression in monocytes, B cells, T cells and NK cells, as well as cell surface expression of activated lymphocytes, trophoblasts, suggesting an immunosurveillance function and in maternal-fetal implant tolerance. Thus, an embodiment of invention is to employ nonclassical MHC Ib, e.g., HLA-F-restricted endogenous or foreign peptides as universal vaccines for inducing CD8 CTL or Treg, or inducing CD4 Treg to eliminate microbial infections, or autochthonous cancers, or suppressing autoimmune attack in particular tissues and organs.

Notably, as an open conformer (OC), HLA-F is not associated with β2m and peptides, which interacts with the killer cell immunoglobulin-like NK receptor, NKRs (KIR) KIR3DL2, KIR3DS4 and KIR3DS1 against HIV-infected targets (Kiani et al., J.I., 2018. 201:113). In contrast, peptide-bound, β2m-associated closed HLA-F conformer interacts with afore-mentioned HLA-F-restricted TCR, and in addition also interacts with ILT2 and ILT4 for sending suppressive or cytotoxic signals to the targets. HLA-F has been detected immunohistochemically in various cancers, i.e., non-small cell lung cancer (NSCLC), esophageal squamous cell carcinoma, gastric adenocarcinoma and breast cancers, associated with a poor prognosis, and an invasive phenotype. An embodiment of the invention is to harness bifunctional attack of tumor cells via CTL induction to HLA-F-tumor peptides or autoimmunity-attack-causal peptides, presented by the closed conformation of HLA-F as well as upregulate NKRs to exert NK-mediated killing or suppression of the targets along via KIRs.

Enhanced MHC Ib Antigenic Peptide Loading:

One embodiment is to employ means to block the loading of antigenic peptides to classical MHC I at the levels of antigen-presenting cells (APC), and divert such peptides and enables their binding and loading preferentially to HLA-E, which exists in two allelic forms with a single amino acid difference on a non-critical, non-peptide binding region. Thus, the embodiment of the invention is to load the antigenic peptides of medical and therapeutic importance onto the non-polymorphic HLA-E peptide binding sites, as a universal vaccine, bypassing the major classical MHC I pathways in order to treat infectious diseases, autoimmune diseases, allergy, inflammatory diseases, and cancers.

Conventionally, a unique antigenic peptide binds to a unique classical MHC I allelic product, e.g., a unique peptide out of a multiplicity of therapeutic peptides from a given therapeutic protein via proteasomes, retro-translocated via TAP-1/TAP-2, and then binds to one of the highly polymorphic classical MHC I (more than 1,000 haplotypes of HLA-A vs. HLA-B, IPD-IMGT/HLA, version 3.33.0). Derlin-1 (gene: Derl-1, SEQ ID NO: 85, SEQ ID NO: 86), a homolog of yeast Der-1 is a central critical compartment for accommodating misfolded classical MHC I in an retrograde transport to cytosol for proteasomal degradation, and viral products such as US11 and US2 piggyback on Derlin-1 to accelerate export of classical MHC I for ubiquitin-mediated proteasome-dependent degradation. Thus, an embodiment of the invention is to augment HLA-E peptide presentation of nominal antigenic peptides by abrogating the production of leader peptides of MHC I, and other MHC I peptides fragments via Derlin-1 blockage, hence reducing the pressure of self-leader peptides vs the HLA-E-restricted therapeutic nominal peptides.

Therapeutic Modalities:

From the innate self-tolerance and breaking tolerance vintage, immune-therapeutics and universal vaccines, can be designed if the critical protein(s) involved in the inflammatory or cancerous pathways are identified. The peptides of these given proteins, which are bound to HLA-E so that the CTL-mediated immunity can be elicited against the endogenously processed and presented nominal antigenic peptides on the autologous cellular targets in order to downregulate autoimmunity and/or cancers. The embodiment of this invention dictates a universal inflammation or cancer vaccine through a union of the chosen, one or more clinically useful peptide (s) (among a repertoire of the universal therapeutic proteins with the HLA-E motif) to the invariant HLA-E, and loading facilitated by enhancement method to abrogate the Delin-1 compartment.

The breaking of tolerance to these self-peptides can be achieved by providing necessary costimulatory stimulation, detailed in the Examples. In contrast, foreign proteins encoding foreign HLA-E-restricted peptides stimulate non-tolerant HLA-E foreign peptides-specific CD8 T-cells without or with only low levels of T cell costimulation, while full costimulation will be provided for maximal efficacies. The embodiment of the invention exhibit four-fold modality: (i) In one modality, HLA-E and peptide-specific cytotoxic 'T lymphocytes (CTL), elicited upon vaccination of HLA-E bound peptides of autochthonous origin, eliminate cancer cells expressing HLA-E bound endogenous cancer peptide antigens; (ii) In another modality, HLA-E and peptide-specific cytotoxic T lymphocytes (CTL), elicited upon vaccination of HLA-E bound peptides of the infectious origins, eliminate the sources of infectious depots. (iii) In another novel modality, such CTL can eliminate inflammatory cells, exhibiting an antigenic peptide of an inflammatory molecule, associated with HLA-E present on the disease-causing tissues. (iv) In yet another modality, HLA-E bound peptide vaccines cause production of HLA-E and peptide-restricted, immune-regulatory T cells (Treg), or in the form of autoimmune peptide-tolerized, or anergic cells to dampen effector or inflammatory CD4 T cells, CD8 T cells, or suppress tissue-damaging autoantibody-producing B cells or plasma cells, expressing cell surface HLA-E bound peptides.

At the APC levels, the embodiment is to induce peptide and HLA-E specific CD8+ CTL or CD4 and CD8 Treg directly via the nonclassical HLA-E based peptide presenting pathway in the presence of a normal classical MHC I pathway, or in the presence of deviated/suppressed classical MHC I pathway at levels of antigen presenting cells such as dendritic cells, B cells, macrophages, and other facultative APC such as mast cells, Langerhans cells (LC), skeletal muscle cells (SMC), and keratinocytes. A deviated modality of peptide/HLA-E presentation is via a DNA vaccine construct expressing US11 and US2 proteins, which knock down HLA-A and -B mediated peptide presentation in favor of that mediated via HLA-E in the above APC. DNA vaccine can be introduced via an intradermal needle or a needle grid, a tattoo gun, or skin patch, impacting keratinocytes, LCs, DCs and other APCs in the dermis and epidermis. Alternatively, the vaccine can be introduced into SMC via electroporation (EP), or intramuscular (im) injection in muscle relaxant-treated SMC. Another modality is via peptides and HLA-E in saline or liposomes in the context of co-stimulation. Another modality is via peptides and HLA-E delivered via heat shock protein, HSP70, HSP90, Gp 96/GRP 94, GRP 76, calnexin, and calreticulin. Another modality is to load peptides onto HLA-E on APC treated with proteasome inhibitors, and small molecule metabolic inhibitors, siRNA/shRNA to the Delin-1 compartment, which abrogates the classical MHC I loading, and critically inhibits the generation of MHC I leader peptides, which compete for pocket B and pocket F of HLA-E, hence facilitating nominal peptide loading onto the HLA-E compartment of available binding pockets with flexibility.

The inflammatory diseases comprise and are not limited to airway inflammation, allergic asthma, coronary heart diseases (CHD), heart-failure, Alzheimer's disease, chronic kidney fibrosis, idiopathic pulmonary fibrosis (IPF), and COPD. The infectious diseases comprise bacterial and viral infectious microorganisms. The autoimmune diseases comprise and not limited to rheumatoid arthritis, MS, type 1 diabetes, thyroiditis. Cancers comprise but not limited to NSCLC, SCLC, RCC, melanomas, myelomas, leukemia, lymphomas, sarcomas, breast and ovarian cancers, gliomas.

Example 1: Identification of HLA-E Expression by Incubating with HLA-E Predicted Peptides Surface expression of HLA-E or HLA-G can be induced by retinoid X receptor (RXRα) agonist or Interferon 13.

HLA-E and HLA-G share the same ability to interact with NK cell receptor as well as TCRs regulating both innate and adaptive immunity. However, unlike classic MHC molecules widely expressed in tissues, non-classical MHC, HLA-E and HLA-G are characteristic of their limited polymorphism and low cell surface expression. Enhancement of expression of HLA-E and G is pivotal for non-classic MHC to regulate immunity. Bexarotene and interferon-β were used as anti-cancer or anti-viral agents. (1) Thus, importantly, RXRa agonist, SR11237 and bexarotene dramatically induced HLA-E expression of immature MoDC cells over a three-log intensity. However, they had little or no effect on HLA-G expression. Interferon β had a similar effect, increasing intense expression of HLA-E but not that HLA-G on immature MoDCs (FIG. 1). Therefore, an embodiment of the invention is to augment HLA-E-mediated peptide presentation to achieve a curative effect for infectious diseases, inflammatory diseases, autoimmune diseases, or cancers by treating with interferon β or other cytokines in a regimen. At levels of PBMCs, expression, interferon β increased expression of HLA-G about two-fold in $CD4^+$ T cells as well as in $CD8^+$ T cells (FIG. 2A) but decrease HLA-E expression in these cells (FIG. 2B). Moreover, Interferon β increased both HLA-E and HLA-G expression in $CD19^+$ cells. HLA-G plays an important role in downregulating immunity and inflammation. Immunoregulatory effector and target cells can mutually express HLA-G as well as ILT-1, 2, 3, 4 on cell surface, promoting a bilateral and bipartisan HLA-G/ILT-x interactive bridges amongst CD4/CD4; CD8/CD8; CD4/CD8; CD4/B cell; CD8/B cell. An embodiment of the invention is to augment the immunoregulatory efficacies of CD4 and CD8 T cells, and CD19 B cells, serving reciprocally as immunoregulatory cells and targets for manipulation for a curative effect for infectious diseases, cancers, and alleviating inflammatory diseases and autoimmune diseases.

Peptides-Pulsed MoDC Induces HLA-G Expression of CD8+ T Cells.

Nonclassical HLA-G is mainly expressed in the fetal tissues maintaining immune tolerance, and also expressed in dendritic cells, B cells and CD4 T cells and CD8 T cells, as universal targets due to limited polymorphism. In the embodiment of this invention, a cooperation between non-classical MHC I and classical MHCI can increase the range of immunosuppression. The embodiment dictates that non-classical HLA-G concomitantly co-expressed on nominal antigenic peptides/classical MHC I-restricted cell types, e.g., CD8 or CD4 single or CD4/CD8 double positive cells in serving the immunoregulatory T cells utilizing both TCR-mediated repertoire as well as HLA-G/ILT-x pathways, in particular HLA-G5 can engage ILT4 on dendritic cells to stimulate IL-10, and induce Treg (Selmani et al., 2008. Stem Cell, 26: 212).

In the embodiment, we demonstrate the feasibility to induce a centrally important HLA-A2.01 peptide induced we showed that, after pulsed with IgE epitope A2 peptide-induced CD8 T-cell bearing the immunoregulatory HLA-G positive phenotype stimulated by nuclear receptor agonist, SR11237, both immature and mature MoDC induce significant amount of HLA G expression in CD8+ T cells. But no further increase was observed after treatment of SR11237 (FIG. 3). Similarly, open conformer HLA-F can be upregulated via such types of modulators and act as a hammerhead to transmit suppressive signal via KIRx/HLA-F (open conformer) onto a NK; alternatively, CTL/Treg can recognize target via TCR/HLA-F-peptides (closed conformer). Furthermore, the state of the cells permits dual recognition in that a bifunctional CTL/Treg with HLA-F open conformer hammerhead can recruit NK cells via KIRx, as well as target closed HLA-F-peptides on targets, which maximize target lysis or suppression via CTL/Treg/NK clustering activities.

Attempt to Identify IgE Epitope HLA-E Binding Peptide by T 2 Cells.

The mutant human cell line T2, defective in antigen presentation in the context of MHC I, exhibits low levels of surface MHC I expression, but high levels of surface expression after binding to MHC I-restricted peptides (Lorente et al. 2011. J.B.C. 286:38054). HLA-E displays the same characteristic as MHC I and its surface expression in T2 cells is TAP½- and tapasin-dependent and is correlated with binding of HLA-E to its peptides providing approach to screen the peptide that can bind to HLA-E. Herein, we showed that A 2 leader peptide (predicted by the IEBD and MHCPan4.0 Programs) enhanced surface expression after treatment of T2 cells with peptide overnight incubation indicating it can bind and enhance HLA-E expression. However, B3 to B5 have no effect on surface expression of HLA-E in T 2 cells (FIG. 4). In contrast, IgE peptide E33 (TMTLPATTL, SEQ ID NO: 68) predicted by Ige Predict, the proprietary program developed by this Inventor and explained in the Example 2 exerted a stronger upregulation of HLA-E compared to the canonical A2 leader peptide (FIG. 12); moreover, two analogous and heteroclitic peptides: SEQ ID NO: 71 and SEQ ID NO: 77 generated from the E33 exhibited a higher predicted binding score, among others in Panel B showing comparable scores. Furthermore, a list of good HLA-E restricted IgE binders was shown in Panel C (SEQ ID NO: 18 to SEQ ID NO: 42).

Construction of Fusion Protein of HLA E and β2Microglobin.

HLA-E molecules loaded with signal sequence-derive peptides can also engage the inhibitory NKG2A and protect targets from NK-mediated lysis, while peptide-processing, loading, presentation of the same leader or nominal peptide can notwithstanding induce CTL that directly recognize and lyses target cells. HLA-E forms heterodimer with β2 microglobulin in order to be stabilized on cell surface, contribute to binding to signal peptides. In this study, we have successfully used pET recombinant system to make fusion protein, HLA-E and β2 microglobulin (β2m). Truncated HLA-E containing only α1, α2 and α3 domains fused with β2 microglobulin, was cloned, expressed in *E coli*. FIG. 5A showed that vector, pET-HLA-E-β2m was digested by Bam H I and Hind III confirming fusion of HLA-E and β2 m was cloned into pET vector. FIG. 5B showed that fusion protein of HLA-E-β2m was detected by western blotting with anti HLA-E or anti-β2m antibody; in comparison, β2 m was detected only by anti-β2 m antibody.

Biological and chemical systems are designed for characterizing and assaying HLA-E binding/-restricted peptides. In an embodiment of the invention to uncover nominal HLA-E nominal antigenic peptides, HLA-I negative K562 cells and 0.221 cells (Strong, 2003, JBC., 278:5082) are used for transfection with HLA-E*0101, and/or HLA-E*0103, and along a human $β_2$m construct. Because of the lack of endogenously processed classical MHC I processed peptides, the HLA-E transfected cells can be used for screening, purification and evaluating a repertoire of endogenous peptides loaded and bound to HLA-E. Natural HLA-E/β2m with the loaded endogenous peptides, as canonical leader-like peptides or nominal, noncanonical non-leader-like peptides bound to contours varying from that to the orthodox leader peptide focal of spread, can be included in and purified via anti-HLA-E antibody-bound affinity column, or size exclusion and by ion exchange chromatography, and wherein the peptides are eluted from the HLA-E, and subjected to the tandem mass spectrometry (MS/MS) peptide sequencing at pico- to femto-mole quantity. Notably, the sequence repertoire or universe is HLA-E restricted, which can be stored in a database, feeding into, analyzed by the in-house proprietary Igepredict Program, since K562 as well as 0.221 are devoid of classical MHC I (HLA-I), e.g., HLA-A, -B, -C.

The embodiment of this invention is to use this additional knowledge base or database to train and enhance the algorithm of pythonanywhere_Igepredict, a proprietary licensing software (Example 2). In another embodiment of the invention, the endogenous and natural sequences of the endogenous protein and exogenous proteins of infectious microbial origins, can be used as a drug API as an approximation to the self-peptides relevant for treating autoimmune diseases, inflammatory diseases, infectious diseases, and cancers.

The following antibodies are used for characterization: anti-HLA-A/B/C (clone W6/32), and anti-HLA-E (clone 3D12) and anti-HLA-A2 (clone BB7.2). Normal and TAP½ deficient T-2 cells and TAP½ deficient rodent RMA-S cells (Ossevoort et al. 1993. Eur. J. I. 23: 3082), transfected with HLA_A2.01_Kb cells in the laboratory, and HLA-E01.01 or 01.03 transfected 0.221 and K562 are used for the binding studies. Upregulation of HLA-E is studied in HLA-E binding studies using leader sequence like canonical leader peptides or nominal peptides resembling binding to classical MHC I, using the in-house developed program (http://ige.pythonanywhere.com/dashboard, (Example 2), The upregulated surface HLA-E of treated cells can then be measured by a commercial FACS machines and software, and data can be analyzed with FlowJo software (Tree star, Inc). To accumulate more HLA-E via the trans-Golgi network (TGN), cells can be incubated with 10 μM brefeldin A (BFA, and 200 nM bafilomycin-A1 (*Streptomyces griseus*) for the augmented surface expression of HLA-E.

Normal T-2 cells or reverted without TAP½ defects can also be used for identifying the strong HLA-E binding peptide (s). Under the normal condition, surface HLA-E is expressed at high levels, and the levels of expression can be further augmented with incubation with the leader peptides from HLA-E. Under this condition, the nonameric peptides predicted to exhibit the binding motif may not exhibit a further enhancement of the surface HLA-E expression, since endogenous HLA-A2.02.01 leader peptide, generated from proteasome pathway as well as the ER pathway can bind to HLA-E, minimally assisted by the exogenously added HLA-E binding peptides, with regards to its surface expression. Surface expressed HLA-E US11 (SEQ ID NO:87, SEQ ID NO: 88) and US2 (SEQ ID NO: 89, SEQ ID NO: 90) are HCMV proteins that decrease classical MHC I, e.g., HLA-A2.01 and HLA-B7.02. To evaluate whether US11 can also diminish HLA-E, thus damaging both HLA-E-restricted viral peptide presentation and CTL induction as a viral contrivance in an HLA-E constitutively activated cell lines. T2 cells were then stably transfected with pCDNA3.1 expressing US11. FIG. 5 showed importantly that US11 impressively knock-downed expression of HLA-A2, -B7 expression, embodying the vaccine strategy to augment HLA-E nominal antigenic peptide presentation by APC (e.g., T2 cells, a fusion of B and T leukemic cells, expressing high levels of CD86 and CD40 with APC efficacies comparable to normal MoDCs observed in IGE lab facility), depleted of classical MHC I by US11/US2.

Thus, one embodiment of this invention is to employ US11-transfected TAP½ deficient T2 with downregulated MHC I, e.g., HLA-A, -B, -C for screening and evaluating for HLA-E binding peptides via augmented surface HLA-E expression by depriving competitor HLA-A, -B, -C pathways as well as preventing generation of HLA-A, -B, -C leader peptides, which should sabotage the loading HLA-E binding nominal peptides.

Example 2: Construct Algorithms Based on Python Programs in Predicting the HLA-E Canonical Motifs A python program is written using a training set of data, which contains 8-11-meric peptides exhibiting binding to HLA-E, and exhibiting binding, weighted toward the conventional HLA-A. -B, -C leader peptide motifs, while the test sets consist of 8-11-mers amino acid peptide walks of designated protein candidates. The probability is calculated upon testing 2-mer and increased by one more residue at a given time for testing the probability of binding in order to consummate the re-iterative rounds of testing, and a score was assigned for each existing test sequence. The algorithm is presented as follows: A web site to propagate this service to the nonclassical MHC I, HLA-E, -F, -G community was made available by presenting the constructed website (http://ige.pythonanywhere.com) for licensable use.

IGE Predict:

Function of the Script.

The script for predicting binding scores consists of two functions, the long sequence parsing and short sequence score prediction. Those two functions will be discussed in the following paragraph. The IgE short sequence (9-mer) prediction script takes in 1 nonamer input and breaks it down to its n-grams. Then, according to our pre-trained weight, it will add up the score for each of its local components. For example, Assume in the trained model, the following information is learned: {VM:1, LL:3, AB:−1, DD:−3} (VM, LL, AB, DD) are patterns found and the number behind them are weighted. Then, for each sequence input, the script breaks the input sequence down, and check if any of these combinations match the pattern in pre-trained weight. It would add all the weight of found pattern together. By doing this, a score that denotes the binding probability of these sequences would be computed. Next, the long sequence parsing tool will take in a long sequence (e.g., IgE heavy chain, CHε1-CHε4 sequence) and use window slides to break them down to 9-mers. Step 1: select and start with the first character, and then include 8 characters that follow in that a new sequence of 9 characters form the script; Step 2: Move forward and for each position the script would repeat what we did in step 1 and then parse the long sequence to shorter subsequences; Step 3: Fit in parsed sequence into the program for binding score for each of the parsed sequences.

SVM (Support Vector Machine) and other machine learning networks (such as convolutional neural network and deep neural network) are tested as possible candidates. However, due to the amount of data presented, significant progress in accuracy could not be made. SVM model would returns a result with low accuracy because the input data set is small and random. As a result, SVM model would make an arbitrary prediction, and this leads to low accuracy. In addition to that, due to the heavy imbalance presented in the data set, the prediction result is heavily biased which is also an explanation for the initial low accuracy. Next the input is fitted with some pre-trained neural network, such as CNN (convolutional neural network). Deep learning framework Keras (an open source of neural network written in Python) is tested to build a neural net with two convolutional 2D layer and two fully connected layers. However, this approach showed an overfitted result. Although training set is associated with a very high predict accuracy, the test set showed limited accuracy. The reason is that a large training set could not be found to prevent model getting train set overfit. This kind of model would have good behavior on the training set; however, is variable upon new data feed.

Training Method.

Train set comes from the experiment results, with a nonamer peptide sequence and its binding rate. The whole train set consist of 69 peptides. Pre-trained weight: The script goes through all the sequences in a data set, separate the dataset with binding peptides and non-bind peptides, based on the binding rate. Each sequence in the training set is parsed into small pieces, and based on their binding score, a weight is assigned, which is then added to the cumulative weight for each identical sub-sequence, stored in a dictionary. For example, if a sequence is found in a non-binding peptide, a weight of (−1*normalized binding probability) is given. On the other hand, if a binding peptide sub-sequence is found, a weight of (1*normalized binding probability) is assigned to itself. After the weight is assigned, it is added to the cumulative weight for this sub-sequence. Statically, this entails predicting the likelihood of a peptide sequence binding to the HLA-E. After going through the training set, a dictionary of sub-sequence weights can be computed, and they can be utilized in the prediction model. To continually improve the train set, which plays a pivotal role in precision prediction of HLA-E based vaccine candidate from a test set. Thus an embodiment of this invention is to continually explore and use this additional information of knowledge base database of HLA-E purified, nominal antigenic peptides pools from 8-25-mer, including nonamer from the HLA-E transfected 0.221 cell line by this inventor and scantily published literatures, or data mined from available resources, as well as other 0.221 cell lines, transfected with HLA-E co-transfected with HLA-A, -B, -C. in order to continually train and enhance the algorithm of pythonanywhere_Igepredict, a proprietary licensing software program.

Using the pre-trained weight: For each input peptides, a scan is performed, and all the possible sub-sequences are extracted. Then, for each subsequence, the script would locate the weight in the prediction model and add them to the cumulative binding score. After performing the look up for each subsequence, the binding score will be output. The higher the binding score, the more likely it shall bind.

Test Method.

Algorithm II was established following the cumulative score assignment according to a training method or training methods in arrays. Initially, the finalized algorithm verified prediction result with the popular theory that most of the binding peptides possess a specific pattern, or motif called 'VMAPRTLLL (SEQ ID NO: 51)'. It verified the test result with this pattern and discovered that most of the results align with this pattern on position 1, 3, 6, 7, 9. These are key positions to determine whether this peptide will bind. Next, the finalized algorithm also verified the results against confirmed binding peptides list. Confirmed binding peptides are read, fitted in as an aptamer with pre-trained weight and a bind score is calculated. The score is much higher than random sequence. In addition, some confirmed unbinding peptides were also fed into this algorithm, the result is a large negative number. Finally, IgE heavy chain is used as an input, and sub-sequence with high binding score from this long sequence are computed. The script successfully parses the heavy chain and assigns binding score for each nonameric sequence inside the IgE heavy chain or other sequences. The largest binding score in this chain also matches the 'VMAPRTLLL SEQ ID NO: 51)' pattern. Initially, based on the information gathered, there were more than 100 sequences for input. Initially extracted data set were moderately balanced to incorporate diversity and skewness, more data base input will re-weight the predive precision and bias. The Program is under continually updated using feeder incorporating data, weighted differently in human and rhesus macaques. The Program, igepredict is reiteratively trained thereof for producing a fitting algorithm for a relative precision prediction.

Website Development.

A website is developed a website with python-based web framework Flask. Provide a front-end user interface allow users to enter their file and sequence. Put the prediction script in backend to analysis input data. Then generate result (or result file) and send back to front-end. Also provide new users register and login to track user activities. Log user input into the database, which permit only registered users to access. List of functions: 1: Registration system that allow super user to track users' prediction histories. 2: Integrated dashboard that gives user easy access to all the functionalities. 3: User Friendly interface for file upload and real time prediction result checking. 4: Downloadable format for spreadsheet of prediction results. 5: Multi-user capability that allow each user to upload their separated prediction queries without interference. 6: Single Sequence prediction interface that allows for Single Peptide Sequence prediction.

Example 3: Construction of Human HLA-E and Human Beta 2 Microglobulin (β2M) for HLA-E Based Peptide Binding A conformation capture of canonical/non-canonical peptide (C3N) method to HLA-E is designed to test predicted HLA-E binding peptides. HLA-E canonical and nominal peptides predicted from the python algorithm of Igepredict program and any 9 to 12-mer made collinearly with an overlapping IgE sequence can be tested by a binding assay. As illustrated herein, human HLA-E and β2m fusion construct can be made and collinearly expressed as a fusion protein as shown in FIG. 2. The assay for intact re-natured conformation of HLA-E is dependent on gaining the binding signal using anti-HLA-E coated plate to capture re-natured HLA-E in the presence of beta 2 microglobulin and leader peptides. In short, HLA-E-β2m fusion product was solubilized from the inclusion bodies in the presence of 6 M urea, and then purified from the His-tag column in the continual presence of 6 M urea. The denatured material was diluted out from 6 M urea to 100-fold to 500-fold in PBS; alternatively, the three HLA-E preps were diluted in PBS at 10 μg/ml final with the addition/incubation of A2 leader peptides from 0.1 μg/ml to 1 μg/ml for 48 h at 4° C., and captured by ELISA plate coated with anti-HLA-E. FIG. 2 showed a dramatic increment of HLA-E binding from ground zero to significant binding around 0.02 OD with HLA-E leader peptide addition at 0.1 μg/ml to, and a striking increment to 0.2 OD (~10 fold) and to above 0.3 OD (~15 fold) with the addition of 1.0 μg/ml the leader peptide. Notably, the HLA-E peptide binding capacity was enhanced with external addition of β2m (20% enhanced peptide binding compared to HLA-E heavy chain alone); in contrast, the covalently, recombinant β2m-HLA-E exhibited more than 60% peptide binding enhancement. Thus, this observation indicated that the native HLA-E structural conformation recognizable by mAb anti-HLA-E was partially restored by diluting out or dialyzing out the 6 M denaturant, and the covalently attached b2m can restore or stabilize the peptide binding capacity of HLA-E to canonical biotinylated leader peptide, and HLA-E vaccine candidate peptides can therefore compete off the biotinylated peptides to HLA-E-β2m constructs.

Thus, an embodiment of the invention is to identify the leader-like peptides and nominal peptides from druggable protein targets of the proteomic database, which compete for HLA-E binding pockets by displacing the biotinylated leader peptide as an indicator. Moreover, leader-like and nominal HLA-E binders can be predicted by the Igepredict_pythonanywhere Program of Example 2, synthesized, and tested for competitive displacement of biotinylated leader peptide in the renaturation binding assay. Therefore, one embodiment of the invention resides in using the C3N restoring the native conformation of HLA-E to test and identify HLA-E peptides predicted from various sources of therapeutic proteins, according to the pythonanywhere_Igepredict Program, which is to yield API peptide drug content/sequences for rendering universal vaccines as targets for the infectious microbial diseases, inflammatory diseases, autoimmune diseases, neurological disorders, and cancers.

Example 4: Natural Evasive UL40 Construct Harnessed as a Potent HLA-E Vaccine Delivery Platform Human cytomegalovirus (HCMV) is a beta-herpes virus developed a variety of mechanisms to down-regulate expression of MHC I, evading recognition of cytotoxic T lymphocytes. One way is to block the transporter associated with antigen processing (TAP), another way is via a fast degradation of MHC I via US2, US6 and US11 (Lehner et al. 1997. PNAS. 94: 6904; Lilley and Ploegh, 2004. Nature. 429: 834). Example 8 showed that fast degradation of classical MHC I in preventing CTL induction to both viral antigenic peptides bound to classical MHC I. Although more leader peptides are produced due to a fast degradation of classical MHC I, which can enhance HLA-E-mediated immunity. Although one aspect of viral immune evasion was described regarding silencing NKG2A/C pathway via the leader peptide mimicry encoded by viral UL40 protein as described, yet the embodiment of the invention focuses instead on the TCR/HLA-E peptide arm, which can be abrogated by whichever leader or leader-like or nominal peptide surrogates replacing the original viral leader peptide mimicry. Thus, the embodiment of the invention is that UL40 serves as a universal vaccine scaffold for accommodating API at will.

FIG. 11 showed that the cloned UL40 open reading frame (SEQ ID NO: 81, SEQ ID NO: 82) through synthetic gene approach designed by us. The synthetic gene sequence shown in FIG. 11 encodes a putative type I glycoprotein of 221-amino acid residues with an N-terminal 37amino acid signal sequence, containing the peptide homologous to the HLA-E binding peptide (from HLA-C), a 144 amino acid domain with 3 N-glycosylation sites, a 20-amino acid transmembrane domain, and a C-terminus of 20 amino acids (Tomasec, 2000, Science, 287: 1031). A typical leader-like peptide with the position 2 and 9 motif for stronger consensus HLA-E binding, while accompanied by position 3, 6, 7 on this nonamer as modulators for the main motif binding presentable to T cell receptors, wherein the binding of such a leader-like or nominal peptide can be blocked by the viral leader peptide mimicry co-translated in the N-terminus of UL40. Leader peptides from classical MHC I usually fill the binding site pockets of HLA-E, permitting its silencing of the NK cell counterpart. In contrast, position 5 and 8 as a main motif binder for NKG2x/CD94, which in this embodiment of invention is used as a platform to deviate NK cell recognition to the advantage of the immunized host, e.g., to augment a vaccine response by recruiting also NK-mediated killing of the foreign targets, e.g., viral and bacterial infected cells, and tumors; or alternatively contributing to induction of NK-mediated tolerance to prevent an undesirable targeting to self.

During the fast degradation of classical MHC I, catalyzed by CMV-encoded US11/US2, the availability of classical leader peptides can be augmented if TAP½ is not uniformly knocked down by US6 (Matshulla et al., 2017. Sci. Rep.7: 2933), and despite the competition pressure, HLA-E can be loaded with the indigenous leader peptide carried by CMV, which takes advantage of the viral mimicry leader peptides and tolerize all the leader peptides, leader-peptide-like or nominal peptides property of UL40 as an immune blindfold. The open reading frame of UL40 protein contains a 9-amino acid sequence, exactly homologous or identical to the HLA-E binding leader peptide from HLA-A2 or A2-like molecules (Tomasec et al., 2000. Science. 287: 1031). The embodiment of the invention takes advantage of this viral immune blindfold in two major ways (i) replacing a HLA-E universal autoantigenic vaccine epitope and the tolerogenic UL40 blindfold to tolerize/abort the autoimmune attack; (ii) replacing a HLA-E universal microbial or tumorous antigenic peptide vaccine epitopes together with converting tolerogenic UL40 into immunogenic UL40 signal in order to attack/neutralize the danger antigenic invasion (microbial, inflammatory and cancer).

The embodiment of the modified vector can consist of HLA-E binding motif of a nominal protein of any kind, and the site-specific mutagenesis will be prepared for make a deletion of the viral encoded HLA_A2 or _A2 like leader peptides with the leader-like nonamer(s) predicted from the igepredict program. In one version, the entirety of 221 amino acid except the swabbed out or exchanged HLA_A2 or A2-like leader peptides with a nominal leader-like peptide sequences, shall be preserved. This orthodox version should inherit in nature all possible contrivances that mediate processing out of the leader-like peptides and presentation of such peptides unto the HLA-E.

In one modified version, the transmembrane peptide of UL40 is deleted in order to have more concealed expression in the ER and peptide fragments including leader-like peptides are generated in the ER and ante-transported to the cytosol, processed by the proteasomes and retro-transported back to the ER and Golgi and permit binding and renaturation of endogenously synthesized HLA-E within the ER, and permit leader-like peptide presentation. In another version, the transmembrane sequence of UL40 is preserved to permit the natural cleavage of the leader peptide sequences from the N-terminus 37 amino acid signal peptide sequence, wherein the leader peptide-like nonameric sequences from IgE or any given nominal protein is processed and presented. In another embodiment to facilitate dimerization of the UL40, leader-like sequences swabbed in N-terminus signal sequence with the transmembrane domain deleted, is fused to an IgG Fc region, to permit dimeric leader-like peptide presentation and processing, and the fusion protein can then be employed as a leader-peptide UL40 embedded in a protein as a tolerogenic/suppressorgenic Ying vaccine. Another main embodiment of the invention it to further expand the concept of an immunogenic carrier Yang protein for immune activation, any polypeptide chain or peptide design can be used as an immunogenic carrier protein with the appropriate built-in costimulation.

In contrast, inhibitory or modulatory position 5 and 8 of HLA-E bound (viral) peptides on targets can play a key role in interacting NK cells or bifunctional CTL with NK activities in that NK cells are activated via NKG2C/E/H, which will lyse viral infected, or cancers or inflammatory cells, autoreactive or autoimmune cells as targets versus NKG2A/B, which are inhibitory for NK or bifunctional CTL to prevent target lysis. Immune evasion by CMV consists of four parts: one evasion is by destroying the immunosurveillance of classical MHC I, HLA-A, -B, and -C mediated CTL via US2, US11, which accelerates MHC I heavy chain degradation. The second is via US6 which degrades TAP½, which also abrogate CTL induction due to lack of MHC Ia-restricted viral peptides via retrograde transport from proteasomes to ER and loading to MHC I via TGN cell surface expression. The third is via the induction of inhibitory NKG2A/CD94 NK cells or bifunctional CTL, which protect or shield virus infected cells, without inducing NKG2C/CD94 lytic NK against the virus-infected cells. To tip the balance of these two activities favoring suppression, virus carries within it, the leader peptide of HLA_C, which abrogates leader like peptide immunosurveillance. An embodiment of this invention is to decipher or swap the endogenous leader peptide of UL40 with a putative vaccine epitope to render an HLA-E based universal vaccine.

The native HLA_C leader peptide must bind to HLA-E first and present the position 8 and positive 5 peptide of the mimicry HLA-E peptide to CD94, which then augments the high affinity interactions with NKG2A but not NKG2C, thus subverting the innate immunity of NK-mediated lysis via NKG2x. Furthermore, to ensure subverting adaptive immunity, UL40 will refrain from a self-destructive motif: HLA-E/VMAPRTLLL-CTL responses against itself in its own niche. The UL40L subverting immunosurveillance is to carry within it at the N-terminus human tolerogenic HLA-C leader peptide sequences as well as other tolerogenic 'contrivance sequences' in UL40, which alone or together enable tolerance or abrogation of an induced CTL response. Thus, another embodiment of this invention is to render an immunosuppressive version of UL40 as a tolerogenic vaccine carrier for vaccine epitopes for suppressing an autoimmune attack, just as the virus deploys it in its natural history of infection to subvert/tolerize a positive protective anti-viral immune defense. Another embodiment of the invention is to turn a tolerogenic response of the tolerogenic UL40 platform into an immunogenic platform by incorporating a costimulatory signal.

In summary, the embodiment of this invention is to make a tolerogenic UL40 for treating autoimmune diseases or suppress inflammatory diseases. The vaccine embodied as such strengthens the tolerogenic leader peptides, leader-like peptides, or nominal autoimmune or inflammation-related antigenic peptides is conducive for inducing central tolerance of autoreactive or autoimmune cells, or induce a Treg response, which suppress autoreactive or autoimmune cells or inflammation-eliciting cells. Furthermore, the embodiment of the invention is to turn the UL40 into a vaccine with costimulations which renders an immunogenic vaccine peptides/HLA-E restricted universal CTL response due to the lack of HLA-E polymorphism; or helper CD4 T cell/antibody-mediated immune responses to defend against microbe-infected targets, and autochthonous cancers, autoreactive/autoimmune cells.

Notably, the afore-mentioned dual embodiment of using an HLA-E peptide related to a leader peptide, a leader-like peptide, or a non-leader nominal peptide as an immunogenic active pharmaceutical ingredient (API) vaccine versus a tolerogenic vaccine, depends on the context of an immune-stimulatory costimulation, or the lack of it thereof, or being an immunoregulatory, suppressive or downregulatory costimulation. The delivery platforms can be peptide-based, recombinant peptides in a suitable carrier protein such as UL40, or presented as a DNA vaccine, wherein costimulatory or suppressive modulators provided in an appropriate form. Thus, the following costimulatory molecules will be administered in an appropriate dosage and via an appropriate vaccination route culminating in determining a dichotomous outcome favorable for an immune response, which benefits the host in protecting against microbial infections, autochthonous tumors, and inflammatory diseases; or favorable for alleviating autoimmune attack or other inflammatory diseases.

The costimulatory and coinhibitory molecules (Vinuesa et al. 2016. ARI 34: 335: Baumeister et al. ARI. 2016. 34: 539; Chen and Flies. 2013. Nat. Rev. Im. 13: 227; Esensten et al. 2016. Immunity. 44: 973) include and not limited to members of the immunoglobulin superfamily (IGSFs) and members of the tumor necrosis factor receptor superfamily (TNFRSFs). The invention embodies the use of two types of costimulatory and co-inhibitory molecules enabled by use of an agonistic or antagonistic antibody or by a protein, a peptide, a DNA or RNA aptamer with adaptive binding to modulate the two classes of molecules therewith. Alternatively, a DNA vaccine packaging such a member of the two classes of molecules can be used along with the HLA-E based vaccine as a DNA vaccine adjuvant adjunct. This embodiment assists an immunogenic vaccine the immune defense as well as a tolerogenic vaccine for immune homeostasis.

1. TNF Receptor Superfamily (TNFSF):

TNFRSF receptors contain one or more extracellular cysteine-rich domains (CRDs), whereas the TNFSF ligands (TNFSF) contain a conserved extracellular TNF homology domain (THD), including HVEM, death receptor 3 (DR3, or TNFRSF25), CD40 (TNFRSF5) and lymphotoxin-β receptor (LTBR, TNFRSF3), transmembrane activator and CAML interactor (TACI, TNFRSF13B), B cell-activating factor receptor (BAFFR, TNFRSF13C), B cell maturation protein (BCMA, TNFRSF17), interacting with APRIL, TNFSF13), B cell-activating factor (GAFF, TNFSF13B) which co-stimulates B cells; TWEAK receptor (TWEAKR, TNFRSF12A), ectodysplasin-A receptor (EDAR) and X-linked ectodysplasin-A receptor (XEDAR, TNFRSF27) as costimulatory or co-inhibitory molecules. Moreover, 4-1BB (CD137, TNFRSF9), OX40 (TNFSF4), CD27 (TNFRSF7), glucocorticoid-induced TNFR-related protein (GITR, TNFRSF18) and CD30 (TNFRSF8) as co-stimulatory molecules.

2. Immunoglobulin Superfamily (IGSFs):

CD28 family interact primarily with members of the B7 family, albeit the co-inhibitory B and T lymphocyte attenuator (BTLA) engage the TNFRSF member herpes virus entry mediator (HVEM or TNFRSF14), and B7-H6 (NCR3LG1) engage NKp30 or NCR3 of the natural cytotoxicity receptor family in humans. Type I T cell immunoglobulin and mucin domain-containing molecules (TIM) consist of an IgV-like domain and a mucin-like domain. TIM can be co-stimulatory or co-inhibitory, CD2/SLAM: CD2 and signaling lymphocytic activation molecule (SLAM) with an IgV and an IgC domain interact with CD2 in a homophilic or heterophilic fashion. CD2 and SLAM function as co-stimulatory receptors on T cells, whereas 2B4 and LY108 function as co-inhibitory molecules. Butyrophilin (BTN) and BTN-like (BTNL) family molecules have extracellular structures are B7 family-like, while the function of a canonical b30.2-RING domain resident in the cytoplasmic tails can impart either a co-stimulatory or co-inhibitory.

In addition, CD4-like lymphocyte activation gene 3 protein (LAGS, or CD223), interacting with MHC H is co-inhibitory. Receptors CD226 (DNAM1), T cell immunoreceptor with immunoglobulin and ITIM domains (TIGIT; also known as VSIG9), cytotoxic and regulatory T cell molecule (CRTAM) and CD96 (TACTILE) as a group can interact with nectin and nectin-like ligands. CD226 and CRTAM are co-stimulatory, while TIGIT is co-inhibitory, and CD96 may be either. Leukocyte-associated immunoglobulin-like receptor 1 (LAIR1, or CD305) of the LAIR family with a single C2-type immunoglobulin-like domain binding collagens is co-inhibitory. CD160, a glycosylphosphatidylinositol-anchored molecule with an IgV-like domain that on T cell deliver a co-inhibitory signal upon HVEM binding. Thus, one embodiment of this invention is that all the above co-stimulatory or co-inhibitory molecules of the IgSFs are employed as a vehicle of costimulation for stimulatory HLA-E-based vaccine for immune defense against tumor, microbial infections, while the co-inhibition can be harnessed to treat HLA-E mediated autoimmune diseases.

The switch between the tolerogenic and immunogenic on/off state can be manipulated at will by modulating the second stimulatory signals. The second costimulatory immunogenic signals include but are not limited to CD40, B7-1/CD80, B72 (CD86), OX-40, 41BB, TIM-1; CD28, ICOS, PD1H, TIGIT, BTLA, while the second costimulatory signals can be the high zone or low zone tolerogen by itself, PD-1, PDL-1, CTLA-4, LAG-3 (CD4 like, CD223), TGF-β, IL-10, CD25, ICOS. Thus, the viral infected targets with HLA-E blocked by UL40 escape the damage NK-mediated damage. Thus, CMV can subvert classical MHC I-mediated CTL via US11/US2, as well as subverting HLA-E-mediated CTL and CD94/NKG2A/B NK-mediated lysis via UL40 evasion. And a complete optimization relies on the also the tolerance induction in the boxed in leader peptides to also evade boxed-in leader peptide, or leader-peptide like structure in HLA-E mediated CTL response. Hence the UL40 module can be engineered further into the tolerance module vs immunity modules with or without supplemented co-stimulation signals.

One main embodiment of the invention is to deploy viral UL40 (Tomasec et al., 2000, Science, 287: 1031) in a recombinant construct as a vaccine platform to deliver leader peptide-like and nominal sequences from a microbial protein, an autoimmune protein target, or IgE target respectively as a universal vaccine. Specifically, the viral mimicry leader peptide is replaced with an IgE leader peptide like sequence or nominal sequence in IgE to the N-terminal region of UL40 so that the IgE peptide(s) is juxtaposed to load onto the HLA-E binding pocket according to a similar strategy the viral delivery to arm or preempt a tolerogenic HLA-E. As an immunogenic vaccine, the vaccine-epitope inserted UL40 is further fused to an immunogenic CD4 epitope or a carrier protein or an aforementioned costimulatory signal, enabling the delivery of a second helper signal in order to provoke a vaccine epitope/HLA-E restricted CTL response, a CD4 response, a Ts/Treg response against the IgE-producing cell target for treating allergic inflammation, a viral infected cell for treating viral disease, or a target cell producing TNF-α for treating rheumatoid arthritis; therefore to alleviate IgE-mediated allergy, to clear a viral infection, and to attenuate inflammatory mediators and/or alleviate cytokines-mediated inflammation.

Henceforth, this embodiment is a two-fold technology innovation subverting the otherwise natural tolerogenic UL40-'leader peptide in signal peptide', e.g., the 'original viral sin' is replaced or resurrected to a protective immunity to the advantage of the host, an antigenic peptide is piggybacked together with a second helper signal in order to break tolerance to the engineered antigenic peptides or a mimetics within the viral UL40 construct. Two modalities of breaking tolerance is to deliver an IgE mimicry; (i) in conjunction with an immunogenic carrier to stimulate CD4 helper T cells, e.g., promiscuous helper T cell peptides: PADRE, tetanus toxoid peptides, diphtheria toxin peptide, measles helper peptides, and KLH, GFP and other immunogenic proteins; (ii) in conjunction with an immunogenic adjuvant, e.g., those eliciting innate immunity via TLR (Toll-like receptor), NLR, and CpG, UL40-IgE mimetics; (iii) via an HLA-E expressing APC in a cell-based immunogenic adjuvant formulation. Thus, IgE mimetics is naturally processed along with endogenous HLA-E serving as a vaccine API, while the immunogenic formulation serves to provide the second helper or suppressive/transformative signal. Thus, a main embodiment of this invention is to substitute viral leader peptide sequences with IgE or nominal protein leader peptide-like sequences that arm the HLA-E for a universal IgE peptide or nominal peptide vaccine in the presence of second signal to elicit immune responses, breaking tolerance and cause infectious tolerance.

In another embodiment of the vaccine delivery, the DNA sequence encoding HLA-E binding peptides are cloned into a mammalian expression vector with a co-expressed immunogenic cytokine such as GM-CSF, CD40L, OX40L, IL-4, IL-5, IL-12, IFN-gamma, TGF-beta, suppressive Nrf-2, IL-35, heme oxygenase 1 (HO-1) or other recombinant costimulatory factors. HLA-E biding peptides DNA vaccine is injected intradermally (id)/transcutaneously (TCI), or via intramuscularly (im) via a primed and boost schedule at appropriate intervals. Mucosal and systemic immunity of eliciting 8-11 amino acid peptides/HLA-E. In another embodiment of HLA-E vaccine delivery, immunogenic 8-11 amino acid peptides are co-administered with promiscuous helper peptides, e.g., PADRE, diphtheria toxin peptides, tetanus peptides or measles virus helper peptides, or other immunogenic carrier protein in adjuvants, e.g., KLH and others, in the presence of adjuvant such as immune-stimulatory CpG, TLR ligands for toll-like receptor 1-13, NLR ligands for Nod-like receptors: NODs, NLRPs, IPAFs.

Example 5: Application of Universal MHC Ib, e.g., HLA-E, -F, -G Vaccines Against Pan-Human Diseases, Including Infectious Diseases, Inflammatory Diseases, Autoimmune Diseases, Neurological Disorders, and Cancers The invention concept of a universal vaccine is based on the presence of the universal, non-polymorphic HLA-E protein ubiquitously expressed on all the immune cell types (CD4, CD8, B cells, dendritic cells), and all the somatic cells, including cancers. FIG. 4 showed that nearly all the CD14 monocytes, including MoDCs and cDCs in this cellular set, are intensively positive for HLA-E, and to the same extent, about 60% or more of CD4 and CD8 cells are scored positive in normal peripheral blood mononuclear cells (PBMCs) under normal non-activating conditions separated from the human plasma. Importantly, circulating CD19 B cells are negative for HLA-E, except that activated CD19+ B cells (more skewed SSC/FSC) exhibit high higher levels of HLA-E, indicating a function of surface inducible HLA-E on B cells.

Due to this ubiquitous presence of HLA-E on the CD14 containing antigen presenting cells, e.g., dendritic cells, and cells of the myeloid series, CD4 helper and immunoregulatory cell types, as well as CD8+ cytotoxic and/or immunoregulatory cells, thus as shown in FIG. 10, there exists a communication network amongst these cell types via presentation and bi-lateral recognition of the HLA-E and TCR-bearing cell and NK cell network.

Noticeably, a tri-lateral communication is built in the cellular network (FIG. 10) due to availability and feasibility of HLA-E in the Treg and Teff, which can bind to endogenous self-peptide pools generation in the ER pathway, in that CD4+, CD4+CD8+, CD8+ Treg (Ts) and/or Teff can form mutual cognitive pairs of different assortments, e.g., Treg-Teff, Teff-Teff and even Treg (Ts)-Treg (Ts), and the pairing will permit an exchange of augmenting or suppressive signals amongst the cellular interactions. For example, CD4 Teff, or Treg (e.g., CD4 bearing/nonamer-HLA-E restricted, wherein high affinity nonamer binding via TCR compensates for the lower CD4 coreceptor binding to the α3 domain of HLA-E) or CD8 Teff or Treg recognizing an HLA-E-restricted autoantigenic peptide, initiating an autoimmune attack on the nervous tissues, can itself be recognized by HLA-E-self peptide restricted Treg (Ts), which recognize self-peptides processed and presented by the autoimmune CD4 Teff or Treg or CD8 Teff or Treg or autoantigenic peptides bound to itself via its own HLA-E (HLA-E ubiquitously expressed on all immune cell types, FIG. 4).

As a corollary, each T cell regardless of the functionality as an effector or a regulator bears the HLA-E decorated self-marker, which in turn can be regulated amongst HLA-E restricted T cell community in a direct cognition. Alternatively, this type of interaction can intercalate or integrate with different types of APC to form a tripartite interaction, indirectly influencing each other via an APC, by forming a constellation so that the two T cell can cement a relation via an APC chaperone. As another corollary, an HLA-E-based peptide vaccine, can initiate an HLA-E and peptide based Teff or Treg (Ts) response, while these induced T cells can also bound the vaccine peptide and becomes mutually self-regulated within a special niche community. In another variation, if two such autoimmune peptides are administered simultaneously as vaccines. The T cell pair can form heterotypic interaction of two different HLA-E specific T cell pair of different functional assortment at will.

Thus, one embodiment of this invention is to administer at least one HLA-E peptide, or two, or more peptides or such peptides synthesized or recombinantly produced in tandem in a colinear and covalent fashion in order to orchestrate a desirable and robust impact of the HLA-E vaccine.

Overall, the embodiment of the invention resides in immunizing for the protective and ameliorating effect of a positive vaccine response using the method of identifying the pertinent disease-relevant non-self, foreign, naturally processed antigenic peptides (microbial peptides) from the microbial sources of infected cells, and self-antigens from tumors (cancer antigenic peptides) and inflammatory tissues [IgE (SEQ ID NO: 43), rheumatoid factors, TNF-α (SEQ ID NO: 44, SEQ ID NO: 45)]. These naturally processed therapeutic peptides can be used as vaccines for eliciting effector CTL mediated responses along with immune-stimulatory enhancer (ISE) adjuvants. Another embodiment of the invention resides in tolerizing an potential or ongoing autoimmune attack damaging the tissues and organs. In this embodiment, the focal point of therapeutic interest is inducing CD8+ or CD4+ Treg, which alleviate the effector cell-based immune damage. Immuno-regulatory suppressive (IRS) adjuvants will be used with the therapeutic HLA-E based universal peptide vaccines.

Since HLA-E presenting somatic antigenic, leader sequence like peptides and nominal peptides can be characterized, identified, and sequenced via affinity chromatography, HPLC and MS/MS [FAB, triple quadruple, ion trap and time of flight (TOF)]. The occurrence of these developmental driven events, e.g., somatic antigenic peptide processing, and fitting onto HLA-E is at the formation and embryogenic stages. Thus, self/non-self discrimination of the HLA-E-based system like classical MHC I and MHC II take place similarly according to clonal deletion, clonal abortion, clonal anergy, and clonal activation and clonal infectious tolerance at levels of CD8, CD4 T-cells.

One embodiment of this invention is to immunize the host with HLA-E restricted tumor antigenic peptides along with strong costimulation, resulting in HLA-E restricted CTL to the HLA-E to damage tumors expressing HLA-E bound with tumor antigenic peptides. HLA-E restricted CTL can also express CD94/NKG2C to lyse HLA-E expressing tumor cells. The appropriate costimulation provided to bifunctional CTL/NK or NK will overcome the microenvironmental suppressive effect and render the CTL/NK competent to kill the tumor cells. The embodiment of this invention resides in harnessing the nominal tumor antigens on HLA-E for inducing anti-tumor CTL responses. Thus, this new arm of sterile immunity will not only attack or lyse tumors but also cause a tumor cell to withhold its tolerizing capacity against NK via a disengagement HLA-E from NKG2A/CD94 of NK cells. Notably, in this embodiment, the CTL induced by the HLA-E/tumor antigens can be a bifunctional NK-CTL, and under strong costimulation, expressing not only TCR immunized and specific for the tumor antigenic peptides restricted or presented by nonclassical MHC I, HLA-E but also express NKG2C/CD94 and NK-mediated killing of the tumors engaging in a dual protective pathway.

Many tumors are known to express high levels of HLA-E (Seliger, et al., Oncotarget, 7:67360; Huang, Oncol. Lett. 2017. 13: 3379), which bind to classical MHC I leader peptides as an immune evasive mechanism to tolerize NK-mediated defense. HLA-E expression on cancers lead to poor prognosis (Gooden, 2011. PNAS, 108:26). Lowering HLA-E levels enhanced NK-mediated cancer elimination (Enqvist et al., 2011. J. Immunol: 187:3546). Presentation of HLA-A2 leader peptide/HLA-E complexes by the tumors to NKG2A/CD94 expressing on NK cells or CTL can also render the CTL/NK or NK tolerant (Borrego et al, 1998 JEM 187:813). Typically, CD8 T cells to autologous leader peptides are well tolerized in an individual (Pietra, 2003. PNAS, 100:10896), and these anergic cells can be detected in a high percentage (~10%) using autologous leader peptide-HLA-E tetramer staining method.

The principle of tolerance can be extended to leader-like self-peptides, and also nominal self-peptides bound to or presented by HLA-E. In principle, a nominal autochthonous tumor antigen from cancers derived from the patients particularly in the suppressive tumor microenvironment can be presented as a tolerogen. Since tissue proteins such as insulin, epidermal growth factor (EGF), other growth factors, cell cycle proteins etc., share identical amino acid sequences among individuals without exhibiting amino acid variation or polymorphism, of which the endogenously processed peptide presented by nonpolymorphic HLA-E renders a peptide antigenic candidate of the first in-kind universal cancer vaccine, fit for every cancer patient of the same tissue pathology, when coupled with a second costimulation.

The embodiment of this invention is to immunize the host with the HLA-E restricted antigenic peptide in the context of the second costimulatory signal for triggering or converting the tolerogenic signal to immunogenic signal, including covalent juxtaposition of the nominal peptide in the N-terminus and helper costimulation in the C terminus of the UL40 construct. Thus, this embodiment causes induction and amplification the CTL-mediated sterile immunity and NKG2C type NK-mediated lysis against this self-tissue tumor antigenic peptides restricted/presented by HLA-E on cancer cells. It follows with the peptide presentation by HLA-F and HLA-G, and recognition by T cells and NK cells. The embodiment of this invention claims a unique or universal tumor antigen presented by a nonpolymorphic HLA-E of non-classical MHCI, leading to activation of sterile CTL immunity and NK-mediated defense, wherein the tolerogenic signal is transformed by the second costimulatory signal for the product concept of a universal cancer vaccine unrestricted and unlike that of classical MHC I fit for an entire population.

An example as mentioned in Example 4 above, UL40 construct can be modified into an ISE for effector immune cells or into IRS for immunoregulation. A network of cellular communication among the three major cell types can exist in the immune system via the HLA-E+ peptides, e.g., self-peptides and foreign peptides as targets on the receptive cells, whereas HLA-E negative, or HLA-E+ peptide-specific CD4 and CD8 T cells can recognize HLA-E+ self/non-self peptides on CD4+, CD8+ T cells to form a direct network of T-T communication without the presence of APC; and the former T cell (HLA-E+ or −) is HLA-E-restricted, while the latter T cells bearing HLA-E+self/non-self peptides can be restricted to nonclassical MHC I or classical MHC I presenting self or non-self peptides, and can like also engage in recognition of the former T cell via HLA-E restricted recognition, alternatively can recognize self peptide presented by classical MHC I plus peptides on a target. Thus, there can be bidirectional communication of these HLA-E+ self/non-self peptides CD4+ and CD8 T cells among themselves.

All the cells have HLA-E can have both a switch-on and a switch-off modality/module according to the state of the cells. Thus, this network permits an autochthonous, autologous, mono- or bidirectional mode of communications among a combinatory assembly of the immune system components in a non-classical MHC I, e.g., HLA-E and Qa1 and Qa2-based or also mixed with classical MHC I-based immunoregulatory network. In a particular case regarding controlling IgE production, naturally IgE-leader-like peptides generated in IgE lineage B cells, including IgE precursor cells, B cells and B cell blasts and plasma cells can be processed and presented onto the HLA-E (all the immune and non-immune cell types), which render itself susceptible to the cytolytic or immunoregulatory attack by the aforementioned HLA-E+ natural IgE peptides reactive CD4 and CD8 T. Hence an appropriately identified IgE natural peptide, appropriately delivered to stimulate a vaccine response can inhibit IgE production at the levels of IgE lineage cells, henceforth, ameliorate IgE-mediated allergic inflammation with the status being the HLA-E-based universal IgE allergy vaccine.

An embodiment of this invention is to combat infectious disease antigens of the viral diseases, employing microbial proteins of immune protective or therapeutic use in the presence of costimulation annulling coinhibition (Vinuesa et al. 2016. ARI. 34: 335; Baumeister et al. ARI. 2016. 34: 539; Chen and Flies. 2013. Nat. Rev. Im. 13: 227; Esensten et al. 2016. Immunity. 44: 973), e.g., those of the non-self antigens, pertaining to infectious microbes of endogenous bacterial and viral origins (Goldman's Cecil Medicine 24 ed, 2012, Elsevier) such as [*Tuberculosis* (*Mycobacteria tuberculosis, M. bovis*), Leprosy (*M. leprae*), Legionellosis (*Legionella pneumophilia*), *Listeria monocytogenes* infection, *Salmonellosis* (*Salmonella enterica, S. bongori*) Lyme Borreliosis (*Borrelia burgdorferi*), Actinomycosis (Actinomycetes, spp), *Chlamydia* infection (*C. trachomatis, C. pneumoniae*, resident in macrophages] and viral sources of infections, e.g., human immunodeficiency virus (HIV), Epstein-Barr virus (EBV), human respiratory syncytial virus (HR,SV), influenza virus (IV), para-influenza virus (PIV), rotavirus, rhinovirus, adenovirus infection, sever acute respiratory syndrome (SRAS) virus; GI tract: norovirus, rotavirus, adenovirus, astrovirus; Exanthematous viral diseases: measles virus, rubella virus, chicken pox/shingles, roseola, smallpox, fifth virus, chikungunya virus infection; hepatitis virus: hepatitis virus A, B, C, D, E; cutaneous viral diseases: warts virus, genital warts virus, oral herpes virus, genital herpes virus, *Molluscum contagiosum* virus; hemorrhagic diseases: Ebola virus, Lassa fever virus, dengue fever virus, yellow fever virus, Marburg hemorrhagic fever virus, Crimean-Congo hemorrhagic lever virus; neurologic viral diseases: polio virus, meningitis virus, encephalitis virus, rabies virus.

In contrast, autoimmune diseases can be initiated and maintained by effector CD4 or CD8, CD4/CD8 T cells or autoantibody-producing B cells. Numerous somatic autoantigens with exaggerated expression or neoantigenic expression in pathological conditions in a tissue and/or an organ, struck with aberrantly flared up forms of cytokines or other pathogenic proteins during inflammation, an autoimmune disease. The aberrant expression of autoantigens can be evaluated by the elevated level of mRNA via RT-PCR, and identifiable proteins via western blots. HLA-E based vaccine peptide epitopes can be evaluated and assessed via the self-peptides predicted via a given protein or discovered by purifying HLA-E with its bound peptides, acidic elution of bound peptide, followed by MS/MS peptide sequencing (DH Hunt et al., 1992. Science 255: 1261). In the embodiment, synthetic peptide vaccines, peptide sequences contained in recombinant proteins, or recombinant DNA vectors including using UL40 can be prepared as a source of DNA vaccines. Treg or infectious tolerance can be induced by HLA-E elicited autoantigenic peptides by immunization in the absence of costimulations or provided with suppressive microenvironment conducive for Treg and infectious tolerance.

One main embodiment herein is to induce HLA-E/autoantigenic peptide specific Treg to suppress effector CD4, CD8 T cell-mediated, or antibody-producing B cells-mediated tissue damage in the following types of autoimmune diseases (Sinmaz et al., 2016: 13:219; Riedhammer and Werssert. 2015. Front. Im. 2015. 6: 322; Tong et al. J Inf. Dis. 2017. 10: 97; Pianta et al. 2017. J.C.I. 127: 2946; Meched et al. 2016. FASEB J. 30:2123), including and not limited to organ specific (Type I diabetes mellitus, thyroiditis, mysasthenia gravis, primary biliary cirrhosis, Goodpasture's syndrome), or systemic (rheumatoid arthritis, progressive systemic sclerosis, systemic lupus erythematosus). The neurological autoantigens involved in autoimmune neurological lesions are as follows. Autoantigens found in CNS antibody-mediated disorders include N-methyl-D-aspartate receptor (NMDAR), α-amino-3-hydroxy-5-methyl-4-isoxazolepropionic acid receptor (AMPAR), glycine receptor (GlyR), components of the voltage-gated potassium channel (VGKC) complex, including leucine-rich glioma-inactivated protein 1 (Lgi1) and contactin-associated protein-like 2 (Caspr2), γ-aminobutyric acid receptor-B (GABA$_B$R), γ-aminobutyric acid receptor-A (GABA$_A$R), metabotropic glutamate receptor 5 (mGluR5), dipeptidyl-peptidase-like protein-6 (DPPX), dopamine-2 receptor (D2R), myelin oligodendrocyte glycoprotein (MOG), aquaporin-4 (AQP4), 65 kDa glutamic acid decarboxylase (GAD65), neurofascin (NF), and contactin. Furthermore, a number of different autoantigens have been discovered in neuromuscular junction antibody-mediated disorders. These include acetylcholine receptor (AChR), muscle-specific kinase (MuSK), lipoprotein receptor-related protein 4 (Lrp4), all associated with myasthenia gravis (MG), and voltage-gated calcium channel (VGCC) associated with PNS Lambert-Eaton myasthenic syndrome (LEMS); collagen type II, human cartilage gp39 (HCgp39), gp130-RAPS associated with rheumatoid arthritis; fibrillarin, small nucleolar protein (snoRNP) associated with scleroderma; thyroid stimulating factor receptor (TSH-R) associated with Graves' disease; nuclear antigens, DNA, histone, glycoprotein gp70, ribosomes associated with systemic lupus erythematosus; PDC-E2 (mitochondrial enzyme, pyruvate dehydrogenase dehydrolipoamide acetyltransferase) associated with primary billiary cirrhosis; Hair follicle antigens associated with Alopecia areata; Pancreatic β-cell antigens, insulin, GAD and its isoforms associated with IDDM; MBP, PLP, MOG associated with multiple sclerosis; Human tropomyosin isoform 5 (hTM5) associated with Ulcerative colitis.

Highly reactive lipid intermediates (Sinmaz et al., 2016: 13:219; Riedhammer and Werssert. 2015. Front. Im. 2015. 6: 322; Tong et al. J Inf. Dis. 2017. 10: 97; Pianta et al. 2017. J.C.I. 127: 2946; Meched et al. 2016. FASEB J. 30:2123): MDA and HNE modified low-density lipoproteins (LDL), oxidized LDL (oxLDL), and 8-oxodeoxyguanine modified LDL in atherosclerotic plaques; oxLDL in Behcet's disease; oxidation-specific surface antigens on apoptotic cells; oxidized liver antigens in alcoholic liver disease; HNE-modified 60-kDa Ro in animal model of SLE; oxidized carbohydrates; IgG modified with advanced glycation end (AGE)

product; pentosidine modified IgG in rheumatoid arthritis; Oxidized glutamic acid hydroxylase in IDDM; Type I diabetes: Carboxypeptidase H, Chromogranin A, Glutamate decarboxylase, Imogen-38, insulin, Insulinoma antigen-2 and 2β, Islet-specific glucose-6-phosphatase catalytic subunit related protein (IGRP), proinsulin; MS: α-enolase, Aquaporin-4, β-arrestin, Myelin basic protein, Myelin oligodendrocytic glycoprotein, Proteolipid protein, S100-β; Rheumatoid arthritis: Citrullinated protein, Collagen II, Heat shock proteins; Systemic lupus erythematosus: Double-stranded DNA, La antigen, Nucleosomal histones and ribonucleoproteins (snRNP), Phospholipid-β-2 glycoprotein I complex, Poly(ADP-ribose) polymerase, Sm antigens of U-1 small ribonucleoprotein complex. The embodiment of the invention is to utilize the above autoantigenic peptides to elicit an HLA-E mediated immune protective responses to dampen autoimmunity attack.

Derlin-1 and US11 as Vaccine Adjuvant

MHC I destined for the surface membrane expression bound to endogenous or antigenic peptides survive in the ER lumen, whereas misfolded MHC I in a quality-control process is transferred from the ER to the cytosol in a ubiquitin-dependent pathway in exported via AAA ATPase (Cdc48/p97), Derlin-1 forming complexes with co-factors, Ufd1p and Npl4p, into cytosol for degradation by the 26S proteasome. Normally the leader peptides from HLA-A, -B, -C are constitutively available and loaded onto HLA-E; and this constitutive level of endogenous leader peptide loading can compromise the vaccine peptide loading onto HLA-E.

Thus, one embodiment of vaccine peptide loading unto the HLA-E compartment resides in clearing house of endogenously already occupied house-keeping HLA-A, -B leader peptides. Protein quality control process entails a mechanism whereby misfolded HLA-A, -B, -C proteins were loaded onto an internal antegraded ER-associated degradation (ERAD) assembly exporting into cytosol. Breaking down of leader peptide sequences and HLA-A, -B, -C subsequently take place in cytosolic proteasomes, whereby leader peptides of HLA-A, -B, -C are retrograded transported via the TAP transporter, to be imported and reloaded onto HLA-E. The quality control process can be controlled by two human cytomegalovirus proteins, US11 (SEQ ID NO: 87, SEQ ID NO: 88), and US2 (SEQ ID NO: 89, SEQ ID NO: 90) causes a rapid transfer of MHC I heavy chain from the ER to the cytosol, and Derlin-1 as an ER membrane protein essential for US11-mediated antegrade translocation of the class I HC. where N-glycanase, ubiquitin-conjugating enzymes and finally the proteasomes act on them. A human homologue of yeast Der1p, Derlin-1 (SEQ ID NO: 85, SEQ ID NO: 86), a protein essentially required for the degradation of a misfolded ER luminal proteins, including MHC I (Lilley and Ploegh, 2004. Nature, 429:834) as the partner essential for US11 to perform its function. US11 is a 215 amino acid glycoprotein, whereby the luminal domain interacts with MHC I, while the transmembrane domain interacts with Derlin-1, which is in a large complex tight in with the antegrade pathway exporting to cytosol for degradation. The US11 enormously accelerate the association of misfolded MHC I with Derlin-1, the degradation process within minutes of its synthesis. It is possible that Derlin-1 acts to degrade cellular ER proteins independently of the US11 and US2.

Derlin-1 forms an integral part of the antegraded machinery required for transporting classical MHCI, e.g., HLA-A, -B, -C for proteasome degradation. Table I and FIG. 9 showed that we have uncovered three anti-Derlin-1 siRNA, which knockdown Derlin-1 expression up to 65% in three types of antigen-presenting cells by sensitive RT-PCR, those of MoDCs, T2 (B and T cell hybrid lymphoid tumor), and 0.221 B cells (HLA-A, -B, -C, -E not expressed). In contrast, the protein band of Derlin-1 is entirely missing in Derlin-1 siRNA-treated MoDCs. Transfection of the primary cells were performed using PEI reagents (Viromer Blue vs. Viromer Red). The embodiment of the invention is three-fold. One aspect of the embodiment resides in treating APC with Derlin-1 RNA interference to prevent the generation of endogenous leader peptide as well as to cause dissociation of the HLA-E bound endogenous leader peptides so that Derlin-1-treated APC can be fully loaded with the HLA-E vaccines in the presence of the second costimulatory signal for immune induction.

Alternatively in the absence of costimulation to cause immunoregulation of autoimmune or inflammatory diseases. Notably, although US11 and US2 accelerate the fast degradation of classical MHCI: HLA-A, -B, and -C it does not affect the integrity of nonclassical MHC I (Schust, 1998. JEM, 188:497): HLA-G, and HLA-E, HLA-F by extension. Thus, another aspect of embodiment resides in treating APC with US11 plasmid constructed from the CMV (FIG. 11), and the intact, unaffected HLA-E compartment without a competing classic MHC I antigenic peptide presentation from the microenvironmental milieu, can further augment vaccine peptide presentation. In. this embodiment, a fast degradation of MHC I by US11 can ease up antigen presenting energy space/time to facilitate nonclassical MHCI-based vaccine peptide presentation. In this freed-up space/time, a modification of this embodiment resides in a co-transfection of the vaccine leader peptide-like or nominal vaccine peptide constructed within the UL-40 plasmid mimics natural infection, while co-administered with a second signal, mimicking a reversal phase of the natural infection.

The embodiment of this invention residing in slowing down the export of HLA-A, -B, -C by downregulating the Derlin-1 based exporter complexes, hence permitting dissociation of already bound endogenous leader peptide, and the freeing up the binding pocket and availability of HLA-E for exchanging the tolerogenic leader peptides with the vaccine epitopes, which can be imported via the TAP exporter pathway, or inside the ER via UL-40 which can directly load the IgE leader peptide-like sequence. An aspect of this embodiment resides in using MoDCs or PBMC, blood dendritic cells, B cells or monocytes, treated with Derlin-1 inhibitors or RNA interference, thus facilitating HLA-E vaccine peptide pickups and loading into the empty binding pocket of HLA-E.

I claim:

1. A composition comprising a Cytomegalovirus (CMV) UL40 fusion protein, wherein the N-terminal leader peptide of UL40 is replaced by IgE peptides selected from the group consisting of SEQ ID NO: 18 to SEQ ID NO: 43 and SEQ ID NO: 52 to SEQ ID NO: 61, and SEQ ID NO: 68 to SEQ ID NO: 80.

2. A composition comprising a Cytomegalovirus (CMV) UL40 fusion protein, wherein the N-terminal leader peptide of UL40 is replaced by nonameric TNF-1α peptides selected from the group consisting of SEQ ID NO: 44 and SEQ ID NO: 45.

3. A composition comprising a cell expressing the UL40 fusion protein of claim 1 or 2.

4. The cell of claim 3 further comprising an immunogenic carrier.

5. The cell of claim 3 further comprising a tolerogenic carrier.

6. The fusion protein of claim 1 or 2 further comprising an immunogenic carrier.

7. The fusion protein of claim 1 or 2 further comprising a tolerogenic carrier.

* * * * *

SEQUENCE LISTING

```
<160> NUMBER OF SEQ ID NOS: 90

<210> SEQ ID NO 1
<211> LENGTH: 1000
<212> TYPE: DNA
```

<213> ORGANISM: Homo sapiens

<400> SEQUENCE: 1

| | | | | | | |
|---|---|---|---|---|---|---|
| atggtagatg | gaaccctcct | tttactcctc | tcggaggccc | tggcccttac | ccagacctgg | 60 |
| gcgggctccc | actccttgaa | gtatttccac | acttccgtgt | cccggcccgg | ccgcggggag | 120 |
| ccccgcttca | tctctgtggg | ctacgtggac | gacacccagt | tcgtgcgctt | cgacaacgac | 180 |
| gccgcgagtc | cgaggatggt | gccgcgggcg | ccgtggatgg | agcaggaggg | gtcagagtat | 240 |
| tgggaccggg | agacacggag | cgccagggac | accgcacaga | ttttccgagt | gaatctgcgg | 300 |
| acgctgcgcg | gctactacaa | tcagagcgag | gccgggtctc | acaccctgca | gtggatgcat | 360 |
| ggctgcgagc | tggggcccga | cgggcgcttc | ctccgcgggt | atgaacagtt | cgcctacgac | 420 |
| ggcaaggatt | atctcaccct | gaatgaggac | ctgcgctcct | ggaccgcggt | ggacacggcg | 480 |
| gctcagatct | ccgagcaaaa | gtcaaatgat | gcttctgagg | cggagcacca | gagagcctac | 540 |
| ctggaagaca | catgcgtgga | gtggctccac | aaatacctgg | agaaggggaa | ggagacgctg | 600 |
| cttcacctgg | agccccaaa | gacacacgtg | actcaccacc | ccatctctga | ccatgaggcc | 660 |
| accctgaggt | gctgggccct | gggcttctac | cctgcggaga | tcacactgac | ctggcagcag | 720 |
| gatggggagg | gccatacca | ggacacggag | ctcgtggaga | ccaggcctgc | aggggatgga | 780 |
| accttccaga | gtgggcagc | tgtggtggtg | ccttctggag | aggagcagag | atacacgtgc | 840 |
| catgtgcagc | atgaggggct | acccgagccc | gtcaccctga | gatggaagcc | ggcttcccag | 900 |
| cccaccatcc | ccatcgtggg | catcattgct | ggcctggttc | tccttggatc | tgtggtctct | 960 |
| ggagctgtgg | ttgctgctgt | gatatggagg | aagaagagct | | | 1000 |

<210> SEQ ID NO 2
<211> LENGTH: 1000
<212> TYPE: DNA
<213> ORGANISM: Homo sapiens

<400> SEQUENCE: 2

| | | | | | | |
|---|---|---|---|---|---|---|
| caaagtgctg | agattacagg | cgtgagccac | cgcgcccagc | caggactaat | ttctaagagt | 60 |
| gtgcagagat | accgaaacct | aaaagtttaa | gaactgctga | ttgctgggaa | actctgcagt | 120 |
| ttcccgttcc | tctcgtaacc | tggtcatgtg | tccttcttcc | tggatactca | tgacgcagac | 180 |
| tcagttctca | ttcccaatgg | gtgtcgggtt | tctagagaag | ccaatcagcg | tcgccacgac | 240 |
| tcccgactat | aaagtcccca | tccggactca | agaagttctc | aggactcaga | ggctgggatc | 300 |
| atggtagatg | gaaccctcct | tttactcctc | tcggaggccc | tggcccttac | ccagacctgg | 360 |
| gcgggtgagt | gcggggtcgg | gatggaaacg | gcctctaccg | ggagtagaga | ggggccggcc | 420 |
| cggcgggggc | gaaggactcg | gggagccgcg | ccggaggag | ggtcgggccg | atctcagccc | 480 |
| ctcctcgccc | ccaggctccc | actccttgaa | gtatttccac | acttccgtgt | cccggcccgg | 540 |
| ccgcggggag | ccccgcttca | tctctgtggg | ctacgtggac | gacacccagt | tcgtgcgctt | 600 |
| cgacaacgac | gccgcgagtc | cgaggatggt | gccgcgggcg | ccgtggatgg | agcaggaggg | 660 |
| gtcagagtat | tgggaccggg | agacacggag | cgccagggac | accgcacaga | ttttccgagt | 720 |
| gaacctgcgg | acgctgcgcg | gctactacaa | tcagagcgag | gccggtgagt | gaccccggcc | 780 |
| aggggagcag | gtcacgaccc | ctcccatcc | cccacggacg | gcgcgggtcc | cctcgaatct | 840 |
| tcgggtccca | gattcacccc | aaggctgcgg | aacccgccca | gacctagac | cggggagagt | 900 |
| ctcaggcgcc | tttaccccggt | tctttttcag | tttaggccaa | aatgcccaca | gggtggtggc | 960 |
| gacgggggcg | gggcttggtg | ggcgggactg | actaaggggc | | | 1000 |

<210> SEQ ID NO 3
<211> LENGTH: 358
<212> TYPE: PRT
<213> ORGANISM: Homo sapiens

<400> SEQUENCE: 3

Met Val Asp Gly Thr Leu Leu Leu Leu Ser Glu Ala Leu Ala Leu
1               5                   10                  15

Thr Gln Thr Trp Ala Gly Ser His Ser Leu Lys Tyr Phe His Thr Ser
            20                  25                  30

Val Ser Arg Pro Gly Arg Gly Glu Pro Arg Phe Ile Ser Val Gly Tyr
            35                  40                  45

Val Asp Asp Thr Gln Phe Val Arg Phe Asp Asn Asp Ala Ala Ser Pro
        50                  55                  60

Arg Met Val Pro Arg Ala Pro Trp Met Glu Gln Glu Gly Ser Glu Tyr
65                  70                  75                  80

Trp Asp Arg Glu Thr Arg Ser Ala Arg Asp Thr Ala Gln Ile Phe Arg
                85                  90                  95

Val Asn Leu Arg Thr Leu Arg Gly Tyr Tyr Asn Gln Ser Glu Ala Gly
            100                 105                 110

Ser His Thr Leu Gln Trp Met His Gly Cys Glu Leu Gly Pro Asp Arg
        115                 120                 125

Arg Phe Leu Arg Gly Tyr Glu Gln Phe Ala Tyr Asp Gly Lys Asp Tyr
    130                 135                 140

Leu Thr Leu Asn Glu Asp Leu Arg Ser Trp Thr Ala Val Asp Thr Ala
145                 150                 155                 160

Ala Gln Ile Ser Glu Gln Lys Ser Asn Asp Ala Ser Glu Ala Glu His
                165                 170                 175

Gln Arg Ala Tyr Leu Glu Asp Thr Cys Val Glu Trp Leu His Lys Tyr
            180                 185                 190

Leu Glu Lys Gly Lys Glu Thr Leu Leu His Leu Glu Pro Pro Lys Thr
        195                 200                 205

His Val Thr His His Pro Ile Ser Asp His Glu Ala Thr Leu Arg Cys
    210                 215                 220

Trp Ala Leu Gly Phe Tyr Pro Ala Glu Ile Thr Leu Thr Trp Gln Gln
225                 230                 235                 240

Asp Gly Glu Gly His Thr Gln Asp Thr Glu Leu Val Glu Thr Arg Pro
                245                 250                 255

Ala Gly Asp Gly Thr Phe Gln Lys Trp Ala Ala Val Val Val Pro Ser
            260                 265                 270

Gly Glu Glu Gln Arg Tyr Thr Cys His Val Gln His Glu Gly Leu Pro
        275                 280                 285

Glu Pro Val Thr Leu Arg Trp Lys Pro Ala Ser Gln Pro Thr Ile Pro
    290                 295                 300

Ile Val Gly Ile Ile Ala Gly Leu Val Leu Gly Ser Val Val Ser
305                 310                 315                 320

Gly Ala Val Val Ala Ala Val Ile Trp Arg Lys Lys Ser Ser Gly Gly
                325                 330                 335

Lys Gly Gly Ser Tyr Ser Lys Ala Glu Trp Ser Asp Ser Ala Gln Gly
            340                 345                 350

Ser Glu Ser His Ser Leu
        355

<210> SEQ ID NO 4
<211> LENGTH: 1000
<212> TYPE: DNA
<213> ORGANISM: Homo sapiens

<400> SEQUENCE: 4

| | | | | | |
|---|---|---|---|---|---|
| aagtccccat | ccggactcaa | gaagttctca | ggactcagag | gctgggatca | tggtagatgg | 60 |
| aaccctcctt | ttactcctct | cggaggccct | ggcccttacc | cagacctggg | cgggtgagtg | 120 |
| cggggtcggg | atggaaacgg | cctctaccgg | gagtagagag | gggccggccc | ggcgggggcg | 180 |
| aaggactcgg | ggagccgcgc | cgggaggagg | gtcgggccga | tctcagcccc | tcctcgcccc | 240 |
| caggctccca | ctccttgaag | tatttccaca | cttccgtgtc | ccggcccggc | cgcggggagc | 300 |
| cccgcttcat | ctctgtgggc | tacgtggacg | acacccagtt | cgtgcgcttc | gacaacgacg | 360 |
| ccgcgagtcc | gaggatggtg | ccgcgggcgc | cgtggatgga | gcaggagggg | tcagagtatt | 420 |
| gggaccggga | gacacggagc | gccagggaca | ccgcacagat | tttccgagtg | aacctgcgga | 480 |
| cgctgcgcgg | ctactacaat | cagagcgagg | ccggtgagtg | accccggcca | ggggagcagg | 540 |
| tcacgacccc | tccccatccc | ccacggacgg | cgcgggtccc | ctcgaatctt | cgggtcccag | 600 |
| attcacccca | aggctgcgga | acccgcccag | accctagacc | ggggagagtc | tcaggcgcct | 660 |
| ttacccggtt | cttttcagt | ttaggccaaa | atgcccacag | ggtggtggcg | acggggggcgg | 720 |
| ggcttggtgg | gcgggactga | ctaaggggcg | gggccaggt | ctcacaccct | gcagtggatg | 780 |
| catggctgcg | agctggggcc | cgacaggcgc | ttcctccgcg | gtatgaaca | gttcgcctac | 840 |
| gacggcaagg | attatctcac | cctgaatgag | gacctgcgct | cctggaccgc | ggtggacacg | 900 |
| gcggctcaga | tctccgagca | aaagtcaaat | gatgcctctg | aggcggagca | ccagagagcc | 960 |
| tacctggaag | acacatgcgt | ggagtggctc | cacaaatacc | | | 1000 |

<210> SEQ ID NO 5
<211> LENGTH: 358
<212> TYPE: PRT
<213> ORGANISM: Homo sapiens

<400> SEQUENCE: 5

Met Val Asp Gly Thr Leu Leu Leu Leu Ser Glu Ala Leu Ala Leu
1               5                   10                  15

Thr Gln Thr Trp Ala Gly Ser His Ser Leu Lys Tyr Phe His Thr Ser
                20                  25                  30

Val Ser Arg Pro Gly Arg Gly Glu Pro Arg Phe Ile Ser Val Gly Tyr
            35                  40                  45

Val Asp Asp Thr Gln Phe Val Arg Phe Asp Asn Asp Ala Ala Ser Pro
        50                  55                  60

Arg Met Val Pro Arg Ala Pro Trp Met Glu Gln Glu Gly Ser Glu Tyr
65                  70                  75                  80

Trp Asp Arg Glu Thr Arg Ser Ala Arg Asp Thr Ala Gln Ile Phe Arg
                85                  90                  95

Val Asn Leu Arg Thr Leu Arg Gly Tyr Tyr Asn Gln Ser Glu Ala Gly
            100                 105                 110

Ser His Thr Leu Gln Trp Met His Gly Cys Glu Leu Gly Pro Asp Gly
        115                 120                 125

Arg Phe Leu Arg Gly Tyr Glu Gln Phe Ala Tyr Asp Gly Lys Asp Tyr
130                 135                 140

Leu Thr Leu Asn Glu Asp Leu Arg Ser Trp Thr Ala Val Asp Thr Ala
145                 150                 155                 160

```
Ala Gln Ile Ser Glu Gln Lys Ser Asn Asp Ala Ser Glu Ala Glu His
            165                 170                 175

Gln Arg Ala Tyr Leu Glu Asp Thr Cys Val Glu Trp Leu His Lys Tyr
        180                 185                 190

Leu Glu Lys Gly Lys Glu Thr Leu Leu His Leu Glu Pro Pro Lys Thr
        195                 200                 205

His Val Thr His His Pro Ile Ser Asp His Glu Ala Thr Leu Arg Cys
        210                 215                 220

Trp Ala Leu Gly Phe Tyr Pro Ala Glu Ile Thr Leu Thr Trp Gln Gln
225                 230                 235                 240

Asp Gly Glu Gly His Thr Gln Asp Thr Glu Leu Val Glu Thr Arg Pro
                245                 250                 255

Ala Gly Asp Gly Thr Phe Gln Lys Trp Ala Ala Val Val Val Pro Ser
            260                 265                 270

Gly Glu Glu Gln Arg Tyr Thr Cys His Val Gln His Glu Gly Leu Pro
        275                 280                 285

Glu Pro Val Thr Leu Arg Trp Lys Pro Ala Ser Gln Pro Thr Ile Pro
        290                 295                 300

Ile Val Gly Ile Ile Ala Gly Leu Val Leu Leu Gly Ser Val Val Ser
305                 310                 315                 320

Gly Ala Val Val Ala Ala Val Ile Trp Arg Lys Lys Ser Ser Gly Gly
                325                 330                 335

Lys Gly Gly Ser Tyr Ser Lys Ala Glu Trp Ser Asp Ser Ala Gln Gly
            340                 345                 350

Ser Glu Ser His Ser Leu
        355

<210> SEQ ID NO 6
<211> LENGTH: 1000
<212> TYPE: DNA
<213> ORGANISM: Homo sapiens

<400> SEQUENCE: 6
aagttctcag gactcagagg ctgggatcat ggtagatgga accctccttt tactcctctc      60
ggaggccctg gcccttaccc agacctgggc gggtgagtgc ggggtcggga tggaaacggc     120
ctctaccggg agtagagagg ggccggcccg gcggggcgga aggactcggg gagccgcgcc     180
gggaggaggg tcgggccgat ctcagcccct cctcgccccc aggctccacc tccttgaagt     240
atttccacac ttccgtgtcc cggcccggcc gcggggagcc ccgcttcatc tctgtgggct     300
acgtggacga cacccagttc gtgcgcttcg acaacgacgc cgcgagtccg aggatggtgc     360
cgcgggcgcc gtggatggag caggaggggt cagagtattg ggaccgggag acacggagcg     420
ccagggacac cgcacagatt ttccgagtga acctgcggac gctgcgcggc tactacaatc     480
agagcgaggc cggtgagtga ccccggccag gggagcaggt cacgacccct ccccatcccc     540
cacgacggcg cgggtcccc tcgaatcttc gggtcccaga ttcacccccaa ggctgcggaa     600 cccgcccaga ccctagaccg gggagagtct caggcgcctt acccggttc tttttcagtt     660 taggccaaaa tgcccacagg gtggtggcga cggggcggg gcttggtggg cgggactgac     720
taaggggcgg ggccagggtc tcacaccctg cagtggatgc atggctgcga gctgggccc     780 gacgggcgct tcctccgcgg gtatgaacag ttcgcctacg acggcaagga ttatctcacc     840
ctgaatgagg acctgcgctc ctggaccgcg gtggacacgg cggctcagat ctccgagcaa     900
aagtcaaatg atgcctctga ggcggagcac cagagagcct acctggaaga cacatgcgtg     960
```
gagtggctcc acaaatacct ggagaagggg aaggagacgc　　　　　　　　　　　　1000

<210> SEQ ID NO 7
<211> LENGTH: 358
<212> TYPE: PRT
<213> ORGANISM: Homo sapiens

<400> SEQUENCE: 7

```
Met Val Asp Gly Thr Leu Leu Leu Leu Ser Glu Ala Leu Ala Leu
1               5                   10                  15

Thr Gln Thr Trp Ala Gly Ser His Ser Leu Lys Tyr Phe His Thr Ser
            20                  25                  30

Val Ser Arg Pro Gly Arg Gly Glu Pro Arg Phe Ile Ser Val Gly Tyr
        35                  40                  45

Val Asp Asp Thr Gln Phe Val Arg Phe Asp Asn Asp Ala Ala Ser Pro
    50                  55                  60

Arg Met Val Pro Arg Ala Pro Trp Met Glu Gln Glu Gly Ser Glu Tyr
65                  70                  75                  80

Trp Asp Arg Glu Thr Arg Ser Ala Arg Asp Thr Ala Gln Ile Phe Arg
                85                  90                  95

Val Asn Leu Arg Thr Leu Arg Gly Tyr Tyr Asn Gln Ser Glu Ala Gly
            100                 105                 110

Ser His Thr Leu Gln Trp Met His Gly Cys Glu Leu Gly Pro Asp Gly
        115                 120                 125

Arg Phe Leu Arg Gly Tyr Glu Gln Phe Ala Tyr Asp Gly Lys Asp Tyr
    130                 135                 140

Leu Thr Leu Asn Glu Asp Leu Arg Ser Trp Thr Ala Val Asp Thr Ala
145                 150                 155                 160

Ala Gln Ile Ser Glu Gln Lys Ser Asn Asp Ala Ser Glu Ala Glu His
                165                 170                 175

Gln Arg Ala Tyr Leu Glu Asp Thr Cys Val Glu Trp Leu His Lys Tyr
            180                 185                 190

Leu Glu Lys Gly Lys Glu Thr Leu Leu His Leu Glu Pro Pro Lys Thr
        195                 200                 205

His Val Thr His His Pro Ile Ser Asp His Glu Ala Thr Leu Arg Cys
    210                 215                 220

Trp Ala Leu Gly Phe Tyr Pro Ala Glu Ile Thr Leu Thr Trp Gln Gln
225                 230                 235                 240

Asp Gly Glu Gly His Thr Gln Asp Thr Glu Leu Val Glu Thr Arg Pro
                245                 250                 255

Ala Gly Asp Gly Thr Phe Gln Lys Trp Ala Ala Val Val Pro Ser
            260                 265                 270

Gly Glu Glu Gln Arg Tyr Thr Cys His Val Gln His Glu Gly Leu Pro
        275                 280                 285

Glu Pro Val Thr Leu Arg Trp Lys Pro Ala Ser Gln Pro Thr Ile Pro
    290                 295                 300

Ile Val Gly Ile Ile Ala Gly Leu Val Leu Leu Gly Ser Val Val Ser
305                 310                 315                 320

Gly Ala Val Val Ala Ala Val Ile Trp Arg Lys Lys Ser Ser Gly Gly
                325                 330                 335

Lys Gly Gly Ser Tyr Ser Lys Ala Glu Trp Ser Asp Ser Ala Gln Gly
            340                 345                 350

Ser Glu Ser His Ser Leu
        355
```

<210> SEQ ID NO 8
<211> LENGTH: 1170
<212> TYPE: DNA
<213> ORGANISM: Homo sapiens

<400> SEQUENCE: 8

```
gttcgttgca acaaattgat gagcaatgct tttttataat gccaactttg tacaaaaaag    60
ttggcatggc gccccgaagc ctcctcctgc tgctctcagg ggccctggcc ctgaccgata   120
cttgggcagg ctcccactcc ttgaggtatt tcagcaccgc tgtgtcgcgg cccggccgcg   180
gggagccccg ctacatcgcc gtggagtacg tagacgacac gcaattcctg cggttcgaca   240
gcgacgccgc gattccgagg atggagccgc gggagccgtg ggtggagcaa gagggccgc    300
agtattggga gtggaccaca gggtacgcca aggccaacgc acagactgac cgagtggccc   360
tgaggaacct gctccgccgc tacaaccaga gcgaggctgg gtctcacacc ctccagggaa   420
tgaatggctg cgacatgggg cccgacggac gcctcctccg cgggtatcac cagcacgcgt   480
acgacggcaa ggattacatc tccctgaacg aggacctgcg ctcctggacc gcggcggaca   540
ccgtggctca gatcacccag cgcttctatg aggcagagga atatgcagag gagttcagga   600
cctacctgga gggcgagtgc ctggagttgc tccgcagata cttggagaat gggaaggaga   660
cgctacagcg cgcagatcct ccaaaggcac acgttgccca ccaccccatc tctgaccatg   720
aggccaccct gaggtgctgg gccctgggct tctaccctgc ggagatcacg ctgacctggc   780
agcgggatgg ggaggaacag acccaggaca cagagcttgt ggagaccagg cctgcagggg   840
atggaacctt ccagaagtgg gccgctgtgg tggtgccttc tggagaggaa cagagataca   900
catgccatgt gcagcacgag gggctgcccc agcccctcat cctgagatgg gagcagtctc   960
cccagcccac catccccatc gtgggcatcg ttgctggcct tgttgtcctt ggagctgtgg  1020
tcactggagc tgtggtcgct gctgtgatgt ggaggaagaa gagctcagat agaaacagag  1080
ggagctactc tcaggctgca gtgtgcccaa ctttcttgta caaagttggc attataagaa  1140
agcattgctt atcaatttgt tgcaacgaac                                   1170
```

<210> SEQ ID NO 9
<211> LENGTH: 346
<212> TYPE: PRT
<213> ORGANISM: Homo sapiens

<400> SEQUENCE: 9

```
Met Ala Pro Arg Ser Leu Leu Leu Leu Ser Gly Ala Leu Ala Leu
1               5                   10                  15

Thr Asp Thr Trp Ala Gly Ser His Ser Leu Arg Tyr Phe Ser Thr Ala
                20                  25                  30

Val Ser Arg Pro Gly Arg Gly Glu Pro Arg Tyr Ile Ala Val Glu Tyr
            35                  40                  45

Val Asp Asp Thr Gln Phe Leu Arg Phe Asp Ser Asp Ala Ala Ile Pro
        50                  55                  60

Arg Met Glu Pro Arg Glu Pro Trp Val Glu Gln Gly Pro Gln Tyr
65                  70                  75                  80

Trp Glu Trp Thr Thr Gly Tyr Ala Lys Ala Asn Ala Gln Thr Asp Arg
                85                  90                  95

Val Ala Leu Arg Asn Leu Leu Arg Arg Tyr Asn Gln Ser Glu Ala Gly
            100                 105                 110

Ser His Thr Leu Gln Gly Met Asn Gly Cys Asp Met Gly Pro Asp Gly
        115                 120                 125
```

```
Arg Leu Leu Arg Gly Tyr His Gln His Ala Tyr Asp Gly Lys Asp Tyr
            130                 135                 140

Ile Ser Leu Asn Glu Asp Leu Arg Ser Trp Thr Ala Ala Asp Thr Val
145                 150                 155                 160

Ala Gln Ile Thr Gln Arg Phe Tyr Glu Ala Glu Glu Tyr Ala Glu Glu
            165                 170                 175

Phe Arg Thr Tyr Leu Glu Gly Glu Cys Leu Glu Leu Leu Arg Arg Tyr
            180                 185                 190

Leu Glu Asn Gly Lys Glu Thr Leu Gln Arg Ala Asp Pro Pro Lys Ala
            195                 200                 205

His Val Ala His His Pro Ile Ser Asp His Glu Ala Thr Leu Arg Cys
            210                 215                 220

Trp Ala Leu Gly Phe Tyr Pro Ala Glu Ile Thr Leu Thr Trp Gln Arg
225                 230                 235                 240

Asp Gly Glu Glu Gln Thr Gln Asp Thr Glu Leu Val Glu Thr Arg Pro
            245                 250                 255

Ala Gly Asp Gly Thr Phe Gln Lys Trp Ala Ala Val Val Val Pro Ser
            260                 265                 270

Gly Glu Glu Gln Arg Tyr Thr Cys His Val Gln His Glu Gly Leu Pro
            275                 280                 285

Gln Pro Leu Ile Leu Arg Trp Glu Gln Ser Pro Gln Pro Thr Ile Pro
            290                 295                 300

Ile Val Gly Ile Val Ala Gly Leu Val Val Leu Gly Ala Val Val Thr
305                 310                 315                 320

Gly Ala Val Val Ala Ala Val Met Trp Arg Lys Lys Ser Ser Asp Arg
            325                 330                 335

Asn Arg Gly Ser Tyr Ser Gln Ala Ala Val
            340                 345

<210> SEQ ID NO 10
<211> LENGTH: 1041
<212> TYPE: DNA
<213> ORGANISM: Homo sapiens

<400> SEQUENCE: 10
atggcgcccc gaagcctcct cctgctgctc tcaggggccc tggccctgac cgatacttgg     60
gcaggctccc actccttgag gtatttcagc accgctgtgt cgcggcccgg ccgcggggag    120
ccccgctaca tcgccgtgga gtacgtagac gacacgcaat tcctgcggtt cgacagcgac    180
gccgcgattc cgaggatgga gccgcgggag ccgtgggtgg agcaagaggg gccgcagtat    240
tgggagtgga ccacagggta cgccaaggcc aacgcacaga ctgaccgagt ggccctgagg    300
aacctgctcc gccgctacaa ccagagcgag gctgggtctc acccctcca gggaatgaat    360 ggctgcgaca tggggcccga cggacgcctc ctccgcgggt atcaccagca cgcgtacgac    420
ggcaaggatt acatctccct gaacgaggac ctgcgctcct ggaccgcggc ggacaccgtg    480
gctcagatca cccagcgctt ctatgaggca gaggaatatg cagaggagtt caggacctac    540
ctggagggcg agtgcctgga gttgctccgc agatacttgg agaatgggaa ggagacgcta    600
cagcgcgcag atcctccaaa ggcacacgtt gccaccacc ccatctctga ccatgaggcc    660
accctgaggt gctgggccct gggcttctac cctgcggaga tcacgctgac ctggcagcgg    720
gatggggagg aacagaccca ggacacagag cttgtggaga ccaggcctgc aggggatgga    780
accttccaga gtgggccgc tgtggtggtg ccttctggag aggaacagag atacacatgc    840
```

```
catgtgcagc acgaggggct gccccagccc ctcatcctga gatgggagca gtctccccag    900
cccaccatcc ccatcgtggg catcgttgct ggccttgttg tccttggagc tgtggtcact    960
ggagctgtgg tcgctgctgt gatgtggagg aagaagagct cagatagaaa cagagggagc   1020
tactctcagg ctgcagtgtg a                                              1041
```

<210> SEQ ID NO 11
<211> LENGTH: 346
<212> TYPE: PRT
<213> ORGANISM: Homo sapiens

<400> SEQUENCE: 11

```
Met Ala Pro Arg Ser Leu Leu Leu Leu Ser Gly Ala Leu Ala Leu
1               5                   10                  15

Thr Asp Thr Trp Ala Gly Ser His Ser Leu Arg Tyr Phe Ser Thr Ala
            20                  25                  30

Val Ser Arg Pro Gly Arg Gly Glu Pro Arg Tyr Ile Ala Val Glu Tyr
        35                  40                  45

Val Asp Asp Thr Gln Phe Leu Arg Phe Asp Ser Asp Ala Ala Ile Pro
    50                  55                  60

Arg Met Glu Pro Arg Glu Pro Trp Val Glu Gln Glu Gly Pro Gln Tyr
65                  70                  75                  80

Trp Glu Trp Thr Thr Gly Tyr Ala Lys Ala Asn Ala Gln Thr Asp Arg
                85                  90                  95

Val Ala Leu Arg Asn Leu Leu Arg Arg Tyr Asn Gln Ser Glu Ala Gly
            100                 105                 110

Ser His Thr Leu Gln Gly Met Asn Gly Cys Asp Met Gly Pro Asp Gly
        115                 120                 125

Arg Leu Leu Arg Gly Tyr His Gln His Ala Tyr Asp Gly Lys Asp Tyr
    130                 135                 140

Ile Ser Leu Asn Glu Asp Leu Arg Ser Trp Thr Ala Ala Asp Thr Val
145                 150                 155                 160

Ala Gln Ile Thr Gln Arg Phe Tyr Glu Ala Glu Glu Tyr Ala Glu Glu
                165                 170                 175

Phe Arg Thr Tyr Leu Glu Gly Glu Cys Leu Glu Leu Leu Arg Arg Tyr
            180                 185                 190

Leu Glu Asn Gly Lys Glu Thr Leu Gln Arg Ala Asp Pro Pro Lys Ala
        195                 200                 205

His Val Ala His His Pro Ile Ser Asp His Glu Ala Thr Leu Arg Cys
    210                 215                 220

Trp Ala Leu Gly Phe Tyr Pro Ala Glu Ile Thr Leu Thr Trp Gln Arg
225                 230                 235                 240

Asp Gly Glu Glu Gln Thr Gln Asp Thr Glu Leu Val Glu Thr Arg Pro
                245                 250                 255

Ala Gly Asp Gly Thr Phe Gln Lys Trp Ala Ala Val Val Val Pro Ser
            260                 265                 270

Gly Glu Glu Gln Arg Tyr Thr Cys His Val Gln His Glu Gly Leu Pro
        275                 280                 285

Gln Pro Leu Ile Leu Arg Trp Glu Gln Ser Pro Gln Pro Thr Ile Pro
    290                 295                 300

Ile Val Gly Ile Val Ala Gly Leu Val Val Leu Gly Ala Val Val Thr
305                 310                 315                 320

Gly Ala Val Val Ala Ala Val Met Trp Arg Lys Lys Ser Ser Asp Arg
                325                 330                 335
```

Asn Arg Gly Ser Tyr Ser Gln Ala Ala Val
        340                 345

<210> SEQ ID NO 12
<211> LENGTH: 1146
<212> TYPE: DNA
<213> ORGANISM: Homo sapiens

<400> SEQUENCE: 12

```
gttcgttgca acaaattgat gagcaatgct tttttataat gccaactttg tacaaaaaag    60
ttggcatggt ggtcatggca ccccgaaccc tcttcctgct actctcgggg gccctgaccc   120
tgaccgagac ctgggcgggc tcccactcca tgaggtattt cagcgccgcc gtgtcccggc   180
ccagccgcgg ggagccccgc ttcatcgcca tgggctacgt ggacgacacg cagttcgtgc   240
ggttcgacag cgactcggcg tgtccgagga tggagccgcg ggcgccgtgg gtggagcggg   300
agggccaga gtattgggaa gaggagacac ggaacaccaa ggcccacgca cagactgaca   360
gaatgaacct gcagaccctg cgcggctact acaaccagag cgaggccagt tctcataccc   420
tccagtggat gattggctgc gacctggggt ccgacggacg cctcctccgc gggtatgaac   480
agtatgccta cgatggcaag gattacctcg ccctgaacga ggacctgcgc tcctggaccg   540
cagcggacac tgcggctcag atctccaagc gcaagtgtga ggcggccaat gtggctgaac   600
aaaggagagc ctacctggag ggcacgtgcg tggagtggct ccacagatac ctggagaacg   660
ggaaggagat gctgcagcgc gcggaccccc ccaagacaca cgtgacccac cccctgtctc   720
ttgactatga ggccaccctg aggtgctggg ccctgggctt ctaccctgcg agatcatac   780
tgacctggca gcgggatggg gaggaccaga cccaggacgt ggagctcgtg gagaccaagc   840
ctgcagggga tggaaccttc cagaagtggg cagctgtggt ggtgccttct ggagaggagc   900
agagatacat gtgccatgtg cagcatgagg ggctgccgga gcccctcatg ctgagatgga   960
agcagtcttc cctgcccacc atccccatca tgggtatcgt tgctggtctg gttgtccttg  1020
cagctgtagt cactggagct gcggtcgctg ctgtgctgtg gaggaagaag agctcagatt  1080
gcccaacttt cttgtacaaa gttggcatta taagaaagca ttgcttatca atttgttgca  1140
acgaac                                                            1146
```

<210> SEQ ID NO 13
<211> LENGTH: 338
<212> TYPE: PRT
<213> ORGANISM: Homo sapiens

<400> SEQUENCE: 13

Met Val Val Met Ala Pro Arg Thr Leu Phe Leu Leu Leu Ser Gly Ala
1               5                   10                  15

Leu Thr Leu Thr Glu Thr Trp Ala Gly Ser His Ser Met Arg Tyr Phe
                20                  25                  30

Ser Ala Ala Val Ser Arg Pro Ser Arg Gly Glu Pro Arg Phe Ile Ala
            35                  40                  45

Met Gly Tyr Val Asp Asp Thr Gln Phe Val Arg Phe Asp Ser Asp Ser
        50                  55                  60

Ala Cys Pro Arg Met Glu Pro Arg Ala Pro Trp Val Glu Arg Glu Gly
65                  70                  75                  80

Pro Glu Tyr Trp Glu Glu Glu Thr Arg Asn Thr Lys Ala His Ala Gln
                85                  90                  95

Thr Asp Arg Met Asn Leu Gln Thr Leu Arg Gly Tyr Tyr Asn Gln Ser
            100                 105                 110

Glu Ala Ser Ser His Thr Leu Gln Trp Met Ile Gly Cys Asp Leu Gly
            115                 120                 125

Ser Asp Gly Arg Leu Leu Arg Gly Tyr Glu Gln Tyr Ala Tyr Asp Gly
    130                 135                 140

Lys Asp Tyr Leu Ala Leu Asn Glu Asp Leu Arg Ser Trp Thr Ala Ala
145                 150                 155                 160

Asp Thr Ala Ala Gln Ile Ser Lys Arg Lys Cys Glu Ala Ala Asn Val
                165                 170                 175

Ala Glu Gln Arg Arg Ala Tyr Leu Glu Gly Thr Cys Val Glu Trp Leu
            180                 185                 190

His Arg Tyr Leu Glu Asn Gly Lys Glu Met Leu Gln Arg Ala Asp Pro
        195                 200                 205

Pro Lys Thr His Val Thr His His Pro Val Phe Asp Tyr Glu Ala Thr
    210                 215                 220

Leu Arg Cys Trp Ala Leu Gly Phe Tyr Pro Ala Glu Ile Ile Leu Thr
225                 230                 235                 240

Trp Gln Arg Asp Gly Glu Asp Gln Thr Gln Asp Val Glu Leu Val Glu
                245                 250                 255

Thr Lys Pro Ala Gly Asp Gly Thr Phe Gln Lys Trp Ala Ala Val Val
            260                 265                 270

Val Pro Ser Gly Glu Glu Gln Arg Tyr Met Cys His Val Gln His Glu
        275                 280                 285

Gly Leu Pro Glu Pro Leu Met Leu Arg Trp Lys Gln Ser Ser Leu Pro
    290                 295                 300

Thr Ile Pro Ile Met Gly Ile Val Ala Gly Leu Val Val Leu Ala Ala
305                 310                 315                 320

Val Val Thr Gly Ala Ala Val Ala Ala Val Leu Trp Arg Lys Lys Ser
                325                 330                 335

Ser Asp

<210> SEQ ID NO 14
<211> LENGTH: 1475
<212> TYPE: DNA
<213> ORGANISM: Homo sapiens

<400> SEQUENCE: 14
agtgtggtac tttgtcttga ggagatgtcc tggactcaca cggaaactta gggctacgga      60
atgaagacgc caaggatggt ggtcatggcg ccccgaaccc tcttcctgct gctctcgggg     120
gccctgaccc tgaccgagac ctgggcgggc tcccactcca tgaggtattt cagcgccgcc     180
gtgtcccggc ccggccgcgg ggagccccgc ttcatcgcca tgggctacgt ggacgacacg     240
cagttcgtgc ggttcgacag cgactcggcg tgtccgagga tggagccgcg ggcgccgtgg     300
gtggagcagg aggggccgga gtattgggaa gaggagacac ggaacaccaa gcccacgca      360 cagactgaca gaatgaacct gcagaccctg cgcggctact acaaccagag cgaggccagt     420
tctcacaccc tccagtggat gattggctgc gacctggggt ccgacggacg cctcctccgc     480
gggtatgaac agtatgccta cgatggcaag gattacctcg ccctgaacga ggacctgcgc     540
tcctggaccg cagcggacac tgcggctcag atctccaagc gcaagtgtga ggcggccaat     600
gtggctgaac aaaggagagc ctacctggag ggcacgtgcg tggagtggct ccacagatac     660
ctggagaacg gaaggagat gctgcagcgc gcggaccccc ccaagacaca cgtgacccac     720
caccctgtct ttgactatga ggccaccctg aggtgctggg ccctgggctt ctaccctgcg     780

-continued

```
gagatcatac tgacctggca gcgggatggg gaggaccaga cccaggacgt ggagctcgtg    840
gagaccaggc ctgcagggga tggaaccttc cagaagtggg cagctgtggt ggtgccttct    900
ggagaggagc agagatacac gtgccatgtg cagcatgagg ggctgccgga gcccctcatg    960
ctgagatgga agcagtcttc cctgcccacc atccccatca tgggtatcgt tgctggcctg   1020
gttgtccttg cagctgtagt cactggagct gcggtcgctg ctgtgctgtg agaaagaag    1080 agctcagatt gaaaggagg gagctactct caggctgcaa tgtgaaacag ctgccctgtg   1140
tgggactgag tggcaagtcc ctttgtgact tcaagaaccc tgactcctct ttgtgcagag   1200
accagcccac ccctgtgccc accatgaccc tcttcctcat gctgaactgc attccttccc   1260
caatcacctt tcctgttcca gaaaagggc tgggatgtct ccgtctctgt ctcaaatttg   1320
tggtccactg agctataact tacttctgta ttaaaattag aatctgagta taaatttact   1380
ttttcaaatt atttccaaga gagattgatg ggttaattaa aggagaagat tcctgaaatt   1440
tgagagacaa aataaatgga agacatgaga acttt                              1475
```

<210> SEQ ID NO 15
<211> LENGTH: 343
<212> TYPE: PRT
<213> ORGANISM: Homo sapiens

<400> SEQUENCE: 15

```
Met Lys Thr Pro Arg Met Val Val Met Ala Pro Arg Thr Leu Phe Leu
1               5                   10                  15

Leu Leu Ser Gly Ala Leu Thr Leu Thr Glu Thr Trp Ala Gly Ser His
            20                  25                  30

Ser Met Arg Tyr Phe Ser Ala Ala Val Ser Arg Pro Gly Arg Gly Glu
        35                  40                  45

Pro Arg Phe Ile Ala Met Gly Tyr Val Asp Asp Thr Gln Phe Val Arg
    50                  55                  60

Phe Asp Ser Asp Ser Ala Cys Pro Arg Met Glu Pro Arg Ala Pro Trp
65                  70                  75                  80

Val Glu Gln Glu Gly Pro Glu Tyr Trp Glu Glu Thr Arg Asn Thr
                85                  90                  95

Lys Ala His Ala Gln Thr Asp Arg Met Asn Leu Gln Thr Leu Arg Gly
            100                 105                 110

Tyr Tyr Asn Gln Ser Glu Ala Ser Ser His Thr Leu Gln Trp Met Ile
        115                 120                 125

Gly Cys Asp Leu Gly Ser Asp Gly Arg Leu Leu Arg Gly Tyr Glu Gln
    130                 135                 140

Tyr Ala Tyr Asp Gly Lys Asp Tyr Leu Ala Leu Asn Glu Asp Leu Arg
145                 150                 155                 160

Ser Trp Thr Ala Ala Asp Thr Ala Ala Gln Ile Ser Lys Arg Lys Cys
                165                 170                 175

Glu Ala Ala Asn Val Ala Glu Gln Arg Arg Ala Tyr Leu Glu Gly Thr
            180                 185                 190

Cys Val Glu Trp Leu His Arg Tyr Leu Glu Asn Gly Lys Glu Met Leu
        195                 200                 205

Gln Arg Ala Asp Pro Pro Lys Thr His Val Thr His His Pro Val Phe
    210                 215                 220

Asp Tyr Glu Ala Thr Leu Arg Cys Trp Ala Leu Gly Phe Tyr Pro Ala
225                 230                 235                 240

Glu Ile Ile Leu Thr Trp Gln Arg Asp Gly Glu Asp Gln Thr Gln Asp
                245                 250                 255
```

Val Glu Leu Val Glu Thr Arg Pro Ala Gly Asp Gly Thr Phe Gln Lys
            260                 265                 270

Trp Ala Ala Val Val Pro Ser Gly Glu Glu Gln Arg Tyr Thr Cys
            275                 280                 285

His Val Gln His Glu Gly Leu Pro Glu Pro Leu Met Leu Arg Trp Lys
            290                 295                 300

Gln Ser Ser Leu Pro Thr Ile Pro Ile Met Gly Ile Val Ala Gly Leu
305                 310                 315                 320

Val Val Leu Ala Ala Val Val Thr Gly Ala Ala Val Ala Ala Val Leu
                325                 330                 335

Trp Arg Lys Lys Ser Ser Asp
            340

<210> SEQ ID NO 16
<211> LENGTH: 1578
<212> TYPE: DNA
<213> ORGANISM: Homo sapiens

<400> SEQUENCE: 16

| | | | | | |
|---|---|---|---|---|---|
| agtgtggtac | tttgtcttga | ggagatgtcc | tggactcaca | cggaaactta | gggctacgga | 60 |
| atgaagttct | cactcccatt | aggtgacagg | tttttagaga | agccaatcag | cgtcgccgcg | 120 |
| gtcctggttc | taaagtcctc | gctcacccac | ccggactcat | tctccccaga | cgccaaggat | 180 |
| ggtggtcatg | gcgccccgaa | ccctcttcct | gctgctctcg | ggggccctga | ccctgaccga | 240 |
| gacctgggcg | gctcccact | ccatgaggta | tttcagcgcc | gccgtgtccc | ggcccggccg | 300 |
| cggggagccc | cgcttcatcg | ccatgggcta | cgtggacgac | acgcagttcg | tgcggttcga | 360 |
| cagcgactcg | cgtgtccga | ggatggagcc | gcgggcgccg | tgggtggagc | aggaggggcc | 420 |
| ggagtattgg | gaagaggaga | cacggaacac | caaggcccac | gcacagactg | acagaatgaa | 480 |
| cctgcagacc | ctgcgcggct | actacaacca | gagcgaggcc | agttctcaca | ccctccagtg | 540 |
| gatgattggc | tgcgacctgg | ggtccgacgg | acgcctcctc | cgcgggtatg | aacagtatgc | 600 |
| ctacgatggc | aaggattacc | tcgccctgaa | cgaggacctg | cgctcctgga | ccgcagcgga | 660 |
| cactgcggct | cagatctcca | agcgcaagtg | tgaggcggca | aatgtggctg | aacaaaggag | 720 |
| agcctacctg | agggcacgt | gcgtggagtg | gctccacaga | tacctggaga | cgggaagga | 780 |
| gatgctgcag | cgcgcggacc | cccccaagac | acacgtgacc | caccaccctg | tctttgacta | 840 |
| tgaggccacc | ctgaggtgct | gggccctggg | cttctaccct | gcggagatca | tactgacctg | 900 |
| gcagcgggat | ggggaggacc | agacccagga | cgtggagctc | gtggagacca | ggcctgcagg | 960 |
| ggatggaacc | ttccagaagt | gggcagctgt | ggtggtgcct | tctggagagg | agcagagata | 1020 |
| cacgtgccat | gtgcagcatg | aggggctgcc | ggagcccctc | atgctgagat | ggaagcagtc | 1080 |
| ttccctgccc | accatcccca | tcatgggtat | cgttgctggc | ctggttgtcc | ttgcagctgt | 1140 |
| agtcactgga | gctgcggtcg | ctgctgtgct | gtggagaaag | aagagctcag | attgaaaagg | 1200 |
| agggagctac | tctcaggctg | caatgtgaaa | cagctgccct | gtgtgggact | gagtggcaag | 1260 |
| tccctttgtg | acttcaagaa | ccctgactcc | tctttgtgca | gagaccagcc | cacccctgtg | 1320 |
| cccaccatga | ccctcttcct | catgctgaac | tgcattcctt | ccccaatcac | ctttcctgtt | 1380 |
| ccagaaaagg | ggctgggatg | tctccgtctc | tgtctcaaat | tgtggtccca | ctgagctata | 1440 |
| acttacttct | gtattaaaat | tagaatctga | gtataaattt | acttttcaa | attatttcca | 1500 |
| agagagattg | atgggttaat | taaggagaa | gattcctgaa | atttgagaga | caaaataaat | 1560 | ggaagacatg agaacttt                                              1578

<210> SEQ ID NO 17
<211> LENGTH: 338
<212> TYPE: PRT
<213> ORGANISM: Homo sapiens

<400> SEQUENCE: 17

Met Val Val Met Ala Pro Arg Thr Leu Phe Leu Leu Leu Ser Gly Ala
1               5                   10                  15

Leu Thr Leu Thr Glu Thr Trp Ala Gly Ser His Ser Met Arg Tyr Phe
            20                  25                  30

Ser Ala Ala Val Ser Arg Pro Gly Arg Gly Glu Pro Arg Phe Ile Ala
        35                  40                  45

Met Gly Tyr Val Asp Asp Thr Gln Phe Val Arg Phe Asp Ser Asp Ser
    50                  55                  60

Ala Cys Pro Arg Met Glu Pro Arg Ala Pro Trp Val Glu Gln Glu Gly
65                  70                  75                  80

Pro Glu Tyr Trp Glu Glu Thr Arg Asn Thr Lys Ala His Ala Gln
                85                  90                  95

Thr Asp Arg Met Asn Leu Gln Thr Leu Arg Gly Tyr Tyr Asn Gln Ser
            100                 105                 110

Glu Ala Ser Ser His Thr Leu Gln Trp Met Ile Gly Cys Asp Leu Gly
        115                 120                 125

Ser Asp Gly Arg Leu Leu Arg Gly Tyr Glu Gln Tyr Ala Tyr Asp Gly
    130                 135                 140

Lys Asp Tyr Leu Ala Leu Asn Glu Asp Leu Arg Ser Trp Thr Ala Ala
145                 150                 155                 160

Asp Thr Ala Ala Gln Ile Ser Lys Arg Lys Cys Glu Ala Ala Asn Val
                165                 170                 175

Ala Glu Gln Arg Arg Ala Tyr Leu Glu Gly Thr Cys Val Glu Trp Leu
            180                 185                 190

His Arg Tyr Leu Glu Asn Gly Lys Glu Met Leu Gln Arg Ala Asp Pro
        195                 200                 205

Pro Lys Thr His Val Thr His His Pro Val Phe Asp Tyr Glu Ala Thr
    210                 215                 220

Leu Arg Cys Trp Ala Leu Gly Phe Tyr Pro Ala Glu Ile Ile Leu Thr
225                 230                 235                 240

Trp Gln Arg Asp Gly Glu Asp Gln Thr Gln Asp Val Glu Leu Val Glu
                245                 250                 255

Thr Arg Pro Ala Gly Asp Gly Thr Phe Gln Lys Trp Ala Ala Val Val
            260                 265                 270

Val Pro Ser Gly Glu Glu Gln Arg Tyr Thr Cys His Val Gln His Glu
        275                 280                 285

Gly Leu Pro Glu Pro Leu Met Leu Arg Trp Lys Gln Ser Ser Leu Pro
    290                 295                 300

Thr Ile Pro Ile Met Gly Ile Val Ala Gly Leu Val Val Leu Ala Ala
305                 310                 315                 320

Val Val Thr Gly Ala Ala Val Ala Ala Val Leu Trp Arg Lys Lys Ser
                325                 330                 335

Ser Asp

<210> SEQ ID NO 18
<211> LENGTH: 9
<212> TYPE: PRT

```
<213> ORGANISM: Homo sapiens

<400> SEQUENCE: 18

Thr Leu Thr Val Thr Ser Thr Leu Pro
1               5

<210> SEQ ID NO 19
<211> LENGTH: 9
<212> TYPE: PRT
<213> ORGANISM: Homo sapiens

<400> SEQUENCE: 19

Thr Val Thr Ser Thr Leu Pro Val Gly
1               5

<210> SEQ ID NO 20
<211> LENGTH: 9
<212> TYPE: PRT
<213> ORGANISM: Homo sapiens

<400> SEQUENCE: 20

Val Thr His Pro His Leu Pro Arg Ala
1               5

<210> SEQ ID NO 21
<211> LENGTH: 9
<212> TYPE: PRT
<213> ORGANISM: Homo sapiens

<400> SEQUENCE: 21

Val Thr Ser Thr Leu Pro Val Gly Thr
1               5

<210> SEQ ID NO 22
<211> LENGTH: 9
<212> TYPE: PRT
<213> ORGANISM: Homo sapiens

<400> SEQUENCE: 22

Ala Ala Pro Glu Val Tyr Ala Phe Ala
1               5

<210> SEQ ID NO 23
<211> LENGTH: 9
<212> TYPE: PRT
<213> ORGANISM: Homo sapiens

<400> SEQUENCE: 23

Thr Ile Thr Cys Leu Val Val Asp Leu
1               5

<210> SEQ ID NO 24
<211> LENGTH: 9
<212> TYPE: PRT
<213> ORGANISM: Homo sapiens

<400> SEQUENCE: 24

Arg Ala Ala Pro Glu Val Tyr Ala Phe
1               5

<210> SEQ ID NO 25
<211> LENGTH: 9
<212> TYPE: PRT
<213> ORGANISM: Homo sapiens
```

```
<400> SEQUENCE: 25

Val Tyr Ala Phe Ala Thr Pro Glu Trp
1               5

<210> SEQ ID NO 26
<211> LENGTH: 9
<212> TYPE: PRT
<213> ORGANISM: Homo sapiens

<400> SEQUENCE: 26

Ala Pro Glu Val Tyr Ala Phe Ala Thr
1               5

<210> SEQ ID NO 27
<211> LENGTH: 9
<212> TYPE: PRT
<213> ORGANISM: Homo sapiens

<400> SEQUENCE: 27

Leu Thr Val Thr Ser Thr Leu Pro Val
1               5

<210> SEQ ID NO 28
<211> LENGTH: 9
<212> TYPE: PRT
<213> ORGANISM: Homo sapiens

<400> SEQUENCE: 28

Val Gln Arg Ala Val Ser Val Asn Pro
1               5

<210> SEQ ID NO 29
<211> LENGTH: 9
<212> TYPE: PRT
<213> ORGANISM: Homo sapiens

<400> SEQUENCE: 29

Thr Cys Leu Val Val Asp Leu Ala Pro
1               5

<210> SEQ ID NO 30
<211> LENGTH: 9
<212> TYPE: PRT
<213> ORGANISM: Homo sapiens

<400> SEQUENCE: 30

Pro Glu Val Tyr Ala Phe Ala Thr Pro
1               5

<210> SEQ ID NO 31
<211> LENGTH: 9
<212> TYPE: PRT
<213> ORGANISM: Homo sapiens

<400> SEQUENCE: 31

Cys Arg Val Thr His Pro His Leu Pro
1               5

<210> SEQ ID NO 32
<211> LENGTH: 9
<212> TYPE: PRT
<213> ORGANISM: Homo sapiens

<400> SEQUENCE: 32
```

```
Thr Tyr Thr Cys Gln Val Thr Tyr Gln
1               5

<210> SEQ ID NO 33
<211> LENGTH: 9
<212> TYPE: PRT
<213> ORGANISM: Homo sapiens

<400> SEQUENCE: 33

Val Thr Tyr Gln Gly His Thr Phe Glu
1               5

<210> SEQ ID NO 34
<211> LENGTH: 9
<212> TYPE: PRT
<213> ORGANISM: Homo sapiens

<400> SEQUENCE: 34

Thr Pro Pro Thr Val Lys Ile Leu Gln
1               5

<210> SEQ ID NO 35
<211> LENGTH: 9
<212> TYPE: PRT
<213> ORGANISM: Homo sapiens

<400> SEQUENCE: 35

Tyr Ala Phe Ala Thr Pro Glu Trp Pro
1               5

<210> SEQ ID NO 36
<211> LENGTH: 9
<212> TYPE: PRT
<213> ORGANISM: Homo sapiens

<400> SEQUENCE: 36

Gln Thr Val Gln Arg Ala Val Ser Val
1               5

<210> SEQ ID NO 37
<211> LENGTH: 9
<212> TYPE: PRT
<213> ORGANISM: Homo sapiens

<400> SEQUENCE: 37

Ala Ala Ser Pro Ser Gln Thr Val Gln
1               5

<210> SEQ ID NO 38
<211> LENGTH: 9
<212> TYPE: PRT
<213> ORGANISM: Homo sapiens

<400> SEQUENCE: 38

Ile Thr Cys Leu Val Val Asp Leu Ala
1               5

<210> SEQ ID NO 39
<211> LENGTH: 9
<212> TYPE: PRT
<213> ORGANISM: Homo sapiens

<400> SEQUENCE: 39

Thr Val Gln Arg Ala Val Ser Val Asn
1               5
```

<210> SEQ ID NO 40
<211> LENGTH: 9
<212> TYPE: PRT
<213> ORGANISM: Homo sapiens

<400> SEQUENCE: 40

Phe Thr Pro Pro Thr Val Lys Ile Leu
1               5

<210> SEQ ID NO 41
<211> LENGTH: 9
<212> TYPE: PRT
<213> ORGANISM: Homo sapiens

<400> SEQUENCE: 41

Gln Val Thr Tyr Gln Gly His Thr Phe
1               5

<210> SEQ ID NO 42
<211> LENGTH: 9
<212> TYPE: PRT
<213> ORGANISM: Homo sapiens

<400> SEQUENCE: 42

Pro Pro Thr Val Lys Ile Leu Gln Ser
1               5

<210> SEQ ID NO 43
<211> LENGTH: 428
<212> TYPE: PRT
<213> ORGANISM: Homo sapiens

<400> SEQUENCE: 43

Ala Ser Thr Gln Ser Pro Ser Val Phe Pro Leu Thr Arg Cys Cys Lys
1               5                   10                  15

Asn Ile Pro Ser Asn Ala Thr Ser Val Thr Leu Gly Cys Leu Ala Thr
            20                  25                  30

Gly Tyr Phe Pro Glu Pro Val Met Val Thr Trp Asp Thr Gly Ser Leu
        35                  40                  45

Asn Gly Thr Thr Met Thr Leu Pro Ala Thr Thr Leu Thr Leu Ser Gly
    50                  55                  60

His Tyr Ala Thr Ile Ser Leu Leu Thr Val Ser Gly Ala Trp Ala Lys
65                  70                  75                  80

Gln Met Phe Thr Cys Arg Val Ala His Thr Pro Ser Ser Thr Asp Trp
                85                  90                  95

Val Asp Asn Lys Thr Phe Ser Val Cys Ser Arg Asp Phe Thr Pro Pro
            100                 105                 110

Thr Val Lys Ile Leu Gln Ser Ser Cys Asp Gly Gly Gly His Phe Pro
        115                 120                 125

Pro Thr Ile Gln Leu Leu Cys Leu Val Ser Gly Tyr Thr Pro Gly Thr
    130                 135                 140

Ile Asn Ile Thr Trp Leu Glu Asp Gly Gln Val Met Asp Val Asp Leu
145                 150                 155                 160

Ser Thr Ala Ser Thr Thr Gln Glu Gly Glu Leu Ala Ser Thr Gln Ser
                165                 170                 175

Glu Leu Thr Leu Ser Gln Lys His Trp Leu Ser Asp Arg Thr Tyr Thr
            180                 185                 190

Cys Gln Val Thr Tyr Gln Gly His Thr Phe Glu Asp Ser Thr Lys Lys

```
            195                 200                 205
    Cys Ala Asp Ser Asn Pro Arg Gly Val Ser Ala Tyr Leu Ser Arg Pro
        210                 215                 220

Ser Pro Phe Asp Leu Phe Ile Arg Lys Ser Pro Thr Ile Thr Cys Leu
    225                 230                 235                 240

Val Val Asp Leu Ala Pro Ser Lys Gly Thr Val Asn Leu Thr Trp Ser
                    245                 250                 255

Arg Ala Ser Gly Lys Pro Val Asn His Ser Thr Arg Lys Glu Glu Lys
                260                 265                 270

Gln Arg Asn Gly Thr Leu Thr Val Thr Ser Thr Leu Pro Val Gly Thr
            275                 280                 285

Arg Asp Trp Ile Glu Gly Glu Thr Tyr Gln Cys Arg Val Thr His Pro
        290                 295                 300

His Leu Pro Arg Ala Leu Met Arg Ser Thr Thr Lys Thr Ser Gly Pro
    305                 310                 315                 320

Arg Ala Ala Pro Glu Val Tyr Ala Phe Ala Thr Pro Glu Trp Pro Gly
                    325                 330                 335

Ser Arg Asp Lys Arg Thr Leu Ala Cys Leu Ile Gln Asn Phe Met Pro
                340                 345                 350

Glu Asp Ile Ser Val Gln Trp Leu His Asn Glu Val Gln Leu Pro Asp
            355                 360                 365

Ala Arg His Ser Thr Thr Gln Pro Arg Lys Thr Lys Gly Ser Gly Phe
        370                 375                 380

Phe Val Phe Ser Arg Leu Glu Val Thr Arg Ala Glu Trp Glu Gln Lys
    385                 390                 395                 400

Asp Glu Phe Ile Cys Arg Ala Val His Glu Ala Ala Ser Pro Ser Gln
                    405                 410                 415

Thr Val Gln Arg Ala Val Ser Val Asn Pro Gly Lys
                420                 425

<210> SEQ ID NO 44
<211> LENGTH: 3634
<212> TYPE: DNA
<213> ORGANISM: Homo sapiens

<400> SEQUENCE: 44
gaattccggg tgatttcact cccggctgtc caggcttgtc ctgctacccc acccagcctt      60
tcctgaggcc tcaagcctgc caccaagccc cagctccttc tccccgcag acccaaaca      120 caggcctcag gactcaacac agcttttccc tccaacccgt tttctctccc tcaacggact     180
cagctttctg aagcccctcc cagttctagt tctatctttt tcctgcatcc tgtctggaag     240
ttagaaggaa acagaccaca gacctggtcc ccaaaagaaa tggaggcaat aggttttgag    300
gggcatgggg acggggttca gcctccaggg tcctacacac aaatcagtca gtggcccaga    360 agaccccct cggaatcgga gcagggagga tggggagtgt gaggggtatc cttgatgctt      420
gtgtgtcccc aactttccaa atccccgccc cgcgatgga aagaaaccg agacagaagg       480 tgcagggccc actaccgctt cctccagatg agctcatggg tttctccacc aaggaagttt    540
tccgctggtt gaatgattct ttccccgccc tcctctcgcc caggacat ataaaggcag       600 tgttggcac acccagccag cagacgctcc ctcagcaagg acagcagagg accagctaag      660
agggagagaa gcaactacag accccccctg aaaacaaccc tcagacgcca catcccctga    720
caagctgcca ggcaggttct cttcctctca catactgacc cacggcttca ccctctctcc    780
cctggaaagg acaccatgag cactgaaagc atgatccggg acgtggagct ggccgaggag    840
```

```
gcgctcccca agaagacagg ggggccccag ggctccaggc ggtgcttgtt cctcagcctc    900
ttctccttcc tgatcgtggc aggcgccacc acgctcttct gcctgctgca ctttggagtg    960
atcggccccc agagggaaga ggtgagtgcc tggccagcct tcatccactc tcccacccaa   1020
ggggaaatga gagacgcaag agaggggagag agatgggatg ggtgaaagat gtgcgctgat   1080
agggagggat gagagagaaa aaacatggaa gaaagacggg gatgcagaaa gagatgtggc   1140
aagagatggg gaagagagag agagaaagat ggagagacag gatgtctggc acatggaagg   1200
tgctcactaa gtgtgtatgg agtgaatgaa tgaatgaatg aatgaacaag cagatatata   1260
aataagatat ggagacagat gtggggtgtg agaagagaga tggggggaaga aacaagtgat   1320
atgaataaag atggtgagac agaaagagcg ggaaatatga cagctaagga gagagatggg   1380
ggagataagg agagaagaag atagggtgtc tggcacacag aagacactca gggaaagagc   1440
tgttgaatgc tggaaggtga atacacagat gaatggagag agaaaaccag acacctcagg   1500
gctaagagcg caggccagac aggcagccag ctgttcctcc tttaagggtg actccctcga   1560
tgttaaccat tctccttctc cccaacagtt ccccagggac ctctctctaa tcagccctct   1620
ggcccaggca gtcagtaagt gtctccaaac ctctttccta attctgggtt tgggtttggg   1680
ggtagggtta gtaccggtat ggaagcagtg ggggaaattt aaagttttgg tcttggggga   1740
ggatggatgg aggtgaaagt aggggggtat tttctaggaa gtttaagggt ctcagctttt   1800
tcttttctct ctcctcttca ggatcatctt ctcgaacccc gagtgacaag cctgtagccc   1860
atgttgtagg taagagctct gaggatgtgt cttggaactt ggagggctag gatttgggga   1920
ttgaagcccg gctgatggta ggcagaactt ggagacaatg tgagaaggac tcgctgagct   1980
caagggaagg gtggaggaac agcacaggcc ttagtgggat actcagaacg tcatggccag   2040
gtgggatgtg ggatgacaga cagagaggac aggaaccgga tgtggggtgg gcagagctcg   2100
agggccagga tgtggagagt gaaccgacat ggccacactg actctcctct ccctctctcc   2160
ctccctccag caaaccctca agctgagggg cagctccagt ggctgaaccg ccgggccaat   2220
gccctcctgg ccaatggcgt ggagctgaga gataaccagc tggtggtgcc atcagagggc   2280
ctgtacctca tctactccca ggtcctcttc aagggccaag gctgccctc cacccatgtg   2340
ctcctcaccc acaccatcag ccgcatcgcc gtctcctacc agaccaaggt caacctcctc   2400
tctgccatca gagcccctg ccagagggag accccagagg gggctgaggc caagccctgg   2460
tatgagccca tctatctggg aggggtcttc cagctggaga agggtgaccg actcagcgct   2520
gagatcaatc ggcccgacta tctcgacttt gccgagtctg gcaggtcta ctttgggatc   2580
attgccctgt gaggaggacg aacatccaac cttcccaaac gcctcccctg ccccaatccc   2640
tttattaccc cctccttcag acaccctcaa cctcttctgg ctcaaaaaga gaattggggg   2700
cttagggtcg gaacccaagc ttagaacttt aagcaacaag accaccactt cgaaacctgg   2760
gattcaggaa tgtgtggcct gcacagtgaa gtgctggcaa ccactaagaa ttcaaactgg   2820
ggcctccaga actcactggg gcctacagct ttgatccctg acatctggaa tctggagacc   2880
agggagcctt tggttctggc cagaatgctg caggacttga aagacctca cctagaaatt   2940
gacacaagtg gaccttaggc cttcctctct ccagatgttt ccagacttcc ttgagacacg   3000
gagcccagcc ctccccatgg agccagctcc ctctatttat gtttgcactt gtgattattt   3060
attatttatt tattatttat ttatttacag atgaatgtat ttatttggga gaccggggta   3120
tcctggggga cccaatgtag gagctgcctt ggctcagaca tgttttccgt gaaaacggag   3180
```

```
ctgaacaata ggctgttccc atgtagcccc ctggcctctg tgccttcttt tgattatgtt    3240 tttaaaata tttatctgat taagttgtct aaacaatgct gatttggtga ccaactgtca    3300
ctcattgctg agcctctgct ccccagggga gttgtgtctg taatcgccct actattcagt    3360
ggcgagaaat aaagtttgct tagaaaagaa acatggtctc cttcttggaa ttaattctgc    3420
atctgcctct tcttgtgggt gggaagaagc tccctaagtc ctctctccac aggctttaag    3480
atccctcgga cccagtccca tccttagact cctagggccc tggagaccct acataaacaa    3540
agcccaacag aatattcccc atccccagg aaacaagagc ctgaacctaa ttacctctcc    3600
ctcagggcat gggaatttcc aactctggga attc                                3634
```

<210> SEQ ID NO 45
<211> LENGTH: 233
<212> TYPE: PRT
<213> ORGANISM: Homo sapiens

<400> SEQUENCE: 45

```
Met Ser Thr Glu Ser Met Ile Arg Asp Val Glu Leu Ala Glu Ala
1               5                   10                  15

Leu Pro Lys Lys Thr Gly Gly Pro Gln Gly Ser Arg Arg Cys Leu Phe
                20                  25                  30

Leu Ser Leu Phe Ser Phe Leu Ile Val Ala Gly Ala Thr Thr Leu Phe
            35                  40                  45

Cys Leu Leu His Phe Gly Val Ile Gly Pro Gln Arg Glu Glu Phe Pro
        50                  55                  60

Arg Asp Leu Ser Leu Ile Ser Pro Leu Ala Gln Ala Val Arg Ser Ser
65                  70                  75                  80

Ser Arg Thr Pro Ser Asp Lys Pro Val Ala His Val Val Ala Asn Pro
                85                  90                  95

Gln Ala Glu Gly Gln Leu Gln Trp Leu Asn Arg Arg Ala Asn Ala Leu
            100                 105                 110

Leu Ala Asn Gly Val Glu Leu Arg Asp Asn Gln Leu Val Val Pro Ser
        115                 120                 125

Glu Gly Leu Tyr Leu Ile Tyr Ser Gln Val Leu Phe Lys Gly Gln Gly
    130                 135                 140

Cys Pro Ser Thr His Val Leu Leu Thr His Thr Ile Ser Arg Ile Ala
145                 150                 155                 160

Val Ser Tyr Gln Thr Lys Val Asn Leu Leu Ser Ala Ile Lys Ser Pro
                165                 170                 175

Cys Gln Arg Glu Thr Pro Glu Gly Ala Glu Ala Lys Pro Trp Tyr Glu
            180                 185                 190

Pro Ile Tyr Leu Gly Gly Val Phe Gln Leu Glu Lys Gly Asp Arg Leu
        195                 200                 205

Ser Ala Glu Ile Asn Arg Pro Asp Tyr Leu Asp Phe Ala Glu Ser Gly
    210                 215                 220

Gln Val Tyr Phe Gly Ile Ile Ala Leu
225                 230
```

<210> SEQ ID NO 46
<211> LENGTH: 27
<212> TYPE: DNA
<213> ORGANISM: Homo sapiens

<400> SEQUENCE: 46

```
cgggatcccg gctcccactc cttgaag                                          27
```

<210> SEQ ID NO 47
<211> LENGTH: 35
<212> TYPE: DNA
<213> ORGANISM: Homo sapiens

<400> SEQUENCE: 47
cccaagcttg ggttacaagc tgctgtgaga ctcag    35

<210> SEQ ID NO 48
<211> LENGTH: 27
<212> TYPE: DNA
<213> ORGANISM: Homo sapiens

<400> SEQUENCE: 48
cgggatcccg tgtctcgctc cgtggcc    27

<210> SEQ ID NO 49
<211> LENGTH: 41
<212> TYPE: DNA
<213> ORGANISM: Homo sapiens

<400> SEQUENCE: 49
cccaagcttg ggcatgtctc gatcccacta actatcttgg g    41

<210> SEQ ID NO 50
<211> LENGTH: 9
<212> TYPE: PRT
<213> ORGANISM: Homo sapiens

<400> SEQUENCE: 50

Asn Pro Arg Lys Val Thr Ala Tyr Leu
1               5

<210> SEQ ID NO 51
<211> LENGTH: 9
<212> TYPE: PRT
<213> ORGANISM: Homo sapiens

<400> SEQUENCE: 51

Val Met Ala Pro Arg Thr Leu Val Leu
1               5

<210> SEQ ID NO 52
<211> LENGTH: 9
<212> TYPE: PRT
<213> ORGANISM: Homo sapiens

<400> SEQUENCE: 52

Ile Pro Ser Asn Ala Thr Ser Val Thr
1               5

<210> SEQ ID NO 53
<211> LENGTH: 9
<212> TYPE: PRT
<213> ORGANISM: Homo sapiens

<400> SEQUENCE: 53

Leu Pro Arg Ala Leu Met Arg Ser Thr
1               5

<210> SEQ ID NO 54
<211> LENGTH: 9
<212> TYPE: PRT
<213> ORGANISM: Homo sapiens

-continued

```
<400> SEQUENCE: 54

Gln Pro Arg Lys Thr Lys Gly Ser Gly
1               5

<210> SEQ ID NO 55
<211> LENGTH: 9
<212> TYPE: PRT
<213> ORGANISM: Homo sapiens

<400> SEQUENCE: 55

Leu Pro Asp Ala Arg His Ser Thr Thr
1               5

<210> SEQ ID NO 56
<211> LENGTH: 9
<212> TYPE: PRT
<213> ORGANISM: Homo sapiens

<400> SEQUENCE: 56

Ala Pro Ser Lys Gly Thr Val Asn Leu
1               5

<210> SEQ ID NO 57
<211> LENGTH: 9
<212> TYPE: PRT
<213> ORGANISM: Homo sapiens

<400> SEQUENCE: 57

Leu Pro Val Gly Thr Arg Asp Trp Leu
1               5

<210> SEQ ID NO 58
<211> LENGTH: 9
<212> TYPE: PRT
<213> ORGANISM: Homo sapiens

<400> SEQUENCE: 58

Ser Pro Ser Gln Thr Val Gln Arg Ala
1               5

<210> SEQ ID NO 59
<211> LENGTH: 44
<212> TYPE: PRT
<213> ORGANISM: Homo sapiens

<400> SEQUENCE: 59

Ile Leu Gln Ser Ser Cys Asp Gly Gly Gln Ser Ser Cys Asp Gly Gly
1               5                   10                  15

His Ser Cys Asp Gly Gly Gly His Phe Pro Asp Gly Gly His Phe
            20                  25                  30

Pro Pro Thr Gly Gly His Phe Pro Pro Thr Ile Gln
        35                  40

<210> SEQ ID NO 60
<211> LENGTH: 45
<212> TYPE: PRT
<213> ORGANISM: Homo sapiens

<400> SEQUENCE: 60

His Phe Pro Pro Thr Ile Gln Leu Pro Pro Thr Ile Gln Leu Leu
1               5                   10                  15

Cys Leu Thr Ile Gln Leu Leu Cys Leu Val Ser Gln Leu Leu Cys Leu
```

```
              20                  25                  30

Val Ser Gly Tyr Leu Cys Leu Val Ser Gly Tyr Thr Pro
        35                  40                  45

<210> SEQ ID NO 61
<211> LENGTH: 45
<212> TYPE: PRT
<213> ORGANISM: Homo sapiens

<400> SEQUENCE: 61

Leu Val Ser Gly Tyr Thr Pro Gly Thr Ser Gly Tyr Thr Pro Gly Thr
1               5                   10                  15

Ile Asn Tyr Thr Pro Gly Thr Ile Asn Ile Thr Pro Gly Thr Ile Asn
            20                  25                  30

Ile Thr Trp Leu Thr Ile Asn Ile Thr Trp Leu Glu Asp
        35                  40                  45

<210> SEQ ID NO 62
<211> LENGTH: 23
<212> TYPE: DNA
<213> ORGANISM: Homo sapiens

<400> SEQUENCE: 62
tgcctgaatt atccttgact ctt                                          23

<210> SEQ ID NO 63
<211> LENGTH: 28
<212> TYPE: DNA
<213> ORGANISM: Homo sapiens

<400> SEQUENCE: 63
ctcggaatac tctactctac tcggtact                                     28

<210> SEQ ID NO 64
<211> LENGTH: 19
<212> TYPE: DNA
<213> ORGANISM: Homo sapiens

<400> SEQUENCE: 64
ccttctccat ggtggtgaa                                               19

<210> SEQ ID NO 65
<211> LENGTH: 21
<212> TYPE: RNA
<213> ORGANISM: Homo sapiens

<400> SEQUENCE: 65
gaggccagca gacuauuuau u                                            21

<210> SEQ ID NO 66
<211> LENGTH: 21
<212> TYPE: RNA
<213> ORGANISM: Homo sapiens

<400> SEQUENCE: 66
ggacuuggga ggaagaaauu u                                            21

<210> SEQ ID NO 67
<211> LENGTH: 19
<212> TYPE: RNA
<213> ORGANISM: Homo sapiens

<400> SEQUENCE: 67
```

```
acuugggagg aagaaauuu                                              19
```

<210> SEQ ID NO 68
<211> LENGTH: 9
<212> TYPE: PRT
<213> ORGANISM: Homo sapiens

<400> SEQUENCE: 68

Thr Met Thr Leu Pro Ala Thr Thr Leu
1               5

<210> SEQ ID NO 69
<211> LENGTH: 9
<212> TYPE: PRT
<213> ORGANISM: Homo sapiens

<400> SEQUENCE: 69

Thr Met Lys Leu Pro Ala Thr Thr Leu
1               5

<210> SEQ ID NO 70
<211> LENGTH: 9
<212> TYPE: PRT
<213> ORGANISM: Homo sapiens

<400> SEQUENCE: 70

Thr Met Asn Leu Pro Ala Thr Thr Leu
1               5

<210> SEQ ID NO 71
<211> LENGTH: 9
<212> TYPE: PRT
<213> ORGANISM: Homo sapiens

<400> SEQUENCE: 71

Thr Met Ala Leu Pro Ala Thr Thr Leu
1               5

<210> SEQ ID NO 72
<211> LENGTH: 9
<212> TYPE: PRT
<213> ORGANISM: Homo sapiens

<400> SEQUENCE: 72

Thr Met Gln Leu Pro Ala Thr Thr Leu
1               5

<210> SEQ ID NO 73
<211> LENGTH: 9
<212> TYPE: PRT
<213> ORGANISM: Homo sapiens

<400> SEQUENCE: 73

Thr Met Thr Leu Pro Thr Thr Thr Leu
1               5

<210> SEQ ID NO 74
<211> LENGTH: 9
<212> TYPE: PRT
<213> ORGANISM: Homo sapiens

<400> SEQUENCE: 74

Thr Met Thr Leu Pro Ser Thr Thr Leu
1               5

<210> SEQ ID NO 75
<211> LENGTH: 9
<212> TYPE: PRT
<213> ORGANISM: Homo sapiens

<400> SEQUENCE: 75

Thr Met Thr Leu Pro Val Thr Thr Leu
1               5

<210> SEQ ID NO 76
<211> LENGTH: 9
<212> TYPE: PRT
<213> ORGANISM: Homo sapiens

<400> SEQUENCE: 76

Thr Met Thr Leu Pro Ala Leu Thr Leu
1               5

<210> SEQ ID NO 77
<211> LENGTH: 9
<212> TYPE: PRT
<213> ORGANISM: Homo sapiens

<400> SEQUENCE: 77

Thr Met Thr Leu Pro Ala Val Thr Leu
1               5

<210> SEQ ID NO 78
<211> LENGTH: 9
<212> TYPE: PRT
<213> ORGANISM: Homo sapiens

<400> SEQUENCE: 78

Thr Met Thr Leu Pro Ala Pro Thr Leu
1               5

<210> SEQ ID NO 79
<211> LENGTH: 9
<212> TYPE: PRT
<213> ORGANISM: Homo sapiens

<400> SEQUENCE: 79

Thr Met Lys Leu Pro Thr Thr Thr Leu
1               5

<210> SEQ ID NO 80
<211> LENGTH: 9
<212> TYPE: PRT
<213> ORGANISM: Homo sapiens

<400> SEQUENCE: 80

Thr Met Gln Leu Pro Ala Pro Thr Leu
1               5

<210> SEQ ID NO 81
<211> LENGTH: 847
<212> TYPE: DNA
<213> ORGANISM: CMV

<400> SEQUENCE: 81
tttcttcgcc tcgggctctg tctcgtcgtc attcgggcca ggactttta atggccaaca      60 gcctgtggca ccgcctccga acgctcgtga gcaacagtcg gcagaatgaa caaattcagc    120

```
aacactcgta tcggcttcac ttgcgcggtt atggctccgc ggactttaat tctgacggtt    180
ggactcctgt gtatgaggat caggagttta ttgtcttctc ctgtcgagac gacggtaaca    240
accgccggcg tgacgtccgc tcacggtccg ctatgtccgc tcgtgttcca gggttgggcg    300
tacgccgtgt accaccaagg cgacatggtc ctcatgacgc tcgacgtgta ctgctgccgc    360
cagacctcca gcaacaccgt cgtcgcgttc tcgcatcatc ctgccgataa cacgttgctg    420
atcgaagtgg gtaacaacac gcgtcgccac gtagacggaa tctcctgtca ggaccatttt    480
cgcgcgcaac accaggattg cccggcccag acggtgcacg tgcgcggcgt aaacgaaagc    540
gcttttgggc tcacccacct gcagtcctgt tgcctgaacg agcattcaca actctcggag    600
cgggtggcct accatctgaa gctgcgaccc gccacgttcg gtctggagac ctgggccatg    660
tacactgtgg gcattctggc cttggggtcg ttctcctcct tctattccca gatcgctagg    720
agcctggggg ttctgcccaa cgatcatcac tacgccttga agaaggcttg ataatgataa    780
ctgcacatcc tcacgagtgc ccttacctat catcacacta agaataaaga aaatcgatcg    840
gtgtcgt                                                              847
```

<210> SEQ ID NO 82
<211> LENGTH: 221
<212> TYPE: PRT
<213> ORGANISM: CMV

<400> SEQUENCE: 82

```
Met Asn Lys Phe Ser Asn Thr Arg Ile Gly Phe Thr Cys Ala Val Met
1               5                   10                  15

Ala Pro Arg Thr Leu Ile Leu Thr Val Gly Leu Leu Cys Met Arg Ile
            20                  25                  30

Arg Ser Leu Leu Ser Ser Pro Val Glu Thr Thr Val Thr Thr Ala Gly
        35                  40                  45

Val Thr Ser Ala His Gly Pro Leu Cys Pro Leu Val Phe Gln Gly Trp
    50                  55                  60

Ala Tyr Ala Val Tyr His Gln Gly Asp Met Val Leu Met Thr Leu Asp
65                  70                  75                  80

Val Tyr Cys Cys Arg Gln Thr Ser Asn Thr Val Val Ala Phe Ser
                85                  90                  95

His His Pro Ala Asp Asn Thr Leu Leu Ile Glu Val Gly Asn Asn Thr
            100                 105                 110

Arg Arg His Val Asp Gly Ile Ser Cys Gln Asp His Phe Arg Ala Gln
        115                 120                 125

His Gln Asp Cys Pro Ala Gln Thr Val His Val Arg Gly Val Asn Glu
    130                 135                 140

Ser Ala Phe Gly Leu Thr His Leu Gln Ser Cys Cys Leu Asn Glu His
145                 150                 155                 160

Ser Gln Leu Ser Glu Arg Val Ala Tyr His Leu Lys Leu Arg Pro Ala
                165                 170                 175

Thr Phe Gly Leu Glu Thr Trp Ala Met Tyr Thr Val Gly Ile Leu Ala
            180                 185                 190

Leu Gly Ser Phe Ser Ser Phe Tyr Ser Gln Ile Ala Arg Ser Leu Gly
        195                 200                 205

Val Leu Pro Asn Asp His His Tyr Ala Leu Lys Lys Ala
    210                 215                 220
```

<210> SEQ ID NO 83
<211> LENGTH: 57

<212> TYPE: DNA
<213> ORGANISM: Homo sapiens

<400> SEQUENCE: 83

| | | | | | |
|---|---|---|---|---|---|
| ggcggctccg | gaggtggtgg | ctctggtgga | ggtggatcgt | ctcgctccgt | ggcctta | 57 |

<210> SEQ ID NO 84
<211> LENGTH: 45
<212> TYPE: DNA
<213> ORGANISM: Homo sapiens

<400> SEQUENCE: 84

| | | | | |
|---|---|---|---|---|
| gccaccacct | ccggagccgc | cacctccgat | ggtgggctgg | gaagc | 45 |

<210> SEQ ID NO 85
<211> LENGTH: 3213
<212> TYPE: DNA
<213> ORGANISM: Homo sapiens

<400> SEQUENCE: 85

| | | | | | |
|---|---|---|---|---|---|
| agaaggctgc | ctcgctggtc | cgaattcggt | ggcgccacgt | ccgcccgtct | ccgccttctg | 60 |
| catcgcggct | tcggcggctt | ccacctagac | acctaacagt | cgcggagccg | ccgcgtcgt | 120 |
| gaggggtcg | gcacggggag | tcgggcggtc | ttgtgcatct | tggctacctg | tgggtcgaag | 180 |
| atgtcggaca | tcgagactg | gttcaggagc | atcccggcga | tcacgcgcta | ttggttcgcc | 240 |
| gccaccgtcg | ccgtgccctt | ggtcggcaaa | tcggcctca | tcagcccggc | ctacctcttc | 300 |
| ctctggcccg | aagccttcct | ttatcgcttt | cagatttgga | ggccaatcac | tgccaccttt | 360 |
| tatttccctg | tgggtccagg | aactggattt | ctttatttgg | tcaatttata | tttcttatat | 420 |
| cagtattcta | cgcgacttga | acaggagct | tttgatggga | ggccagcaga | ctatttattc | 480 |
| atgctcctct | ttaactggat | ttgcatcgtg | attactggct | tagcaatgga | tatgcagttg | 540 |
| ctgatgattc | ctctgatcat | gtcagtactt | tatgtctggg | cccagctgaa | cagagacatg | 600 |
| attgtatcat | tttggtttgg | aacacgattt | aaggcctgct | atttaccctg | gttatccctt | 660 |
| ggattcaact | atatcatcgg | aggctcggta | atcaatgagc | ttattggaaa | tctggttgga | 720 |
| catctttatt | ttttcctaat | gttcagatac | ccaatggact | tgggaggaag | aaattttcta | 780 |
| tccacacctc | agttttttgta | ccgctggctg | cccagtagga | gaggaggagt | atcaggattt | 840 |
| ggtgtgcccc | ctgctagcat | gaggcagct | gctgatcaga | atggcggagg | cgggagacac | 900 |
| aactggggcc | agggctttcg | acttggagac | cagtgaaggg | gcggcctcgg | gcagccgctc | 960 |
| ctctcaagcc | acatttcctc | ccagtgctgg | gtgcacttaa | caactgcgtt | ctggctaaca | 1020 |
| ctgttggacc | tgacccacac | tgaatgtagt | ctttcagtac | gagacaaagt | ttcttaaatc | 1080 |
| ccgaagaaaa | atataagtgt | tccacaagtt | tcacgattct | cattcaagtc | cttactgctg | 1140 |
| tgaagaacaa | ataccaactg | tgcaaattgc | aaaactgact | acatttttg | gtgtcttctc | 1200 |
| ttctccccctt | tccgtctgaa | taatgggttt | tagcgggtcc | tagtctgctg | gcattgagct | 1260 |
| ggggctgggt | caccaaaccc | ttcccaaaag | gacccttatc | tctttcttgc | acacatgcct | 1320 |
| ctctcccact | tttcccaacc | cccacatttg | caactagaag | aggttgccca | taaaattgct | 1380 |
| ctgcccttga | caggttctgt | tatttattga | cttttgccaa | ggcttggtca | caacaatcat | 1440 |
| attcacgtaa | ttttccccct | ttggtggcag | aactgtagca | ataggggag | aagacaagca | 1500 |
| gcggatgaag | cgttttctca | gcttttggaa | ttgcttcgac | ctgacatccg | ttgtaaccgt | 1560 |
| ttgccacttc | ttcagatatt | tttataaaaa | agtaccactg | agtcagtgag | ggccacagat | 1620 |

-continued

```
tggtattaat gagatacgag ggttgttgct gggtgtttgt ttcctgagct aagtgatcaa    1680
gactgtagtg gagttgcagc taacatgggt taggtttaaa ccatggggga tgcaaccect    1740
ttgcgtttca tatgtaggcc tactggcttt gtgtagctgg agtagttggg ttgctttgtg    1800
ttaggaggat ccagatcatg ttggctacag ggagatgctc tctttgagag gctcctgggc    1860
attgattcca tttcaatctc attctggata tgtgttcatt gagtaaagga ggagagaccc    1920
tcatacgcta tttaaatgtc acttttttgc ctatccccecg ttttttggtc atgtttcaat    1980
taattgtgag gaaggcgcag ctcctctctg cacgtagatc attttttaaa gctaatgtaa    2040
gcacatctaa gggaataaca tgatttaagg ttgaaatggc tttagaatca tttgggtttg    2100
agggtgtgtt attttgagtc atgaatgtac aagctctgtg aatcagacca gcttaaatac    2160
ccacaccttt ttttcgtagg tgggcttttc ctatcagagc ttggctcata accaaataaa    2220
gttttttgaa ggccatggct tttcacacag ttattttatt ttatgacgtt atctgaaagc    2280
agactgttag gagcagtatt gagtggctgt cacactttga ggcaactaaa aaggcttcaa    2340
acgttttgat cagtttctt tcaggaaaca ttgtgctcta acagtatgac tattctttcc     2400
cccactctta aacagtgtga tgtgtgttat cctaggaaat gagagttggc aaacaacttc    2460
tcattttgaa tagagtttgt gtgtacctct ccatatttaa tttatatgat aaaataggtg    2520
gggagagtct gaaccttaac tgtcatgttt tgttgttcat ctgtggccac aataaagttt    2580
acttgtaaaa ttttagaggc cattactcca attatgttgc acgtacactc attgtacagg    2640
cgtggagact cattgtatgt ataagaatat tctgacagtg agtgacccgg agtctctggt    2700
gtaccctctt accagtcagc tgcctgcgag cagtcatttt ttcctaaagg tttacaagta    2760
tttagaactc ttcagttcag ggcaaaatgt tcatgaagtt attcctctta aacatggtta    2820
ggaagctgat gacgttattg attttgtctg gattatgttt ctggaataat tttaccaaaa    2880
caagctattt gagttttgac ttgacaaggc aaaacatgac agtggattct ctttacaaat    2940
ggaaaaaaaa aatccttatt ttgtataaag gacttccctt tttgtaaact aatccttttt    3000
attggtaaaa attgtaaatt aaaatgtgca acttgaaggt tgtctgtgtt aagtttccat    3060
gtccctgctc tgctgtctct tagatatcac ataaattgtg taaccaatta tctcttgaag    3120
agcatttagg aagtacccag tatttttgc tggattaatt cctggatgca gaattcctgg     3180
gttttcattt taatgaagga ggatgcttgc taa                                 3213
```

<210> SEQ ID NO 86
<211> LENGTH: 251
<212> TYPE: PRT
<213> ORGANISM: Homo sapiens

<400> SEQUENCE: 86

```
Met Ser Asp Ile Gly Asp Trp Phe Arg Ser Ile Pro Ala Ile Thr Arg
1               5                   10                  15

Tyr Trp Phe Ala Ala Thr Val Ala Val Pro Leu Val Gly Lys Leu Gly
            20                  25                  30

Leu Ile Ser Pro Ala Tyr Leu Phe Leu Trp Pro Glu Ala Phe Leu Tyr
        35                  40                  45

Arg Phe Gln Ile Trp Arg Pro Ile Thr Ala Thr Phe Tyr Phe Pro Val
    50                  55                  60

Gly Pro Gly Thr Gly Phe Leu Tyr Leu Val Asn Leu Tyr Phe Leu Tyr
65                  70                  75                  80

Gln Tyr Ser Thr Arg Leu Glu Thr Gly Ala Phe Asp Gly Arg Pro Ala
            85                  90                  95
```

```
Asp Tyr Leu Phe Met Leu Leu Phe Asn Trp Ile Cys Ile Val Ile Thr
                100                 105                 110

Gly Leu Ala Met Asp Met Gln Leu Leu Met Ile Pro Leu Ile Met Ser
            115                 120                 125

Val Leu Tyr Val Trp Ala Gln Leu Asn Arg Asp Met Ile Val Ser Phe
        130                 135                 140

Trp Phe Gly Thr Arg Phe Lys Ala Cys Tyr Leu Pro Trp Val Ile Leu
145                 150                 155                 160

Gly Phe Asn Tyr Ile Ile Gly Gly Ser Val Ile Asn Glu Leu Ile Gly
                165                 170                 175

Asn Leu Val Gly His Leu Tyr Phe Phe Leu Met Phe Arg Tyr Pro Met
            180                 185                 190

Asp Leu Gly Gly Arg Asn Phe Leu Ser Thr Pro Gln Phe Leu Tyr Arg
        195                 200                 205

Trp Leu Pro Ser Arg Arg Gly Gly Val Ser Gly Phe Gly Val Pro Pro
210                 215                 220

Ala Ser Met Arg Arg Ala Ala Asp Gln Asn Gly Gly Gly Arg His
225                 230                 235                 240

Asn Trp Gly Gln Gly Phe Arg Leu Gly Asp Gln
                245                 250

<210> SEQ ID NO 87
<211> LENGTH: 1372
<212> TYPE: DNA
<213> ORGANISM: CMV

<400> SEQUENCE: 87
aataaaaggg ggcgtgagga ccgggaggcg gccagaaccg ccgtgcacga cccggagcgt      60
cccctgctgc gctctcccgg gctgctgccc gaaatcgccc caacgcatc cttgggtgtg     120 gcacatcgaa gaaccggcgg gaccgtgacc gacagtcccc gtaatccggt aacccgttga    180
gtcccgggta cgaccatcac ccgagtctct gggcggaggg tggttccccc ccgtggctct    240
cgagatgagc cagacccaac ccccggcccc agttgggccg ggcgacccag atgtttactt    300
aaaaggcgtg ccgtccgccg gcatgcaccc cagaggtgtt cacgcacctc gaggacaccc    360
gcgcatgatc tccggacccc cgcaacgggg tgataatgat caagcggcgg ggcaatgtgg    420
agattcgggt ctactacgag tcggtgcgga cactacgatc tcgaagccat ctgaagccgt    480
ccgaccgcca acaatcccca ggacaccgcg tgttccccgg gagccccggg ttccgcgacc    540
accccgagaa cctagggaac ccagagtacc gcgagctccc agagacccca gggtaccgcg    600
tgaccccagg gatccacgac aaccccggtc tcccagggag cccggtctc cccgggagcc     660 ccggtctccc cggggagcccc ggaccccacg cacccccgc gaaccacgta cggctcgcgg    720
gtctgtatag cccgggcaag tatgcccccc tggcgagccc agaccccttc tccccacaac    780
atggagcata cgctcgggcc cgcgtcggga tccacaccgc ggttcgcgtc ccgcccaccg    840
gaagcccaac ccacacgcac ttgcggcaag acccgggcga tgagccaacc tcggatgact    900
cagggctcta ccctctggac gcccgggcgc ttgcgcacct ggtgatgttg cccgcggacc    960
accgggcctt ctttcgaacc gtggtcgagg tgtctcgcat gtcgctgca aacgtgcgcg   1020 atccccccgcc cccggctaca ggggccatgt tgggccgcca cgcgcggctg gtccacaccc   1080
agtggctccg ggccaaccaa gagacgtcgc cctgtggcc ctggcggacg gcggccatta    1140
actttatcac caccatggcc cccgcgtcc aaacccaccg acacatgcac gacctgttga    1200
```

```
tggcctgtgc tttctggtgc tgtctgacac acgcatcgac gtgttcgtac gcggggctgt    1260
actcgaccca ctgcctgcat ctgtttggtg cgtttgggtg tggggacccg gccctaaccc    1320
caccccgtgt ctagggcaat ttgtacccct aataaatttt acaaacagat tt            1372
```

<210> SEQ ID NO 88
<211> LENGTH: 215
<212> TYPE: PRT
<213> ORGANISM: CMV

<400> SEQUENCE: 88

```
Met Asn Leu Val Met Leu Ile Leu Ala Leu Trp Ala Pro Val Ala Gly
1               5                   10                  15

Ser Met Pro Glu Leu Ser Leu Thr Leu Phe Asp Glu Pro Pro Pro Leu
            20                  25                  30

Val Glu Thr Glu Pro Leu Pro Pro Leu Pro Asp Val Ser Glu Tyr Arg
        35                  40                  45

Val Glu Ser Ser Glu Ala Arg Cys Val Leu Arg Ser Gly Gly Arg Leu
    50                  55                  60

Glu Ala Leu Trp Thr Leu Arg Gly Asn Leu Ser Val Pro Thr Pro Thr
65                  70                  75                  80

Pro Arg Val Tyr Tyr Gln Thr Leu Glu Gly Tyr Ala Asp Arg Val Pro
                85                  90                  95

Thr Pro Val Glu Asp Val Ser Ser Leu Val Ala Lys Arg Tyr Trp
                100                 105                 110

Leu Arg Asp Tyr Arg Val Pro Gln Arg Thr Lys Leu Val Leu Phe Tyr
            115                 120                 125

Phe Ser Pro Cys His Gln Cys Gln Thr Tyr Tyr Val Glu Cys Glu Pro
        130                 135                 140

Arg Cys Leu Val Pro Trp Val Pro Leu Trp Ser Ser Leu Glu Asp Ile
145                 150                 155                 160

Glu Arg Leu Leu Phe Glu Asp Arg Arg Leu Met Ala Tyr Tyr Ala Leu
                165                 170                 175

Thr Ile Lys Ser Ala Gln Tyr Thr Leu Met Met Val Ala Val Ile Gln
            180                 185                 190

Val Phe Trp Gly Leu Tyr Val Lys Gly Trp Leu His Arg His Phe Pro
        195                 200                 205

Trp Met Phe Ser Asp Gln Trp
    210                 215
```

<210> SEQ ID NO 89
<211> LENGTH: 600
<212> TYPE: DNA
<213> ORGANISM: CMV

<400> SEQUENCE: 89

```
atgaacaatc tctggaaagc ctgggtgggt ctttggacct ccatgggtcc cttgatccgc     60
ctgcccgatg gcatcactaa agccggggaa gacgcgctcc ggccctggaa gtccacggcc    120
aagcacccct ggtttgagat cgaggacaac cggtgctaca ttgacaacgg caagttgttt    180
gctcggggga gcatcgtggg caacatgagt cggttcgtct tcgatccgaa ggccgattat    240
ggcggcgtgg gagagaacct gtacgtacac gccgacgacg tggagttcgt tcccggggag    300
tcgttaaagt ggaacgtgcg gaacttagat gtgatgccga tcttcgagac gctagccctg    360 cgtctgtac  tgcaagggga tgtgatctgg ctgcgttgcg tccccgaact gcgagtggat    420
tacacgtcta gcgcgtacat gtggaacatg cagtacggga tggtgcggaa gtcatacacg    480
```

-continued

```
catgtggcct ggacaatagt gttttactcc ataaacatta ccctgttggt attgtttatc    540
gtgtatgtga ctgtggactg taacttgtct atgatgtgga tgcggttttt cgtgtgctaa    600
```

<210> SEQ ID NO 90
<211> LENGTH: 198
<212> TYPE: PRT
<213> ORGANISM: CMV

<400> SEQUENCE: 90

```
Asn Asn Leu Trp Lys Ala Trp Val Gly Leu Trp Thr Ser Met Gly Pro
1               5                   10                  15

Leu Ile Arg Leu Pro Asp Gly Ile Thr Lys Ala Gly Glu Asp Ala Leu
            20                  25                  30

Arg Pro Trp Lys Ser Thr Ala Lys His Pro Trp Phe Glu Ile Glu Asp
        35                  40                  45

Asn Arg Cys Tyr Ile Asp Asn Gly Lys Leu Phe Ala Arg Gly Ser Ile
    50                  55                  60

Val Gly Asn Met Ser Arg Phe Val Phe Asp Pro Lys Ala Asp Tyr Gly
65                  70                  75                  80

Gly Val Gly Glu Asn Leu Tyr Val His Ala Asp Val Glu Phe Val
                85                  90                  95

Pro Gly Glu Ser Leu Lys Trp Asn Val Arg Asn Leu Asp Val Met Pro
            100                 105                 110

Ile Phe Glu Thr Leu Ala Leu Arg Leu Val Leu Gln Gly Asp Val Ile
        115                 120                 125

Trp Leu Arg Cys Val Pro Glu Leu Arg Val Asp Tyr Thr Ser Ser Ala
    130                 135                 140

Tyr Met Trp Asn Met Gln Tyr Gly Met Val Arg Lys Ser Tyr Thr His
145                 150                 155                 160

Val Ala Trp Thr Ile Val Phe Tyr Ser Ile Asn Ile Thr Leu Leu Val
                165                 170                 175

Leu Phe Ile Val Tyr Val Thr Val Asp Cys Asn Leu Ser Met Met Trp
            180                 185                 190

Met Arg Phe Phe Val Cys
            195
```